US011497576B2

(12) United States Patent
Kells et al.

(10) Patent No.: US 11,497,576 B2
(45) Date of Patent: Nov. 15, 2022

(54) TRAJECTORY ARRAY GUIDE SYSTEM

(71) Applicants: VOYAGER THERAPEUTICS, INC., Cambridge, MA (US); THE REGENTS OF THE UNIVERSITY OF CALIFORNIA, Oakland, CA (US)

(72) Inventors: Adrian Philip Kells, Cambridge, MA (US); Stefan Schreck, Duvall, WA (US); Edward H. Luttich, Fallbrook, CA (US); Kenneth A. Bloch, San Diego, CA (US); Krystof Bankiewicz, Oakland, CA (US)

(73) Assignees: Voyager Therapeutics, Inc., Cambridge, MA (US); The Regents of the University of California, Oakland, CA (US)

( * ) Notice: Subject to any disclaimer, the term of this patent is extended or adjusted under 35 U.S.C. 154(b) by 181 days.

(21) Appl. No.: 16/631,982

(22) PCT Filed: Jul. 17, 2018

(86) PCT No.: PCT/US2018/042391
§ 371 (c)(1),
(2) Date: Jan. 17, 2020

(87) PCT Pub. No.: WO2019/018342
PCT Pub. Date: Jan. 24, 2019

(65) Prior Publication Data
US 2020/0229889 A1 Jul. 23, 2020

Related U.S. Application Data

(60) Provisional application No. 62/533,207, filed on Jul. 17, 2017.

(51) Int. Cl.
*A61B 5/00* (2006.01)
*A61B 90/11* (2016.01)
(Continued)

(52) U.S. Cl.
CPC .............. *A61B 90/11* (2016.02); *A61B 34/20* (2016.02); *A61M 25/0127* (2013.01);
(Continued)

(58) Field of Classification Search
CPC combination set(s) only.
See application file for complete search history.

(56) References Cited

U.S. PATENT DOCUMENTS 5,064,764 A 11/1991 Besnainon
5,163,430 A 11/1992 Carol
(Continued)

FOREIGN PATENT DOCUMENTS

CA 2109955 A1 11/1992
CA 2259214 A1 12/1997
(Continued)

OTHER PUBLICATIONS

Maniatis T. et al.,Molecular Cloning. CSH Laboratory, NY, N.Y. (1982).
(Continued)

*Primary Examiner* — Joel F Brutus
(74) *Attorney, Agent, or Firm* — Nelson Mullins Riley & Scarborough LLP; Anthony A. Laurentano

(57) ABSTRACT

The present disclosure presents a trajectory array guide system for defining a trajectory to a target location in the brain of a subject and for guiding an elongated tool along the trajectory. The trajectory array guide system can comprise: a base, an array guide, an imaging unit, and an elongated handle configured for connection with a stereotaxic navigation system. The present disclosure presents a method of using a trajectory array guide system for defining a trajectory to a target location in the brain of a subject and for guiding an elongated tool along the trajectory.

40 Claims, 38 Drawing Sheets

(51) Int. Cl.
    *A61B 34/20*      (2016.01)
    *A61M 25/01*      (2006.01)
    *G01R 33/56*      (2006.01)
    *A61B 34/10*      (2016.01)
    *A61B 90/10*      (2016.01)
    *A61B 90/00*      (2016.01)
    *A61B 17/86*      (2006.01)
    *A61B 17/00*      (2006.01)
    *A61B 17/34*      (2006.01)

(52) U.S. Cl.
    CPC .......... *G01R 33/5601* (2013.01); *A61B 17/86* (2013.01); *A61B 2017/0042* (2013.01); *A61B 2017/00725* (2013.01); *A61B 2017/3407* (2013.01); *A61B 2017/3411* (2013.01); *A61B 2034/107* (2016.02); *A61B 2034/2051* (2016.02); *A61B 2034/2068* (2016.02); *A61B 2090/103* (2016.02); *A61B 2090/374* (2016.02)

(56) References Cited

U.S. PATENT DOCUMENTS

| | | |
|---|---|---|
| 5,474,935 A | 12/1995 | Chatterjee |
| 5,487,739 A | 1/1996 | Aebischer |
| 5,538,885 A | 7/1996 | Hollis |
| 5,569,267 A | 10/1996 | Howard, III |
| 5,587,308 A | 12/1996 | Carter |
| 5,643,286 A | 7/1997 | Warner |
| 5,652,224 A | 7/1997 | Wilson |
| 5,658,785 A | 8/1997 | Johnson |
| 5,676,655 A | 10/1997 | Howard, III |
| 5,688,676 A | 11/1997 | Zhou |
| 5,691,176 A | 11/1997 | Lebkowski |
| 5,693,531 A | 12/1997 | Chiorini |
| 5,713,858 A | 2/1998 | Heruth |
| 5,741,683 A | 4/1998 | Zhou |
| 5,756,283 A | 5/1998 | Wilson |
| 5,776,143 A | 7/1998 | Adams |
| 5,776,144 A | 7/1998 | Leysieffer |
| 5,788,713 A | 8/1998 | Dubach |
| 5,792,110 A | 8/1998 | Cunningham |
| 5,856,152 A | 1/1999 | Wilson |
| 5,858,351 A | 1/1999 | Podsakoff |
| 5,858,775 A | 1/1999 | Johnson |
| 5,865,842 A | 2/1999 | Knuth |
| 5,866,552 A | 2/1999 | Wilson |
| 5,866,696 A | 2/1999 | Carter |
| 5,871,487 A | 2/1999 | Warner |
| 5,871,982 A | 2/1999 | Wilson |
| 5,913,852 A | 6/1999 | Magram |
| 5,927,277 A | 7/1999 | Baudino |
| 5,952,221 A | 9/1999 | Kurtzman |
| 5,954,687 A | 9/1999 | Baudino |
| 5,962,313 A | 10/1999 | Podsakoff |
| 5,989,540 A | 11/1999 | Carter |
| 5,993,463 A | 11/1999 | Truwit |
| 6,061,587 A | 5/2000 | Kucharczyk |
| 6,083,716 A | 7/2000 | Wilson |
| 6,143,548 A | 11/2000 | ORiordan et al. |
| 6,143,567 A | 11/2000 | Van Agthoven |
| 6,146,874 A | 11/2000 | Zolotukhin |
| 6,156,303 A | 12/2000 | Russell |
| 6,165,139 A | 12/2000 | Damadian |
| 6,174,527 B1 | 1/2001 | Wilson |
| 6,180,613 B1 | 1/2001 | Kaplitt |
| 6,190,393 B1 | 2/2001 | Bevier |
| 6,194,191 B1 | 2/2001 | Zhang |
| 6,195,577 B1 | 2/2001 | Truwit |
| 6,200,560 B1 | 3/2001 | Couto |
| 6,204,059 B1 | 3/2001 | Samulski |
| 6,206,890 B1 | 3/2001 | Truwit |
| 6,211,163 B1 | 4/2001 | Podsakoff |
| 6,214,016 B1 | 4/2001 | Williams |
| 6,251,677 B1 | 6/2001 | Wilson |
| 6,258,595 B1 | 7/2001 | Gao |
| 6,261,241 B1 | 7/2001 | Burbank |
| 6,261,300 B1 | 7/2001 | Day |
| 6,261,551 B1 | 7/2001 | Wilson |
| 6,265,389 B1 | 7/2001 | Burke |
| 6,267,769 B1 | 7/2001 | Truwit |
| 6,270,996 B1 | 8/2001 | Wilson |
| 6,274,354 B1 | 8/2001 | Wilson |
| 6,281,010 B1 | 8/2001 | Gao |
| 6,309,634 B1 | 10/2001 | Bankiewicz |
| 6,325,998 B1 | 12/2001 | Podsakoff |
| 6,335,011 B1 | 1/2002 | Podsakoff |
| 6,353,762 B1 | 3/2002 | Baudino |
| 6,365,394 B1 | 4/2002 | Gao |
| 6,387,368 B1 | 5/2002 | Wilson |
| 6,399,385 B1 | 6/2002 | Croyle |
| 6,410,300 B1 | 6/2002 | Samulski |
| 6,416,992 B1 | 7/2002 | Mejza |
| 6,428,988 B1 | 8/2002 | Wilson |
| 6,436,392 B1 | 8/2002 | Engelhardt |
| 6,436,394 B1 | 8/2002 | Henderson |
| 6,468,524 B1 | 10/2002 | Chiorini |
| 6,468,771 B1 | 10/2002 | Einerhand |
| 6,475,769 B1 | 11/2002 | Wilson |
| 6,482,634 B1 | 11/2002 | Wilson |
| 6,485,966 B2 | 11/2002 | Gao |
| 6,490,467 B1 | 12/2002 | Bucholz |
| 6,503,888 B1 | 1/2003 | Kaplitt |
| 6,509,150 B1 | 1/2003 | Salvetti |
| 6,521,426 B1 | 2/2003 | Ciliberto |
| 6,529,765 B1 | 3/2003 | Franck |
| 6,537,232 B1 | 3/2003 | Kucharczyk |
| 6,537,241 B1 | 3/2003 | Odland |
| 6,555,525 B2 | 4/2003 | Burke |
| 6,566,118 B1 | 5/2003 | Atkinson |
| 6,567,687 B2 | 5/2003 | Front |
| 6,572,624 B2 | 6/2003 | U |
| 6,582,692 B1 | 6/2003 | Podsakoff |
| 6,593,123 B1 | 7/2003 | Wright |
| 6,599,267 B1 | 7/2003 | Ray |
| 6,602,241 B2 | 8/2003 | Makower |
| 6,609,020 B2 | 8/2003 | Gill |
| 6,610,290 B2 | 8/2003 | Podsakoff |
| 6,623,490 B1 | 9/2003 | Crane |
| 6,632,184 B1 | 10/2003 | Truwit |
| 6,642,051 B1 | 11/2003 | Lynch |
| 6,656,152 B2 | 12/2003 | Putz |
| 6,660,514 B1 | 12/2003 | Zolotukhin |
| 6,660,521 B2 | 12/2003 | Brough |
| 6,670,176 B1 | 12/2003 | Samulski |
| 6,676,669 B2 | 1/2004 | Charles |
| 6,676,935 B2 | 1/2004 | Henderson |
| 6,699,706 B1 | 3/2004 | Brooks |
| 6,702,782 B2 | 3/2004 | Miller |
| 6,710,036 B2 | 3/2004 | Kurtzman |
| 6,723,551 B2 | 4/2004 | Kotin |
| 6,726,907 B2 | 4/2004 | Zhang |
| 6,752,812 B1 | 6/2004 | Truwit |
| 6,753,419 B1 | 6/2004 | Toniatti |
| 6,759,237 B1 | 7/2004 | Wilson |
| 6,773,443 B2 | 8/2004 | Truwit |
| 6,793,664 B2 | 9/2004 | Mazzocchi |
| 6,795,737 B2 | 9/2004 | Gielen |
| 6,841,357 B1 | 1/2005 | Vaillancourt |
| 6,846,665 B1 | 1/2005 | Horer |
| 6,855,314 B1 | 2/2005 | Chiorini |
| 6,887,463 B2 | 5/2005 | Wilson |
| 6,889,073 B2 | 5/2005 | Lampman |
| 6,897,045 B2 | 5/2005 | Engelhardt |
| 6,902,569 B2 | 6/2005 | Parmer |
| 6,918,881 B2 | 7/2005 | Miller |
| 6,939,318 B2 | 9/2005 | Stenzel |
| 6,943,019 B2 | 9/2005 | Wilson |
| 6,953,575 B2 | 10/2005 | Bankiewicz |
| 6,953,690 B1 | 10/2005 | Gao |
| 6,974,448 B2 | 12/2005 | Petersen |
| 6,984,517 B1 | 1/2006 | Chiorini |
| 6,989,015 B2 | 1/2006 | Daum |
| 6,995,006 B2 | 2/2006 | Atkinson |

(56) References Cited

U.S. PATENT DOCUMENTS

| | | |
|---|---|---|
| 7,015,026 B2 | 3/2006 | ORiordan |
| 7,022,519 B2 | 4/2006 | Gao |
| 7,033,326 B1 | 4/2006 | Pianca |
| 7,048,920 B2 | 5/2006 | Yu |
| 7,056,502 B2 | 6/2006 | Hildinger |
| 7,070,998 B2 | 7/2006 | Johnson |
| 7,091,030 B2 | 8/2006 | Setiawan |
| 7,094,604 B2 | 8/2006 | Snyder |
| 7,103,418 B2 | 9/2006 | Laske |
| 7,105,345 B2 | 9/2006 | Wilson |
| 7,112,321 B2 | 9/2006 | Wang |
| 7,122,038 B2 | 10/2006 | Thomas |
| 7,125,705 B2 | 10/2006 | Colosi |
| 7,125,706 B2 | 10/2006 | Zhang |
| 7,169,612 B2 | 1/2007 | Kostenis |
| 7,182,944 B2 | 2/2007 | Bankiewicz |
| 7,186,552 B2 | 3/2007 | Wilson |
| 7,198,951 B2 | 4/2007 | Gao |
| 7,217,276 B2 | 5/2007 | Henderson |
| 7,223,585 B2 | 5/2007 | Coffey |
| 7,235,084 B2 | 6/2007 | Skakoon |
| 7,235,393 B2 | 6/2007 | Gao |
| 7,238,526 B2 | 7/2007 | Wilson |
| 7,241,447 B1 | 7/2007 | Engelhardt |
| 7,247,472 B2 | 7/2007 | Wilson |
| 7,271,002 B2 | 9/2007 | Kotin |
| 7,282,199 B2 | 10/2007 | Gao |
| 7,291,498 B2 | 11/2007 | Roy |
| 7,300,797 B2 | 11/2007 | Van Agthoven |
| 7,306,794 B2 | 12/2007 | Wilson |
| 7,309,317 B2 | 12/2007 | Miller |
| 7,313,430 B2 | 12/2007 | Urquhart |
| 7,319,002 B2 | 1/2008 | Wilson |
| 7,322,954 B2 | 1/2008 | Putz |
| 7,326,555 B2 | 2/2008 | Konz |
| 7,343,205 B1 | 3/2008 | Pianca |
| 7,344,872 B2 | 3/2008 | Gao |
| 7,366,561 B2 | 4/2008 | Mills |
| 7,369,899 B2 | 5/2008 | Malinowski |
| 7,412,276 B2 | 8/2008 | Halperin |
| 7,419,817 B2 | 9/2008 | Chiorini |
| 7,419,956 B2 | 9/2008 | Ohtaki |
| 7,445,930 B2 | 11/2008 | Zhang |
| 7,465,292 B2 | 12/2008 | Putz |
| 7,466,303 B2 | 12/2008 | Yi |
| 7,479,554 B2 | 1/2009 | Chiorini |
| 7,491,508 B2 | 2/2009 | Roy |
| 7,505,807 B1 | 3/2009 | Kucharczyk |
| 7,510,872 B2 | 3/2009 | Clark |
| 7,510,875 B2 | 3/2009 | Zhang |
| 7,534,613 B2 | 5/2009 | Bankiewicz |
| 7,559,935 B2 | 7/2009 | Solar |
| 7,579,181 B2 | 8/2009 | ORiordan |
| 7,588,757 B2 | 9/2009 | Ozawa |
| 7,588,772 B2 | 9/2009 | Kay |
| 7,604,644 B2 | 10/2009 | Schulte |
| 7,608,064 B2 | 10/2009 | Putz |
| 7,625,347 B2 | 12/2009 | Burbank |
| 7,625,570 B1 | 12/2009 | Schaffer |
| 7,638,120 B2 | 12/2009 | Liu |
| 7,660,621 B2 | 2/2010 | Skakoon |
| 7,662,627 B2 | 2/2010 | Johnson |
| 7,695,480 B2 | 4/2010 | Solar |
| 7,704,492 B2 | 4/2010 | Podsakoff |
| 7,704,721 B2 | 4/2010 | Wright |
| 7,717,871 B2 | 5/2010 | Odland |
| 7,732,129 B1 | 6/2010 | Zhang |
| 7,780,679 B2 | 8/2010 | Bobo, Sr. |
| 7,790,449 B2 | 9/2010 | Gao |
| 7,803,622 B2 | 9/2010 | Engelhardt |
| 7,819,842 B2 | 10/2010 | Kaemmerer |
| 7,822,460 B2 | 10/2010 | Halperin |
| 7,837,668 B2 | 11/2010 | Gasmi |
| 7,838,277 B2 | 11/2010 | Gao |
| 7,842,055 B2 | 11/2010 | Pintor |
| 7,879,045 B2 | 2/2011 | Gielen |
| 7,888,096 B2 | 2/2011 | Wu |
| 7,901,921 B2 | 3/2011 | Coffey |
| 7,906,111 B2 | 3/2011 | Wilson |
| 7,925,328 B2 | 4/2011 | Urquhart |
| 7,968,333 B2 | 6/2011 | Yu |
| 7,976,530 B2 | 7/2011 | Johnson |
| 7,981,120 B2 | 7/2011 | Mazzocchi |
| 7,988,674 B2 | 8/2011 | Adams |
| RE42,856 E | 10/2011 | Karmarker et al. |
| 8,055,351 B2 | 11/2011 | Atalar |
| 8,092,429 B2 | 1/2012 | Gasmi |
| 8,099,150 B2 | 1/2012 | Piferi |
| 8,105,574 B2 | 1/2012 | Wilson |
| 8,108,028 B2 | 1/2012 | Karmarkar |
| 8,110,351 B2 | 2/2012 | Bosnes |
| 8,128,600 B2 | 3/2012 | Gill |
| 8,137,948 B2 | 3/2012 | Qu |
| 8,151,798 B2 | 4/2012 | Thomas |
| 8,157,828 B2 | 4/2012 | Piferi |
| 8,163,543 B2 | 4/2012 | Urabe |
| 8,175,677 B2 | 5/2012 | Sayler |
| 8,182,460 B2 | 5/2012 | Kaplitt |
| 8,195,272 B2 | 6/2012 | Piferi |
| 8,208,993 B2 | 6/2012 | Piferi |
| 8,231,880 B2 | 7/2012 | Roy |
| 8,236,495 B2 | 8/2012 | Nochumson |
| 8,241,622 B2 | 8/2012 | Englehardt |
| 8,273,344 B2 | 9/2012 | Wang |
| 8,283,151 B2 | 10/2012 | Schmidt |
| 8,309,355 B2 | 11/2012 | Bankiewicz |
| 8,315,689 B2 | 11/2012 | Jenkins |
| 8,318,480 B2 | 11/2012 | Gao |
| 8,318,687 B2 | 11/2012 | Tabira |
| 8,320,990 B2 | 11/2012 | Kamal |
| 8,340,743 B2 | 12/2012 | Jenkins |
| 8,357,175 B2 | 1/2013 | Mark |
| 8,369,930 B2 | 2/2013 | Jenkins |
| 8,374,677 B2 | 2/2013 | Piferi |
| 8,380,277 B2 | 2/2013 | Atalar |
| 8,394,386 B2 | 3/2013 | Wilson |
| 8,396,532 B2 | 3/2013 | Jenkins |
| 8,409,842 B2 | 4/2013 | Clark |
| 8,430,888 B2 | 4/2013 | Malinowski |
| 8,433,421 B2 | 4/2013 | Atalar |
| 8,460,328 B2 | 6/2013 | Piferi |
| 8,467,852 B2 | 6/2013 | Csavoy |
| 8,470,310 B2 | 6/2013 | Roy |
| 8,475,468 B2 | 7/2013 | Leckrone |
| 8,476,418 B2 | 7/2013 | Mueller |
| 8,480,626 B2 | 7/2013 | Nelson |
| 8,509,876 B2 | 8/2013 | Karmarkar |
| 8,512,981 B2 | 8/2013 | Hermens |
| 8,524,219 B2 | 9/2013 | Roy |
| 8,524,446 B2 | 9/2013 | Gao |
| 8,548,569 B2 | 10/2013 | Piferi |
| 8,591,522 B2 | 11/2013 | Solar |
| 8,600,479 B2 | 12/2013 | Dalke |
| 8,603,459 B2 | 12/2013 | Wilson |
| 8,614,101 B2 | 12/2013 | VanDine |
| 8,617,180 B2 | 12/2013 | Thiran |
| RE44,736 E | 1/2014 | Karmarker et al. |
| 8,637,255 B2 | 1/2014 | Wilson |
| 8,642,314 B2 | 2/2014 | Bakker |
| 8,644,906 B2 | 2/2014 | Piferi |
| 8,649,842 B2 | 2/2014 | Atalar |
| 8,685,734 B2 | 4/2014 | Coffey |
| 8,688,226 B2 | 4/2014 | Atalar |
| 8,688,238 B2 | 4/2014 | Gerber |
| 8,697,417 B2 | 4/2014 | Bakker |
| 8,697,665 B2 | 4/2014 | Rom |
| 8,706,194 B2 | 4/2014 | Wurmfeld |
| 8,747,419 B2 | 6/2014 | Solar |
| 8,753,314 B2 | 6/2014 | Mendez |
| 8,768,433 B2 | 7/2014 | Jenkins |
| 8,788,043 B2 | 7/2014 | Malinowski |
| 8,801,629 B2 | 8/2014 | Tu |
| 8,825,133 B2 | 9/2014 | Jenkins |
| 8,834,863 B2 | 9/2014 | Roy |

(56) References Cited

U.S. PATENT DOCUMENTS

| | | |
|---|---|---|
| 8,845,655 B2 | 9/2014 | Henderson |
| 8,845,656 B2 | 9/2014 | Skakoon |
| 8,846,030 B2 | 9/2014 | Engelhardt |
| 8,846,389 B2 | 9/2014 | Chiorini |
| 8,864,790 B2 | 10/2014 | Strauss |
| 8,870,892 B2 | 10/2014 | Feng |
| 8,886,288 B2 | 11/2014 | Jenkins |
| 8,886,331 B2 | 11/2014 | Labadie |
| 8,906,387 B2 | 12/2014 | Kay |
| 8,906,675 B2 | 12/2014 | Gao |
| 8,909,320 B2 | 12/2014 | Jenkins |
| 8,927,514 B2 | 1/2015 | Chatterjee |
| 8,945,089 B2 | 2/2015 | Johnson |
| 8,961,535 B2 | 2/2015 | Burg |
| 8,962,330 B2 | 2/2015 | Gao |
| 8,962,332 B2 | 2/2015 | Gao |
| 8,979,871 B2 | 3/2015 | Tyc |
| 8,992,458 B2 | 3/2015 | Singh |
| 8,999,678 B2 | 4/2015 | Vandenberghe |
| 9,031,636 B2 | 5/2015 | Piferi |
| 9,039,615 B2 | 5/2015 | Flint |
| 9,042,958 B2 | 5/2015 | Karmarkar |
| 9,050,299 B2 | 6/2015 | Bankiewicz |
| 9,051,542 B2 | 6/2015 | Wright |
| 9,055,884 B2 | 6/2015 | Piferi |
| 9,056,185 B2 | 6/2015 | Fischell |
| 9,056,892 B2 | 6/2015 | Pun |
| 9,067,028 B2 | 6/2015 | Mendez |
| 9,072,863 B2 | 7/2015 | Bennett |
| 9,078,588 B2 | 7/2015 | Ghidoli |
| 9,080,183 B2 | 7/2015 | Klein |
| 9,089,667 B2 | 7/2015 | Bankiewicz |
| 9,097,756 B2 | 8/2015 | Piferi |
| 9,102,943 B2 | 8/2015 | Shinmura |
| 9,102,949 B2 | 8/2015 | Gao |
| 9,113,949 B2 | 8/2015 | Nelson |
| 9,115,373 B2 | 8/2015 | Hermens |
| 9,125,676 B2 | 9/2015 | Sahni |
| 9,163,260 B2 | 10/2015 | Wilson |
| 9,179,857 B2 | 11/2015 | Lee |
| 9,192,393 B2 | 11/2015 | Piferi |
| 9,192,446 B2 | 11/2015 | Piferi |
| 9,198,687 B2 | 12/2015 | Fulkerson |
| 9,211,157 B2 | 12/2015 | Tyc |
| 9,217,155 B2 | 12/2015 | Gao |
| 9,217,159 B2 | 12/2015 | Roy |
| 9,228,174 B2 | 1/2016 | Noordman |
| 9,232,977 B1 | 1/2016 | Rehman |
| 9,233,174 B2 | 1/2016 | Chen |
| 9,238,800 B2 | 1/2016 | Bossis |
| 9,242,090 B2 | 1/2016 | Atalar |
| 9,247,895 B2 | 2/2016 | Venkatesan |
| 9,248,256 B2 | 2/2016 | Takagi |
| 9,248,270 B2 | 2/2016 | Karmarkar |
| 9,259,290 B2 | 2/2016 | Jenkins |
| 9,260,724 B2 | 2/2016 | Bakker |
| 9,283,357 B2 | 3/2016 | Stedman |
| 9,289,270 B2 | 3/2016 | Gielen |
| 9,291,692 B2 | 3/2016 | Yang |
| 9,302,070 B2 | 4/2016 | Bankiewicz |
| 9,314,305 B2 | 4/2016 | Jenkins |
| 9,327,096 B2 | 5/2016 | Herweck |
| 9,345,499 B2 | 5/2016 | Strauss |
| 9,345,875 B2 | 5/2016 | Appenrodt |
| 9,408,629 B2 | 8/2016 | Flint |
| 9,439,979 B2 | 9/2016 | Chiorini |
| 9,441,206 B2 | 9/2016 | Grieger |
| 9,441,244 B2 | 9/2016 | Schaffer |
| 9,445,793 B2 | 9/2016 | Solar |
| 9,447,433 B2 | 9/2016 | Hirsch |
| 9,452,241 B2 | 9/2016 | Gill |
| 9,457,103 B2 | 10/2016 | Schaffer |
| 9,458,517 B2 | 10/2016 | Schaffer |
| 9,464,119 B2 | 10/2016 | Sonntag |
| 9,475,845 B2 | 10/2016 | Asokan |
| 9,486,170 B2 | 11/2016 | Andrews |
| 9,492,121 B2 | 11/2016 | Andrews |
| 9,492,415 B2 | 11/2016 | Bankiewicz |
| 9,493,788 B2 | 11/2016 | Gao |
| 9,498,248 B2 | 11/2016 | Nelson |
| 9,498,290 B2 | 11/2016 | Piferi |
| 9,498,575 B2 | 11/2016 | Flores |
| 9,506,083 B2 | 11/2016 | Arbetman |
| 9,510,909 B2 | 12/2016 | Grant |
| 9,528,126 B2 | 12/2016 | Qu |
| 9,540,659 B2 | 1/2017 | Davidson |
| 9,546,112 B2 | 1/2017 | Voit |
| 9,546,369 B2 | 1/2017 | Gao |
| 9,567,376 B2 | 2/2017 | Cronin |
| 9,567,607 B2 | 2/2017 | Wilson |
| 9,572,928 B2 | 2/2017 | Shifflette |
| 9,579,368 B2 | 2/2017 | Bratbak |
| 9,580,691 B2 | 2/2017 | Bakker |
| 9,585,971 B2 | 3/2017 | Deverman |
| 9,587,250 B2 | 3/2017 | Gao |
| 9,587,282 B2 | 3/2017 | Schaffer |
| 9,593,346 B2 | 3/2017 | Roy |
| 9,596,835 B2 | 3/2017 | Gao |
| 9,597,363 B2 | 3/2017 | Roy |
| 9,598,468 B2 | 3/2017 | Weigel-Van Aken |
| 9,598,703 B2 | 3/2017 | Garcia |
| 9,611,302 B2 | 4/2017 | Srivastava |
| 9,617,561 B2 | 4/2017 | Roy |
| 9,623,120 B2 | 4/2017 | Chatterjee |
| 9,624,274 B2 | 4/2017 | Lux |
| 9,629,658 B2 | 4/2017 | Barker |
| 9,636,370 B2 | 5/2017 | McCown |
| 9,643,325 B2 | 5/2017 | Berkelman |
| 9,649,161 B2 | 5/2017 | Lee |
| 9,649,162 B2 | 5/2017 | Lee |
| 9,662,472 B2 | 5/2017 | Cunningham |
| 9,669,188 B2 | 6/2017 | Echarri |
| 9,669,198 B2 | 6/2017 | Broaddus |
| 9,670,507 B2 | 6/2017 | Xiao |
| 9,675,783 B2 | 6/2017 | Asaad |
| 9,677,088 B2 | 6/2017 | Nakai |
| 9,677,089 B2 | 6/2017 | Gao |
| 9,682,193 B2 | 6/2017 | Anand |
| 9,700,342 B2 | 7/2017 | Andrews |
| 9,700,350 B2 | 7/2017 | Barker |
| 9,750,623 B2 | 9/2017 | Wainwright |
| 9,763,745 B2 | 9/2017 | Karmarkar |
| 9,820,723 B2 | 11/2017 | Lee |
| 9,827,046 B2 | 11/2017 | Rurling |
| 9,849,266 B2 | 12/2017 | Thomson |
| 9,891,296 B2 | 2/2018 | Piferi |
| 9,901,400 B2 | 2/2018 | Gowda |
| 10,065,021 B2 | 9/2018 | Grahn |
| 10,076,387 B2 | 9/2018 | Nelson |
| 10,092,367 B2 | 10/2018 | Andrews |
| 10,099,034 B2 | 10/2018 | Lim |
| 10,105,485 B2 | 10/2018 | Piferi |
| 10,105,518 B2 | 10/2018 | Hansen |
| 10,118,004 B2 | 11/2018 | Fischell |
| 10,130,440 B2 | 11/2018 | Gowda |
| 10,130,789 B2 | 11/2018 | Shimada |
| 10,159,782 B2 | 12/2018 | Elias |
| 10,182,879 B2 | 1/2019 | Piecuch |
| 10,188,462 B2 | 1/2019 | Tyc |
| 10,194,890 B2 | 2/2019 | Cosgrove |
| 10,206,693 B2 | 2/2019 | Piferi |
| 10,207,080 B2 | 2/2019 | Lee |
| 10,208,318 B2 | 2/2019 | Barkats |
| 10,214,572 B2 | 2/2019 | Boye |
| 10,219,873 B2 | 3/2019 | Gowda |
| 10,226,616 B2 | 3/2019 | Barker |
| 10,245,388 B2 | 4/2019 | Cabrera Aquino |
| 10,245,413 B2 | 4/2019 | Shimada |
| 10,300,268 B2 | 5/2019 | Skakoon |
| 10,307,220 B2 | 6/2019 | Piferi |
| 10,342,632 B2 | 7/2019 | Andrews |
| 10,357,281 B2 | 7/2019 | Piferi |
| 10,357,631 B2 | 7/2019 | Jackson |
| 10,357,632 B2 | 7/2019 | Herweck |

(56) References Cited

U.S. PATENT DOCUMENTS

| | | | |
|---|---|---|---|
| 10,376,327 B2 | 8/2019 | Jenkins |
| 10,376,333 B2 | 8/2019 | Piferi |
| 10,426,374 B2 | 10/2019 | Bankiewicz |
| 10,426,375 B2 | 10/2019 | Bankiewicz |
| 10,456,201 B1 | 10/2019 | Solar |
| 10,456,212 B2 | 10/2019 | Gonzalez-Martinez |
| 10,456,555 B2 | 10/2019 | Garrison |
| 10,478,535 B2 | 11/2019 | Ogle |
| 10,485,952 B2 | 11/2019 | Garrison |
| 10,492,881 B2 | 12/2019 | Karmarkar |
| 10,531,882 B2 | 1/2020 | Anand |
| 10,548,630 B2 | 2/2020 | Swaney |
| 10,561,527 B2 | 2/2020 | Rozenberg |
| 10,569,013 B2 | 2/2020 | Piferi |
| 10,576,246 B2 | 3/2020 | Fischell |
| 10,576,247 B2 | 3/2020 | Flores |
| 10,595,744 B2 | 3/2020 | Sayler |
| 10,596,353 B2 | 3/2020 | Flores |
| 10,610,207 B2 | 4/2020 | Pretre |
| 10,625,045 B2 | 4/2020 | Mcneese |
| 10,716,593 B2 | 7/2020 | Chieng |
| 10,716,834 B2 | 7/2020 | Bratbak |
| 10,722,265 B1 | 7/2020 | Davis |
| 10,751,137 B2 | 8/2020 | Zastrozna |
| 10,751,513 B2 | 8/2020 | Gill |
| 10,758,264 B2 | 9/2020 | Bankiewicz |
| 2001/0006955 A1 | 7/2001 | Wilson |
| 2001/0014771 A1 | 8/2001 | Truwit |
| 2001/0049144 A1 | 12/2001 | Rivera |
| 2002/0019050 A1 | 2/2002 | Gao |
| 2002/0019641 A1 | 2/2002 | Truwit |
| 2002/0037867 A1 | 3/2002 | Wilson |
| 2002/0052610 A1* | 5/2002 | Skakoon | A61N 1/0534 606/129 |
| 2002/0081721 A1 | 6/2002 | Allen |
| 2002/0090717 A1 | 7/2002 | Gao |
| 2002/0102714 A1 | 8/2002 | Wilson |
| 2002/0131961 A1 | 9/2002 | Wilson |
| 2003/0013189 A1 | 1/2003 | Wilson |
| 2003/0023230 A1 | 1/2003 | Lewis |
| 2003/0032613 A1 | 2/2003 | Gao |
| 2003/0040753 A1 | 2/2003 | Daum |
| 2003/0073934 A1 | 4/2003 | Putz |
| 2003/0092161 A1 | 5/2003 | Gao |
| 2003/0093105 A1 | 5/2003 | Huffmaster |
| 2003/0096264 A1 | 5/2003 | Altar |
| 2003/0100115 A1 | 5/2003 | Raj |
| 2003/0114876 A1 | 6/2003 | Samset |
| 2003/0119191 A1 | 6/2003 | Gao |
| 2003/0138772 A1 | 7/2003 | Gao |
| 2003/0199831 A1 | 10/2003 | Morris |
| 2004/0006302 A1 | 1/2004 | Chaouk |
| 2004/0024308 A1 | 2/2004 | Wickline |
| 2004/0043490 A1 | 3/2004 | Shimada |
| 2004/0049121 A1 | 3/2004 | Yaron |
| 2004/0057931 A1 | 3/2004 | Wilson |
| 2004/0059260 A1 | 3/2004 | Truwit |
| 2004/0136963 A1 | 7/2004 | Wilson |
| 2004/0167391 A1 | 8/2004 | Solar |
| 2004/0171807 A1 | 9/2004 | Gao |
| 2004/0215143 A1 | 10/2004 | Brady |
| 2005/0261218 A1 | 11/2005 | Esau |
| 2005/0288631 A1 | 12/2005 | Lewis |
| 2006/0003451 A1 | 1/2006 | Gao |
| 2006/0058743 A1 | 3/2006 | Putz |
| 2006/0100501 A1 | 5/2006 | Berkelman |
| 2006/0122630 A1 | 6/2006 | Daum |
| 2006/0129126 A1 | 6/2006 | Kaplitt |
| 2006/0142783 A1 | 6/2006 | Lewis |
| 2006/0204479 A1 | 9/2006 | Wilson |
| 2007/0004042 A1 | 1/2007 | Gao |
| 2007/0106305 A1 | 5/2007 | Kao et al. |
| 2008/0008684 A1 | 1/2008 | Wilson |
| 2008/0009784 A1 | 1/2008 | Leedle |
| 2008/0015639 A1 | 1/2008 | Bjork |
| 2008/0050343 A1 | 2/2008 | Wilson |
| 2008/0050345 A1 | 2/2008 | Wilson |
| 2008/0065002 A1 | 3/2008 | Lobl |
| 2008/0065104 A1 | 3/2008 | Larkin |
| 2008/0075737 A1 | 3/2008 | Gao |
| 2008/0103456 A1 | 5/2008 | Johnson |
| 2008/0171930 A1 | 7/2008 | Abolfathi |
| 2008/0249501 A1 | 10/2008 | Yamasaki |
| 2008/0275466 A1 | 11/2008 | Skakoon |
| 2009/0048610 A1 | 2/2009 | Tolkowsky |
| 2009/0112084 A1 | 4/2009 | Piferi |
| 2009/0118610 A1 | 5/2009 | Karmarkar |
| 2009/0215871 A1 | 8/2009 | Wilson |
| 2009/0275107 A1 | 11/2009 | Lock |
| 2009/0317417 A1 | 12/2009 | Vandenberghe |
| 2010/0030219 A1 | 2/2010 | Lerner |
| 2010/0113919 A1 | 5/2010 | Maschke |
| 2010/0198052 A1 | 8/2010 | Jenkins |
| 2010/0204684 A1 | 8/2010 | Garrison |
| 2010/0217231 A1 | 8/2010 | Ilan |
| 2010/0217236 A1 | 8/2010 | Gill |
| 2010/0222668 A1 | 9/2010 | Dalke |
| 2010/0247490 A1 | 9/2010 | Roy |
| 2010/0278791 A1 | 11/2010 | Wilson |
| 2010/0318061 A1 | 12/2010 | Derrick |
| 2010/0318064 A1 | 12/2010 | Derrick |
| 2010/0331882 A1 | 12/2010 | Bjork |
| 2011/0009879 A1 | 1/2011 | Derrick |
| 2011/0136227 A1 | 6/2011 | Bakker |
| 2011/0171262 A1 | 7/2011 | Bakker |
| 2011/0206616 A1 | 8/2011 | Ichtchenko |
| 2011/0223135 A1 | 9/2011 | Roy |
| 2011/0224478 A1 | 9/2011 | Hannoun-Levi |
| 2011/0229971 A1 | 9/2011 | Knop |
| 2011/0263001 A1 | 10/2011 | Lakshmipathy |
| 2012/0041411 A1 | 2/2012 | Horton |
| 2012/0046349 A1 | 2/2012 | Bell |
| 2012/0058102 A1 | 3/2012 | Wilson |
| 2012/0064115 A1 | 3/2012 | John |
| 2012/0078087 A1 | 3/2012 | Curry |
| 2012/0093853 A1 | 4/2012 | Wilson |
| 2012/0123391 A1 | 5/2012 | Gill |
| 2012/0137379 A1 | 5/2012 | Gao |
| 2012/0203236 A1 | 8/2012 | Mamourian |
| 2012/0209110 A1 | 8/2012 | Bankiewicz |
| 2012/0220648 A1 | 8/2012 | Hwu |
| 2012/0258046 A1 | 10/2012 | Mutzke |
| 2012/0295960 A1 | 11/2012 | Palfi |
| 2013/0018307 A1 | 1/2013 | Lee |
| 2013/0023033 A1 | 1/2013 | Wilson |
| 2013/0045186 A1 | 2/2013 | Gao |
| 2013/0053792 A1 | 2/2013 | Fischell |
| 2013/0066266 A1 | 3/2013 | Cunningham |
| 2013/0096570 A1* | 4/2013 | Solar | A61B 90/11 606/108 |
| 2013/0101558 A1 | 4/2013 | Gao |
| 2013/0116721 A1 | 5/2013 | Takagi |
| 2013/0137977 A1 | 5/2013 | Eder |
| 2013/0150701 A1 | 6/2013 | Budar |
| 2013/0158578 A1 | 6/2013 | Ghodke |
| 2013/0195801 A1 | 8/2013 | Gao |
| 2013/0211249 A1 | 8/2013 | Barnett |
| 2013/0211316 A1 | 8/2013 | Wilcox |
| 2013/0211424 A1 | 8/2013 | Thiran |
| 2013/0231683 A1 | 9/2013 | Kao |
| 2013/0267902 A1 | 10/2013 | Seaver |
| 2013/0274778 A1 | 10/2013 | Mercier |
| 2013/0296532 A1 | 11/2013 | Hermens |
| 2013/0317521 A1 | 11/2013 | Choi |
| 2013/0323226 A1 | 12/2013 | Wilson |
| 2013/0323302 A1 | 12/2013 | Constable |
| 2013/0324834 A1 | 12/2013 | Majewski |
| 2014/0024909 A1 | 1/2014 | Vij |
| 2014/0031418 A1 | 1/2014 | Wilson |
| 2014/0044680 A1 | 2/2014 | Roy |
| 2014/0065105 A1 | 3/2014 | Wilson |
| 2014/0087361 A1 | 3/2014 | Dobbelaer |
| 2014/0094823 A1 | 4/2014 | Carcieri |
| 2014/0099666 A1 | 4/2014 | Rossomando |

(56) References Cited

U.S. PATENT DOCUMENTS

| | | |
|---|---|---|
| 2014/0107186 A1 | 4/2014 | Garcia |
| 2014/0243783 A1 | 8/2014 | Raghavan |
| 2014/0330211 A1 | 11/2014 | Kassab |
| 2014/0336245 A1 | 11/2014 | Mingozzi |
| 2014/0341852 A1 | 11/2014 | Srivastava |
| 2014/0342434 A1 | 11/2014 | Hermens |
| 2015/0005369 A1 | 1/2015 | Muzyczka |
| 2015/0011938 A1 | 1/2015 | Gill |
| 2015/0023924 A1 | 1/2015 | High |
| 2015/0065562 A1 | 3/2015 | Yazicioglu |
| 2015/0087961 A1 | 3/2015 | Tyc |
| 2015/0087962 A1 | 3/2015 | Tyc |
| 2015/0100064 A1 | 4/2015 | Skakoon |
| 2015/0118287 A1 | 4/2015 | Hammond |
| 2015/0139952 A1 | 5/2015 | Webster |
| 2015/0159173 A1 | 6/2015 | Vandenberghe |
| 2015/0184197 A1 | 7/2015 | Davidson |
| 2015/0196671 A1 | 7/2015 | Byrne |
| 2015/0230871 A1 | 8/2015 | Sayler |
| 2015/0238610 A1 | 8/2015 | Sista |
| 2015/0307898 A2 | 10/2015 | Hermens |
| 2015/0315610 A1 | 11/2015 | Nishie |
| 2015/0374803 A1 | 12/2015 | Wolfe |
| 2016/0022171 A1 | 1/2016 | Lin |
| 2016/0032319 A1 | 2/2016 | Wright |
| 2016/0051801 A1 | 2/2016 | Vase |
| 2016/0106508 A1 | 4/2016 | Lathrop |
| 2016/0108373 A1 | 4/2016 | Bennett |
| 2016/0153992 A1 | 6/2016 | Buening |
| 2016/0166709 A1 | 6/2016 | Davidson |
| 2016/0199146 A1 | 7/2016 | Tai |
| 2016/0213312 A1 | 7/2016 | Singh |
| 2016/0220789 A1 | 8/2016 | Eldredge |
| 2016/0256534 A1 | 9/2016 | Bankiewicz |
| 2016/0271192 A1 | 9/2016 | Roy |
| 2016/0273058 A1 | 9/2016 | Akashika |
| 2016/0289275 A1 | 10/2016 | Chiorini |
| 2016/0296694 A1 | 10/2016 | Bankiewicz |
| 2016/0317077 A1 | 11/2016 | Sillay |
| 2016/0331897 A1 | 11/2016 | Anand |
| 2016/0333372 A1 | 11/2016 | Srivastava |
| 2016/0333373 A1 | 11/2016 | Farley |
| 2016/0333375 A1 | 11/2016 | Chen |
| 2016/0339206 A1 | 11/2016 | Cunningham |
| 2016/0340393 A1 | 11/2016 | Schaffer |
| 2016/0340692 A1 | 11/2016 | Wang |
| 2016/0346505 A1 | 12/2016 | Gill |
| 2016/0354163 A1 | 12/2016 | Andrews |
| 2016/0361439 A1 | 12/2016 | Agbandje-McKenna |
| 2016/0369297 A1 | 12/2016 | Byrne |
| 2016/0369298 A1 | 12/2016 | Marsic |
| 2016/0369299 A1 | 12/2016 | Boye |
| 2016/0375151 A1 | 12/2016 | Schaffer |
| 2016/0375221 A1 | 12/2016 | Panotopoulos |
| 2016/0376323 A1 | 12/2016 | Schaffer |
| 2016/0376608 A1 | 12/2016 | Chou |
| 2017/0000904 A1 | 1/2017 | Wilson |
| 2017/0007669 A1 | 1/2017 | Sarkar |
| 2017/0007720 A1 | 1/2017 | Boye |
| 2017/0028082 A1 | 2/2017 | Wilson |
| 2017/0035525 A1 | 2/2017 | Baumgartner |
| 2017/0044504 A1 | 2/2017 | Schaffer |
| 2017/0065835 A1 | 3/2017 | Park |
| 2017/0067028 A1 | 3/2017 | Ballon |
| 2017/0071972 A1 | 3/2017 | Buj Bello |
| 2017/0073703 A1 | 3/2017 | Chatterjee |
| 2017/0088858 A1 | 3/2017 | Gao |
| 2017/0096646 A1 | 4/2017 | Roy |
| 2017/0105927 A1 | 4/2017 | Thorne |
| 2017/0112946 A1 | 4/2017 | Ikeda |
| 2017/0121734 A1 | 5/2017 | Cairns |
| 2017/0128581 A1 | 5/2017 | Freskgard |
| 2017/0128594 A1 | 5/2017 | Wright |
| 2017/0130208 A1 | 5/2017 | Potter |
| 2017/0130245 A1 | 5/2017 | Kotin |
| 2017/0135778 A1 | 5/2017 | Gill |
| 2017/0145440 A1 | 5/2017 | Hermens |
| 2017/0151348 A1 | 6/2017 | Kaspar |
| 2017/0151416 A1 | 6/2017 | Kutikov |
| 2017/0152525 A1 | 6/2017 | Hermens |
| 2017/0157267 A1 | 6/2017 | Kay |
| 2017/0159026 A1 | 6/2017 | Kay |
| 2017/0159027 A1 | 6/2017 | Wilson |
| 2017/0159072 A9 | 6/2017 | Arbeit |
| 2017/0165377 A1 | 6/2017 | Gao |
| 2017/0166871 A1 | 6/2017 | Nishie |
| 2017/0166925 A1 | 6/2017 | Gao |
| 2017/0166926 A1 | 6/2017 | Deverman |
| 2017/0166927 A1 | 6/2017 | Gao |
| 2017/0211092 A1 | 7/2017 | Chatterjee |
| 2017/0211093 A1 | 7/2017 | Chatterjee |
| 2017/0211094 A1 | 7/2017 | Chatterjee |
| 2017/0232117 A1 | 8/2017 | Arbetman |
| 2017/0246322 A1 | 8/2017 | Mendell |
| 2017/0258489 A1 | 9/2017 | Galili |
| 2017/0258996 A1 | 9/2017 | Anand |
| 2017/0290637 A1 | 10/2017 | Diez |
| 2017/0333060 A1 | 11/2017 | Panian |
| 2018/0028746 A1 | 2/2018 | Abrams |
| 2018/0098778 A1 | 4/2018 | Ogle |
| 2018/0110568 A1 | 4/2018 | Lenarz |
| 2018/0140810 A1 | 5/2018 | Cataltepe |
| 2018/0193042 A1 | 7/2018 | Wilson |
| 2018/0207399 A1 | 7/2018 | Chou |
| 2018/0303560 A1 | 10/2018 | Pandey |
| 2018/0339065 A1 | 11/2018 | Wilson |
| 2018/0344199 A1 | 12/2018 | Bankiewicz |
| 2018/0361114 A1 | 12/2018 | Chou |
| 2018/0369555 A1 | 12/2018 | Woolley |
| 2019/0000940 A1 | 1/2019 | Kotin |
| 2019/0000991 A1 | 1/2019 | Pykett |
| 2019/0008919 A1 | 1/2019 | Kassab |
| 2019/0008933 A1 | 1/2019 | Kotin |
| 2019/0030281 A1 | 1/2019 | Lim |
| 2019/0038773 A1 | 2/2019 | Esteves |
| 2019/0038777 A1 | 2/2019 | Donsante |
| 2019/0070356 A1 | 3/2019 | Elias |
| 2019/0070387 A1 | 3/2019 | Goyal |
| 2019/0083302 A1 | 3/2019 | Khanna |
| 2019/0083303 A1 | 3/2019 | Khanna |
| 2019/0143099 A1 | 5/2019 | Barker |
| 2019/0160254 A1 | 5/2019 | Anand |
| 2019/0167864 A1 | 6/2019 | Kassab |
| 2019/0167918 A1 | 6/2019 | Fischell |
| 2019/0183517 A1 | 6/2019 | Ogle |
| 2019/0192040 A1 | 6/2019 | Bankiewicz |
| 2019/0216575 A1 | 7/2019 | Farah |
| 2019/0223972 A1 | 7/2019 | Fischer |
| 2019/0314110 A1 | 10/2019 | Piferi |
| 2019/0314616 A1 | 10/2019 | Moll |
| 2019/0336232 A1 | 11/2019 | Jenkins |
| 2019/0343552 A1 | 11/2019 | Yaffe |
| 2019/0346516 A1 | 11/2019 | Piferi |
| 2019/0350666 A1 | 11/2019 | Grunert |
| 2019/0351182 A1 | 11/2019 | Chou |
| 2019/0366043 A1 | 12/2019 | Garrison |
| 2020/0016369 A1 | 1/2020 | Garrison |
| 2020/0023160 A1 | 1/2020 | Chou |
| 2020/0046249 A1 | 2/2020 | Randell |
| 2020/0069215 A1 | 3/2020 | Bankiewicz |
| 2020/0078131 A1 | 3/2020 | Karmarkar |
| 2020/0085512 A1 | 3/2020 | Reimer |
| 2020/0086083 A1 | 3/2020 | Porter |
| 2020/0101239 A1 | 4/2020 | Singh |
| 2020/0101275 A1 | 4/2020 | Singh |
| 2020/0147299 A1 | 5/2020 | Piferi |
| 2020/0147344 A1 | 5/2020 | Flores |
| 2020/0164178 A1 | 5/2020 | Garrison |
| 2020/0170539 A1 | 6/2020 | Sayler |
| 2020/0170748 A1 | 6/2020 | Folzenlogen |
| 2020/0214726 A1 | 7/2020 | Anand |
| 2020/0215306 A1 | 7/2020 | Garrison |
| 2020/0222079 A1 | 7/2020 | Swaney |
| 2020/0229889 A1 | 7/2020 | Kells |

(56) References Cited

U.S. PATENT DOCUMENTS

| | | |
|---|---|---|
| 2020/0246099 A1 | 8/2020 | Jones |
| 2020/0246100 A1 | 8/2020 | Jones |
| 2020/0246101 A1 | 8/2020 | Jones |
| 2020/0269015 A1 | 8/2020 | Fischell |

FOREIGN PATENT DOCUMENTS

| | | |
|---|---|---|
| CA | 2289449 C | 11/1998 |
| CA | 2289837 A1 | 11/1998 |
| CA | 2686281 | 11/1998 |
| CA | 2344641 A1 | 3/2000 |
| CA | 2346613 C | 4/2000 |
| CA | 2343554 A1 | 10/2001 |
| CA | 2282007 C | 5/2002 |
| CA | 2452379 A1 | 1/2003 |
| CA | 2467406 C | 5/2003 |
| CA | 2475855 C | 9/2003 |
| CA | 2872998 | 9/2003 |
| CA | 2974428 | 9/2003 |
| CA | 2499573 A1 | 4/2004 |
| CA | 2510918 A1 | 7/2004 |
| CA | 2511469 A1 | 7/2004 |
| CA | 2511472 | 7/2004 |
| CA | 2575313 | 2/2006 |
| CA | 2576306 | 3/2006 |
| CA | 2581714 | 4/2006 |
| CA | 2619882 | 3/2007 |
| CA | 2621447 | 3/2007 |
| CA | 2623616 | 6/2007 |
| CA | 2642798 | 7/2007 |
| CA | 2644777 | 9/2007 |
| CA | 2672147 | 1/2008 |
| CA | 2660727 | 3/2008 |
| CA | 2666248 | 4/2008 |
| CA | 2721367 | 4/2008 |
| CA | 2674222 | 7/2008 |
| CA | 2687282 | 11/2008 |
| CA | 2688825 | 11/2008 |
| CA | 2695494 | 12/2008 |
| CA | 2700523 | 4/2009 |
| CA | 2700529 | 4/2009 |
| CA | 2700577 | 4/2009 |
| CA | 2700607 | 4/2009 |
| CA | 2701132 | 4/2009 |
| CA | 2701744 | 4/2009 |
| CA | 2704739 | 4/2009 |
| CA | 2704582 | 5/2009 |
| CA | 2726619 | 12/2009 |
| CA | 2739173 | 4/2010 |
| CA | 2771175 | 3/2011 |
| CA | 2796951 | 10/2011 |
| CA | 2802291 | 1/2012 |
| CA | 2774733 | 10/2012 |
| CA | 2838508 | 12/2012 |
| CA | 2860026 | 6/2013 |
| CA | 2864624 | 9/2013 |
| CA | 2878510 | 1/2014 |
| CA | 2879770 | 1/2014 |
| CA | 2883893 | 3/2014 |
| CA | 2884136 | 3/2014 |
| CA | 2895509 | 6/2014 |
| CA | 2844980 | 9/2014 |
| CA | 2915505 | 12/2014 |
| CA | 2920014 | 2/2015 |
| CA | 2920394 | 3/2015 |
| CA | 2921133 | 3/2015 |
| CA | 2937839 | 7/2015 |
| CA | 2966029 | 5/2016 |
| CA | 2983072 | 8/2016 |
| CA | 2987931 | 12/2016 |
| CA | 3008680 | 7/2017 |
| CA | 3016336 | 9/2017 |
| CA | 3035522 | 3/2018 |
| CA | 3070087 | 1/2019 |
| CA | 3078990 | 5/2019 |
| EP | 1015059 | 7/2000 |
| EP | 1015619 A1 | 7/2000 |
| EP | 1018963 | 7/2000 |
| EP | 1046711 | 10/2000 |
| EP | 1078096 A1 | 2/2001 |
| EP | 1121061 | 8/2001 |
| EP | 862388 | 11/2001 |
| EP | 783279 | 12/2001 |
| EP | 1164195 | 12/2001 |
| EP | 1183380 A1 | 3/2002 |
| EP | 1218035 | 7/2002 |
| EP | 1240345 | 9/2002 |
| EP | 1272120 | 1/2003 |
| EP | 1279740 | 1/2003 |
| EP | 1444001 | 8/2004 |
| EP | 1453547 | 9/2004 |
| EP | 1482851 | 12/2004 |
| EP | 1621625 | 2/2006 |
| EP | 1677696 | 7/2006 |
| EP | 1696036 | 8/2006 |
| EP | 1795143 | 6/2007 |
| EP | 1847614 | 10/2007 |
| EP | 1849872 | 10/2007 |
| EP | 1857552 | 11/2007 |
| EP | 1944043 | 7/2008 |
| EP | 2007795 | 12/2008 |
| EP | 2066364 | 6/2009 |
| EP | 2139418 | 1/2010 |
| EP | 2152346 | 2/2010 |
| EP | 2195676 | 6/2010 |
| EP | 2198016 | 6/2010 |
| EP | 2220241 | 8/2010 |
| EP | 2220242 | 8/2010 |
| EP | 2237826 | 10/2010 |
| EP | 2292779 | 3/2011 |
| EP | 2325298 | 5/2011 |
| EP | 2359866 | 8/2011 |
| EP | 2383346 | 11/2011 |
| EP | 2442718 | 4/2012 |
| EP | 2146768 | 8/2012 |
| EP | 2510971 | 10/2012 |
| EP | 2523599 | 11/2012 |
| EP | 2524037 | 11/2012 |
| EP | 2527457 B1 | 11/2012 |
| EP | 2531604 | 12/2012 |
| EP | 2558154 | 2/2013 |
| EP | 2560721 | 2/2013 |
| EP | 2572661 | 3/2013 |
| EP | 2601997 | 6/2013 |
| EP | 2091459 | 9/2013 |
| EP | 2660325 | 11/2013 |
| EP | 2104530 | 2/2014 |
| EP | 2699270 | 2/2014 |
| EP | 2717955 | 4/2014 |
| EP | 2737071 | 6/2014 |
| EP | 1807009 | 11/2014 |
| EP | 2814958 | 12/2014 |
| EP | 2819739 | 1/2015 |
| EP | 2871239 | 5/2015 |
| EP | 2879719 | 6/2015 |
| EP | 2933336 | 10/2015 |
| EP | 2166974 | 12/2015 |
| EP | 2194906 | 3/2016 |
| EP | 2242531 | 6/2016 |
| EP | 3027259 | 6/2016 |
| EP | 3041566 | 7/2016 |
| EP | 3046500 | 7/2016 |
| EP | 3058959 | 8/2016 |
| EP | 3067417 | 9/2016 |
| EP | 2176283 | 11/2016 |
| EP | 3107610 | 12/2016 |
| EP | 3108000 | 12/2016 |
| EP | 3117005 | 1/2017 |
| EP | 3119310 | 1/2017 |
| EP | 3134431 | 3/2017 |
| EP | 3168298 | 5/2017 |
| EP | 3215191 A2 | 9/2017 |
| EP | 3253437 | 12/2017 |
| EP | 3257547 | 12/2017 |

(56) References Cited

FOREIGN PATENT DOCUMENTS

| | | |
|---|---|---|
| EP | 1928557 | 6/2018 |
| JP | S60-73547 U | 5/1985 |
| JP | H03-29665 A | 2/1991 |
| JP | H03-46305 U | 4/1991 |
| JP | H07-184929 A | 7/1995 |
| JP | H09-10315 A | 1/1997 |
| JP | H11-137568 A | 5/1999 |
| JP | H11-285533 A | 10/1999 |
| JP | 2001293090 | 10/2001 |
| JP | 2001321447 | 11/2001 |
| JP | 2003275223 | 9/2003 |
| JP | 2005034640 | 2/2005 |
| JP | 2011239987 | 12/2011 |
| JP | 2011255025 | 12/2011 |
| JP | 2013013592 | 7/2013 |
| JP | 2015015988 | 1/2015 |
| JP | 2015015989 | 1/2015 |
| JP | 2015173972 | 10/2015 |
| JP | 2015112360 | 9/2017 |
| JP | 2018153556 | 10/2018 |
| JP | 2019141250 | 12/2018 |
| JP | 2019076411 | 5/2019 |
| WO | 1993009239 | 5/1993 |
| WO | 1995034670 | 12/1995 |
| WO | 1996017947 | 6/1996 |
| WO | 1996023810 | 8/1996 |
| WO | 1996030540 | 10/1996 |
| WO | 1998010088 | 3/1998 |
| WO | 1998025535 | 6/1998 |
| WO | 1999027110 | 6/1999 |
| WO | 1999043360 | 9/1999 |
| WO | 1999058700 | 11/1999 |
| WO | 1999061595 | 12/1999 |
| WO | 200023116 | 4/2000 |
| WO | 1999060146 | 5/2000 |
| WO | 2000024916 | 5/2000 |
| WO | 2000061017 | 10/2000 |
| WO | 2000066780 | 11/2000 |
| WO | 2000075353 | 12/2000 |
| WO | 2001014539 | 3/2001 |
| WO | 2001023001 | 4/2001 |
| WO | 2001025465 | 4/2001 |
| WO | 2001032711 | 5/2001 |
| WO | 2001036623 | 5/2001 |
| WO | 2001042444 | 6/2001 |
| WO | 2001068888 | 9/2001 |
| WO | 2001096587 | 12/2001 |
| WO | 2002012525 | 2/2002 |
| WO | 2002014487 | 2/2002 |
| WO | 2002020748 | 3/2002 |
| WO | 2002070719 | 9/2002 |
| WO | 2002071843 | 9/2002 |
| WO | 2003010320 | 2/2003 |
| WO | 2003024502 | 3/2003 |
| WO | 2003042397 | 5/2003 |
| WO | 2003087382 | 10/2003 |
| WO | 2003087383 | 10/2003 |
| WO | 2004044003 | 5/2004 |
| WO | 2004083441 | 9/2004 |
| WO | 2004108922 | 12/2004 |
| WO | 2004111248 | 12/2004 |
| WO | 2005005610 | 1/2005 |
| WO | 2005012537 | 2/2005 |
| WO | 2005111220 | 11/2005 |
| WO | 2006063247 | 6/2006 |
| WO | 2006102072 | 9/2006 |
| WO | 2007064739 A2 | 6/2007 |
| WO | 2007130519 | 11/2007 |
| WO | 2008133615 | 11/2008 |
| WO | 2009049823 | 4/2009 |
| WO | 2009056131 | 5/2009 |
| WO | 2007148971 | 7/2009 |
| WO | 2009125196 | 10/2009 |
| WO | 2009134681 | 11/2009 |
| WO | 2011038187 | 3/2011 |
| WO | 2011054976 | 5/2011 |
| WO | 2011087495 | 7/2011 |
| WO | 2011108568 | 9/2011 |
| WO | 2011122950 | 10/2011 |
| WO | 2010109053 | 11/2011 |
| WO | 2012007458 | 1/2012 |
| WO | 2012057363 | 5/2012 |
| WO | 2012109570 | 8/2012 |
| WO | 2012114090 | 8/2012 |
| WO | 2012144446 | 10/2012 |
| WO | 2013078199 | 5/2013 |
| WO | 2013164793 | 11/2013 |
| WO | 2013170078 | 11/2013 |
| WO | 2014128875 | 8/2014 |
| WO | 2014128881 | 8/2014 |
| WO | 2014160092 | 10/2014 |
| WO | 2014168953 | 10/2014 |
| WO | 2014170470 | 10/2014 |
| WO | 2014170480 | 10/2014 |
| WO | 2014172669 | 10/2014 |
| WO | 2014186579 | 11/2014 |
| WO | 2014189253 | 11/2014 |
| WO | 2014194132 | 12/2014 |
| WO | 2014201252 | 12/2014 |
| WO | 2015012924 | 1/2015 |
| WO | 2015013148 | 1/2015 |
| WO | 2015018503 | 2/2015 |
| WO | 2014186746 | 3/2015 |
| WO | 2015031686 | 4/2015 |
| WO | 2015044292 | 4/2015 |
| WO | 2015049886 | 4/2015 |
| WO | 2015057807 A1 | 4/2015 |
| WO | 2015060722 | 4/2015 |
| WO | 2015093274 | 6/2015 |
| WO | 2015108610 | 7/2015 |
| WO | 2015114365 | 8/2015 |
| WO | 2015121501 | 8/2015 |
| WO | 2015124546 | 8/2015 |
| WO | 2015137802 | 9/2015 |
| WO | 2015127128 | 11/2015 |
| WO | 2015196179 | 12/2015 |
| WO | 2016019364 | 2/2016 |
| WO | 2016054554 | 4/2016 |
| WO | 2016054557 | 4/2016 |
| WO | 2016065001 | 4/2016 |
| WO | 2016073693 | 5/2016 |
| WO | 2016081811 | 5/2016 |
| WO | 2016081927 | 5/2016 |
| WO | 2016115382 | 7/2016 |
| WO | 2016122791 | 8/2016 |
| WO | 2016126857 | 8/2016 |
| WO | 2016130591 | 8/2016 |
| WO | 2016137949 | 9/2016 |
| WO | 2016154055 | 9/2016 |
| WO | 2016154344 | 9/2016 |
| WO | 2016164609 | 10/2016 |
| WO | 2016168728 | 10/2016 |
| WO | 2016172008 | 10/2016 |
| WO | 2016172155 | 10/2016 |
| WO | 2016179496 | 11/2016 |
| WO | 2016183297 | 11/2016 |
| WO | 2016191418 | 12/2016 |
| WO | 2016196507 | 12/2016 |
| WO | 2017004514 | 1/2017 |
| WO | 2017005806 | 1/2017 |
| WO | 2017015102 | 1/2017 |
| WO | 2017019876 | 2/2017 |
| WO | 2017019994 | 2/2017 |
| WO | 2017023724 | 2/2017 |
| WO | 2017058892 | 4/2017 |
| WO | 2017070476 | 4/2017 |
| WO | 2017070516 | 4/2017 |
| WO | 2017070525 | 4/2017 |
| WO | 2017070678 | 4/2017 |
| WO | 2017075335 | 5/2017 |
| WO | 2017075338 | 5/2017 |
| WO | 2017083423 | 5/2017 |
| WO | 2017093330 | 6/2017 |
| WO | 2017096039 | 6/2017 |

(56) References Cited

FOREIGN PATENT DOCUMENTS

| WO | 2017100671 | | 6/2017 |
|---|---|---|---|
| WO | 2017100674 | | 6/2017 |
| WO | 2017100676 | | 6/2017 |
| WO | 2017100704 | | 6/2017 |
| WO | 2017136202 | | 8/2017 |
| WO | 2017136536 | | 8/2017 |
| WO | 2017192699 | | 11/2017 |
| WO | 2018044933 | A1 | 3/2018 |
| WO | 2018191450 | | 10/2018 |
| WO | 2019157070 | | 8/2019 |
| WO | 2020010035 | | 1/2020 |
| WO | 2020064660 | | 4/2020 |

OTHER PUBLICATIONS

Merten OW, et al. Viral vectors for gene therapy and gene modification approaches. Biochem Eng J. Apr. 2016;108:98-115.

Muzyczka N, et al. AAV's Golden Jubilee. Mol Ther. May 2015;23(5):807-8.

Philiport, et al. Liposomes as tools in Basic Research and Industry. CRC Press, Ann Arbor, Mich. (1995).

Kailasan S, et al. Parvovirus Family Conundrum: What makes a killer? Annu Rev Virol. Nov. 2015;2(1):425-50.

Rutledge EA, et al. Infectious clones and vectors derived from adeno-associated virus (AAV) serotypes other than AAV type 2. J Virol. Jan. 1998;72(1):309-19.

Pillay S, et al. An essential receptor for adeno-associated virus infection. Nature. Nov. 17, 2016;539(7629):456.

Platt MP, et al. Embryonic disruption of the candidate dyslexia susceptibility gene homolog Kiaa0319-like results in neuronal migration disorders. Neuroscience. Sep. 17, 2013;248:585-93.

Poon MW, et al. Distribution of Kiaa0319-like immunoreactivity in the adult mouse brain—a novel protein encoded by the putative dyslexia susceptibility gene KIAA0319-like. Histol Histopathol. Aug. 2011;26(8):953-63.

Poon MW, et al. Dyslexia-associated kiaa0319-like protein interacts with axon guidance receptor nogo receptor 1. Cell Mol Neurobiol. Jan. 2011;31(1):27-35.

Myers EW, et al. Optimal alignments in linear space. Comput Appl Biosci. Mar. 1988;4(1):11-7.

Smith DW, et al. Biocomputing: Informatics and Genome Projects. Academic Press, New York, 1993.

Kozak M. Interpreting cDNA sequences: some insights from studies on translation. Mamm Genome. Aug. 1996;7(8):563-74.

Kozak M. Point mutations define a sequence flanking the AUG initiator codon that modulates translation by eukaryotic ribosomes. Cell. Jan. 31, 1986;44(2):283-92.

Kozak M. The scanning model for translation: an update. J Cell Biol. Feb. 1989;108(2):229-41.

Heim R, et al. Engineering green fluorescent protein for improved brightness, longer wavelengths and fluorescence resonance energy transfer. Curr Biol. Feb. 1, 1996;6(2):178-82.

Heim R,et al. Improved green fluorescence Nature 373, 663-664 (Feb. 23, 1995); doi:10.1038/373663b0.

Nygaard S, et al. A universal system to select gene-modified hepatocytes in vivo. Sci Transl Med. Jun. 2016;8(342):342ra79.

Smith RH, et al. Germline viral "fossils" guide in silico reconstruction of a mid-Cenozoic era marsupial adeno-associated virus. Sci Rep. Jul. 2016;6:28965.

Li L, et al. Production and characterization of novel recombinant adeno-associated virus replicative-form genomes: a eukaryotic source of DNA for gene transfer. PLoS One. Aug. 1, 2013;(8):e69879. doi: 10.1371/journal.pone.0069879. Print 2013.

O'Reilly DR, et al. Baculovirus expression vectors: a laboratory manual. Oxford University Press, 1994.

Oliva B, et al. An automated classification of the structure of protein loops. J Mol Biol. Mar. 7, 1997;266(4):814-30.

Samaranch L, et al. MR-guided parenchymal delivery of adeno-associated viral vector serotype 5 in non-human primate brain. Gene Ther. Apr. 2017;24(4):253-261.

Petit L, et al. Rod Outer Segment Development Influences AAV-Mediated Photoreceptor Transduction After Subretinal Injection. Hum Gene Ther. May 16, 2017. Epub ahead of print.

Hinderer C et al. Delivery of an Adeno-Associated Virus Vector into CSF Attenuates Central Nervous System Disease in Mucopolysaccharidosis Type II Mice. Hum Gene Ther. Aug. 10, 2016.

Hordeaux J., et al. Efficient central nervous system AAVrh10-mediated intrathecal gene transfers in adult and neonate rats. Gene Ther.Apr. 2015, 22(4):316-24.

Merkel SF et al. Trafficking of AAV Vectors Across a Model of the Blood-Brain Barrier; a Comaparative Study of Transcytosis and Transduction Using Primary Human Brain Endothelial Cells. J Neurochem. Oct. 8, 2016.

Miyanohara A et al. Potent Spinal Parenchymal AAV9-mediated Gene Delivery by Subpial Injection in Adult Rats and Pigs. Mol Ther Methods Clin Dev. Jul. 13, 2016;3:16046.

Muralidharan G, et al. Unique glycan signatures regulate adeno-associated virus tropism in the developing brain. J Virol. Apr. 2015;89(7):3976-87.

Ponder K, et al. Intrathecal injection of lentiviral vector results in high expression in the brain of mucopolysaccharidosis VII dogs but the pattern of expression is different than for AAV9 or AAV-rh10. J Control Release. Dec. 2014, 196:71-8.

Salegio EA, et al. MRI-Guided Delivery of Viral Vectors. Methods Mol Viol. 2016;1382:217-30.

Samaranch L et al. Cerebellomedullary Cistern Delivery for AAV-Based Gene Therapy: A Technical Note for Nonhuman Primates. Hum Gene Ther Methods. Feb. 2016;27(1):13-6.

Saraiva J et al. Gene Therapy for the CNS Using AAVs: The Impact of Systemic Delivery by AAV9. J Control Release Nov. 10, 2016;241:94-109.

Shen F, et al. Inhibition of pathological brain angiogenesis through systemic delivery of AAV vector expressing soluble FLT1. Gene Therapy. Nov. 22, 2015(11):893-900.

Hinderer C, et al. Neonatal Systemic AAV Induces Tolerance to CNS Gene Therapy in MPS I Dogs and Nonhuman Primates. Mol Ther. Aug. 2015, 23(8):1298-307.

Ojala DS, et al. Adeno-associated virus vectors and neurological gene therapy. Neuroscientist. Feb. 2015;21(1):84-98.

Katz ML, et al. AAV gene transfer delays disease onset in a TPP1-deficient canine model of the late infantile form of Batten Disease. Sci Transl Med. Nov. 2015;7(313):313ra180.

Kothari P, et al. Iodine-124 Labeled Adeno-Associated Virus: A Promising Tool for Tracking Gene Therapy. Journal of Nuclear Medicine. May 2015, 56 (supplement 3), 494-494.

Landegger LD, et al. A synthetic AAV vector enables safe and efficient gene transfer to the mammalian inner ear. Nat Biotechnol. Mar. 2017;35(3):280-284.

Mason JB, et al. Delivery and evaluation of recombinant adeno-associated viral vectors in the equine distal extremity for the treatment of laminitis. Equine Vet J. Jan. 2017;49(1):79-86.

Jeong D, et al. Matricellular Protein CCN5 Reverses Established Cardiac Fibrosis. J Am Coll Cardiol. Apr. 5, 2016;67(13):1556-68.

Knezevic T, et al. Adeno-associated Virus Serotype 9—Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.

Ibrahim S, et al. Stable liver specific expression of human IDOL in humanized mice raises plasma cholesterol. Cardiovasc Res. May 2016;110(1):23-9.

Li SY, et al. Efficient and targeted transduction of nonhuman primate liver with systemically delivered optimized AAV3B vectors. Mol Ther. Dec. 2015;23(12):1867-76.

Heller KN, et al. Human alpha 7 integrin gene (ITGA7) delivered by adeno-associated virus extends survival of severely affected dystrophin/utrophin deficient mice. Oct. 2015;26(10):647-56.

Mendell JR, et al. Follistatin Gene Therapy for Sporadic Inclusion Body Myositis Improves Functional Outcomes. Mol Ther. Apr. 2017;25(4):870-879.

(56) References Cited

OTHER PUBLICATIONS

Schnepp BC, et al. Recombinant adeno-associated virus vector genomes take the form of long-lived transcriptionally competent episomes in human muscle. Hum Gene Ther. Jan. 2016;27(1):32-42.
Murlidharan G et al. Glymphatic Fluid Transport Controls Paravascular Clearance of AAV Vectors from the Brain. JCI Insight. Sep. 8, 2016;1(14).
Neuberger Ewi, et al. Establishment of two quantitative nested qPCR assays targeting the human EPO transgene. Gene Ther. Apr. 2016;23(4):330-9.
Lentz TB, et al. Insight into the Mechanism of Inhibition of Adeno-Associated Virus by the Mre11/Rad50/Nbs1 Complex. J Virol. Jan. 2015, 89(1):181-94.
Heiss JD et la., Trial of magnetic resonance-guided putaminal gene therapy for advanced Parkinson's disease. Mov Disord. May 30, 2019 [Epub ahead of print].
Sudhakar V et al., Infuse-as-you-go convective delivery to enhance coverage of elongated brain targets: technical note. J Neurosurg. Jul. 12, 2019:1-8.
Taghian et al., A Safe and Reliable Technique for Central Nervous System Delivery of AAV Vectors in the Cisterna Magna. Molecular Therapy. Nov. 16, 2019.
Haery et al., Adeno-Associated Virus Technologies and Methods for Targeted Neuronal Manipulation. Front. Neuroanat., Nov. 26, 2019.
Martin et al., Minimally Invasive Precision Brain Access Using Prospective Stereotaxy and a Trajectory Guide. J Magn Reson Imaging. Apr. 2008;27(4):737-43.
Emborg et al., Intraoperative intracerebral MRI-guided navigation for accurate targeting in nonhuman primates. Cell transplantation. Dec. 2010;19(12):1587-97.
Han et al., Interventional MRI-guided catheter placement and real time drug delivery to the central nervous system. Expert review of neurotherapeutics. Jun. 2, 2016;16(6):635-9.
Meneghini et al., Pervasive supply of therapeutic lysosomal enzymes in the CNS of normal and Krabbe-affected non-human primates by intracerebral lentiviral gene therapy. EMBO molecular medicine. May 1, 2016;8(5):489-510.
Richardson et al., Novel platform for MRI-guided convection-enhanced delivery of therapeutics: preclinical validation in nonhuman primate brain. Stereotactic and functional neurosurgery. 2011;89(3):141-51.
Richardson et al., Interventional MRI-guided putaminal delivery of AAV2-GDNF for a planned clinical trial in Parkinson's disease. Molecular Therapy. Jun. 1, 2011;19(6):1048-57.
Rosenbluth et al., Design of an in-dwelling cannula for convection-enhanced delivery. Journal of neuroscience methods. Mar. 15, 2011;196(1):118-23.
Rosenbluth et al., Automated segmentation tool for brain infusions. PloS one. 2013;8(6).
Rowland et al., Merging DBS with viral vector or stem cell implantation:"hybrid" stereotactic surgery as an evolution in the surgical treatment of Parkinson's disease. Molecular Therapy—Methods & Clinical Development. Jan. 1, 2016;3:15051.
Salegio et al., Magnetic resonance imaging-guided delivery of adeno-associated virus type 2 to the primate brain for the treatment of lysosomal storage disorders. Human gene therapy. Sep. 1, 2010;21(9):1093-103.
Salegio et al., Guided delivery of adeno-associated viral vectors into the primate brain. Advanced drug delivery reviews. May 15, 2012;64(7):598-604.
Salegio et al., MRI-guided delivery of viral vectors. InGene Therapy for Neurological Disorders 2016 (pp. 217-230). Humana Press, New York, NY.
Samaranch et al., Cerebellomedullary cistern delivery for AAV-based gene therapy: a technical note for nonhuman primates. Human gene therapy methods. Feb. 1, 2016;27(1):13-6.
Yin et al., Optimal region of the putamen for image-guided convection-enhanced delivery of therapeutics in human and non-human primates. Neuroimage. Jan. 1, 2011;54:S196-203.

Sudhakar et al., Development of a novel frameless skull-mounted ball-joint guide array for use in image-guided neurosurgery. Journal of neurosurgery. Feb. 15, 2019;1(aop):1-0.
Carter BJ. Adeno-associated virus and the development of adeno-associated virus vectors: a historical perspective. Mol Ther. Dec. 2004;10(6):981-9.
G. S. Banker, Modern Pharmaceutics, Drugs and the Pharmaceutical Sciences, v. 72, Marcel Dekker, New York, Inc., 1996.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 6, 2007;27(1):91-105.
Hastie E, et al. Adeno-Associated Virus at 50: A Golden Anniversary of Discovery, Research, and Gene Therapy Success—A Personal Perspective. Hum Gene Ther. May 2015, 26(5):257-65.
Aydemir F, et al. Mutants at the 2-fold interface of AAV2 structural proteins suggest a role in viral transcription for AAV capsids. J Virol. Jul. 2016;90(16):7196-204.
Bantel-Schaal U, et al. Human adeno-associated virus type 5 is only distantly related to other known primate helper-dependent parvoviruses. J Virol. Feb. 1999;73(2):939-47.
Berry GE, et al. Cellular transduction mechanisms of adeno-associated viral vectors. Curr Opin Virol. Dec. 2016;21:54-60.
Chiorini JA, et al. Adeno-associated virus (AAV) type 5 Rep protein cleaves a unique terminal resolution site compared with other AAV serotypes. J Virol. May 1999;73(5):4293-8.
Chiorini JA, et al. Cloning and characterization of adeno-associated virus type 5. J Virol. Feb. 1999;73(2):1309-19.
Chiorini JA, et al. Cloning of adeno-associated virus type 4 (AAV4) and generation of recombinant AAV4 particles. J Virol. Sep. 1997;71(9):6823-33.
Earley LF, et al. Adeno-Associated Virus Assembly-Activating Protein Is Not an Essential Requirement for Capsid Assembly of AAV Serotypes 4, 5 and 11. J Virol. Jan. 2017;91(3):pii:e0198-16.
Ding C, et al., Biochemical Characterization of Junonia Coenia Densovirus Nonstructural Protein NS-1. J. Virol., 76(1):338-345 2002.
Adachi K, et al. Drawing a high-resolution functional map of adeno-associated virus capsid by massively parallel sequencing. Nat Commun. 2014;5:3075. doi: 10.1038/ncomms4075.
Altschul SF, et al. Basic local alignment search tool. J Mol Biol. Oct. 5, 1990;215(3):403-10.
Carillo H, et al. The Multiple Sequence Alignment Problem in Biology. SIAM J. Appl. Math. 48-5 (1988), pp. 1073-1082.
Devereux J A comprehensive set of sequence analysis programs for the VAX. Nucleic Acids Res. Jan. 11, 1984;12(1 Pt 1):387-95.
Gribskov M, et al. Sequence Analysis Primer. M Stockton Press, New York, 1991.
Griffin AM, et al. Computer Analysis of Sequence Data, Part I. Humana Press, New Jersey, 1994.
Berge SM Pharmaceutical salts. J Pharm Sci. Jan. 1977;66(1):1-19.
Bell P, et al. Effects of self-complementarity, codon optimization, transgene, and dose on liver transduction with AAV8. Hum Gene Ther Methods. Dec. 2016;27(6):228-237.
Heim et al., Wavelength mutations and posttranslational autoxidation of green fluorescent protein. Proc. Natl. Acad. Sci. USA (1994).
Hastie E, et al. Recombinant adeno-associated virus vectors in the treatment of rare diseases. Expert Opin Orphan Drugs. 2015;3(6):675-689.
Fargnoli AS, et al. Liquid jet delivery method featuring S100A1 gene therapy in the rodent model following acute myocardial infarction. Gene Ther. Feb. 2016;23(2):151-7.
Aubourg P. Gene therapy for rare central nervous system diseases comes to age. Endocr Dev. 2016;30:141-6.
Bankiewicz KS et al. AAV Viral Vector Delivery to the Brain by Shape-conforming MR-guided Infusions. J Control Release. Oct. 28, 2016;240:434-442.
Bey K, et al. Efficient CNS targeting in adult mice by intrathecal infusion of single-stranded AAV9-GFP for gene therapy of neurological disorders. Gene Ther. Apr. 20, 2017. Epub ahead of print.

(56) References Cited

OTHER PUBLICATIONS

Brulet R, et al. NEUROD1 Instructs Neuronal Conversion in Non-Reactive Astrocytes. Stem Cell Reports. May 11, 2017. Epub ahead of print.
Cabral-Miranda F, et al. rAAV8-733-Mediated Gene Transfer of CHIP/Stub-1 Prevents Hippocampal Neuronal Death in Experimental Brain Ischemia. Mol Ther. Feb. 2017;25(2):392-400.
Chandler RJ, et al. Systemic AAV9 gene therapy improves the lifespan of mice with Niemann-Pick disease, type C1. Hum Mol Genet. Jan. 2017;26(1):52-64.
Dang CH, et al. In vivo dynamics of AAV-mediated gene delivery to sensory neurons of the trigeminal ganglia. Sci Rep. Apr. 19, 2017;7(1):927.
Dimidschstein J, et al. A viral strategy for targeting and manipulating interneurons across vertebrate species. Nat Meurosci. Dec. 2016;19(12):1743-1749.
Donsante A et al. Intracerebroventricular delivery of self-complementary adeno-associated virus serotype 9 to the adult rat brain. Gene Ther. May 2016;23(5):401-7.
El-Shamayleh Y, et al. Strategies for targeting primate neural circuits with viral vectors. J Neurophysiol. Jul. 2016;116(1):122-34.
Foust KD, et al. Intravascular AAV9 preferentially targets neonatal neurons and adult astrocytes. Nat Biotechnol. Jan. 2009;27(1):59-65. doi: 10.1038/nbt.1515. Epub Dec. 21, 2008.
Gessler DJ et al. Gene Therapy for the Treatment of Neurological Disorders: Metabolic Disorders. Methods Mol Biol. 2016;1382:429-65.
Gilkes JA et al. Preferred Transduction with AAV8 and AAV9 Via Thalamic Administration in the MPS IIIB Model: A Comparison of Four rAAV Serotypes. Mol Genet Metab Rep. Dec. 7, 2015;6:48-54.
Gombash SE, et al. Systemic Gene Therapy for Targeting the CNS. Methods Mol Biol. 2016;1382:231-7.
Gurda BL, et al. Evaluation of AAV-mediated gene therapy for central nervous system disease in canine mucopolysaccharidosis VII. Mol Ther. Feb. 2016;24(2):206-16.
Ahmed SS, et al. rAAV gene therapy in a Canavan's disease mouse model reveals immune impairments and an extended pathology beyond the central nervous system. Mol Ther. Jun. 2016;24(6):1030-41.
Dashkoff J, et al. Tailored transgene expression to specific cell types in the central nervous system after peripheral injection with AAV9. Mol Ther Methods Clin Dev. Dec. 2016;3:16081.
Gruntman AM, et al. Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.
Aoyama Y, et al. Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.
Greig JA, et al. Impact of intravenous infusion time on AAV8 vector pharmacokinetics, safety, and liver transduction in cynomolgus macaques. Mol Ther Methods Clin Dev. Dec. 2016;3:16079.
Gruntman AM, et al. Delivery of Adeno-associated virus gene therapy by intravascular limb infusion methods. Hum Gene Ther Clin Dev Sep. 2015;26(3):159-64.
Hagg A, et al. Using AAV vectors expressing the beta 2-adrenocep-tor or associated G alpha proteins to modulate skeletal muscle mass and muscle fiber size. Sci Rep. Mar. 2016;6:23042.
Greig JA, et al. Intramuscular administration of AAV overcomes pre-existing neutralizing antibodies in rhesus macaques. Vaccine. Dec. 2016;34(50):6323-6329.
Al J, et al. Adeno-associated virus serotype rh.10 displays strong muscle tropism following intraperitoneal delivery. Sci Rep. Jan. 2017;7:40336.
Baum BJ, et al. Advances in salivary gland gene therapy—oral and systemic implications. Expert Opinion on Biological Therapy. 2015;15(10):1443-54.

Hai B, et al. Long-term transduction of miniature pig parotid glands using serotype 2 adeno-associated viral vectors. J Gene Med. Jun. 2009;11(6):506-14.
Medtronic, Cranial Solutions: A Brain Biopsy Solution Built Around Your Surgical Workflow. www.medtronicneurosurgery.com. 2013.
"Martin, A, et al. Minimally Invasive Precision Brain Access Using Prospective Stereotaxy and a Trajectory Guide, Journal of Magnetic Resonance Imaging 27:737-743 (2008)".
Emborg M, et al. Intraoperative Intracerebral MRI-Guided Navigation for AccurateTargeting in Nonhuman Primates, Cell Transplant., 2010 ; 19(12): 1587-159.
Salegio E et al. MRI-Guided Delivery of Viral Vectors, Gene Therapy for Neurological Disorders: Methods and Protocols, Methods in Molecular Biology, vol. 1382, 2016.
Larson et al. (2012) "An Optimized System for Interventional MRI Guided Stereotactic Surgery: Preliminary Evaluation of Targeting Accuracy" Neurosurgery 70 (OPERATIVE): ons95-ons103, pp. 1-18.
Potts et al. (2013) "Devices for cell transplantation into the central nervous system: Design considerations and emerging technologies" Surg Neurol Int 4(1): S22-S30.
Nicolson SC, et al. Identification and validation of small molecules that enhance recombinant Adeno-associated virus transduction following high throughput screen. J Virol. Jul. 2016;90(16):7019-31.
Wang M, et al. Direct interaction of human serum proteins with AAV virions to enhance AAV transduction: Immediate impact on clinical applications. Gene Ther. Jan. 2017;24(1):49-59.
Watakabe A, et al. Comparative analyses of adeno-associated viral vector serotypes 1 2 5 8 and 9 in marmoset mouse and macaque cerebral cortex. Neurosci Res.Apr. 2015, 93:144-57.
Xiao P, et al. Disruption of microtubules post virus entry enhances adeno-associated virus vector transduction. Hum Gene Ther. Apr. 2016;27(4):309-24.
Hudry EM, et al. Exosome-associated AAV vector as a robust and convenient neurosocience tool. Gene Ther. Apr. 2016;23(4):380-92.
Nery FC, et al. New methods for investigation of neuronal migration in embryonic brain explants J Neurosci Methods.Jan. 2015, 239:80-4.
Su W et al. Recombinant adeno-associated viral (rAAV) vectors mediate efficient gene transduction in cultured neonatal and adult microglia. J Neurochem. Jan. 2016;136 Suppl 1:49-62.
Ren XF, et al. Adeno-associated virus-mediated BMP-7 and SOX9 in vitro co-transfection of human degenerative intervertebral disc cells. Genet Mol Res. Apr. 22, 2015;14(2):3736-44.
Alves S et al. Ultramicroscopy as a Novel Tool to Unravel the Tropism of AAV Gene Therapy Vectors in the Brain. Sci Rep. Jun. 20, 2016;6:28272.
Kothari P, et al. Radioiodinated Capsids Facilitate In Vivo Non-Invasive Tracking of Adeno-Associated Gene Transfer Vectors. Sci Rep. Jan. 2017;7:39594.
Xie Q, et al. The 2.8 Å Electron Microscopy Structure of Adeno-Associated Virus-DJ Bound by a Heparinoid Pentasaccharide. Mol Ther Methods Clin Dev. Mar. 8, 2017;5:1-12.
Srivastava A. Adeno-Associated Virus: The Naturally Occurring Virus Versus the Recombinant Vector. Hum Gene Ther. Jan. 2016;27(1):1-6.
Thorne B, et al. Gene Therapy. Adv Biochem Eng Biotechnol. Mar. 14, 2017 Epub ahead of print.
Tratschin JD, et al. Adeno-associated virus vector for high-frequency integration, expression, and rescue of genes in mammalian cells. Mol Cell Biol. Nov. 1985;5(11):3251-60.
Srivastava A, et al. Nucleotide sequence and organization of the adeno-associated virus 2 genome. J Virol. Feb. 1983;45(2):555-64.
Summerford C, et al. AAVR: A multi-serotype receptor for AAV. Mol Ther. Apr. 2016;24(4):663-6.
Xie Q, et al. The atomic structure of adeno-associated virus (AAV-2), a vector for human gene therapy. Proc Natl Acad Sci U S A. Aug. 6, 2002;99(16):10405-10. Epub Jul. 22, 2002.
Wu P, et al. Mutational analysis of the adeno-associated virus type 2 (AAV2) capsid gene and construction of AAV2 vectors with altered tropism. J Virol. Sep. 2000;74(18):8635-47.
Von Heinje G. Sequence Analysis in Molecular Biology. Academic Press, 1987.

(56) References Cited

OTHER PUBLICATIONS

Stahl PH, et al. Pharmaceutical Salts: Properties, Selection, and Use. Wiley-VCH, 2008.
Yang C, et al. Sequential adeno-associated viral vector serotype 9-green fluorescent protein gene transfer causes massive inflammation and intense immune response in rat striatum. Hum Gene Ther. Jul. 2016;27(7):528-43.
Chandler RJ, et al. rAAV integration and genotoxicity: insights from animal models. Hum Gene Ther. Apr. 2017;28(4):314-322.
Ye L., et al. Adeno-Associated Virus Vector Mediated Delivery of the HBV Genome Induces Chronic Hepatitis B Virus Infection and Liver Fibrosis in Mice. PLoS One. Jun. 2015, 10(6):e0130052.
Wang S, et al. Direct brain infusion can be enhanced with focused ultrasound and microbubbles. J Cereb Blood Flow Metab. Feb. 2017;37(2):706-714.
Wang et al., Noninvasive, neuron-specific gene therapy can be facilitated by focused ultrasound and recombinant adeno-associated virus. Gene Therapy. Nov. 22, 2014, 104-110.
Weber-Adrian D, et al. Gene delivery to the spinal cord using MRI-guided focused ultrasound. Gene Ther. Jul. 2015, 22(7):568-77.
Wu D et al. Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush. Front Mol Neurosci. Jul. 5, 2016;9:49.
Zhu W, et al. Soluble FLT1 Gene Therapy Alleviates Brain Arteriovenous Malformation Severity. Stroke. May 2017;48(5):1420-1423.
Watson ZL, et al. Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.
Suzuki J, et al. Cochlear gene therapy with ancestral AAV in adult mice: complete transduction of inner hair cells without cochlear dysfunction. Apr. 3, 2017;7:45524.
Woodard KT et al. Heparan Sulfate Binding Promotes Accumulation of Intravitreally Delivered Adeno-associated Viral Vectors at the Retina for Enhanced Transduction but Weakly Influences Tropism. J Virol. Oct. 14, 2016;90(21):9878-9888.
Wang LL, et al. Comparative study of liver gene transfer with AAV vectors based on endogenous and engineered AAV capsids Mol Ther. Dec. 2015;23(12):1877-87.
Sondhi D, et al. Genetic Modification of the Lung Directed Toward Treatment of Human Disease. Hum Gene Ther. Jan. 2017;28(1):3-84.
Yalvac ME, et al. AAV1.NT-3 gene therapy attenuates spontaneous autoimmune peripheral polyneuropathy. Gene Ther. Jan. 2016;23(1):95-102.
Srivastava A. In Vivo Tissue-tropism of Adeno-associated Viral Vectors. Curr Opin Virol. Sep. 2, 2016;21:75-80.
Adamson-Small L, et al. Sodium chloride enhances rAAV production in a serum-free suspension manufacturing platform using the Herpes Simplex Virus System. Hum Gene Ther Methods. Feb. 2017;28(1):1-14.
Al J, et al. A Scalable and Accurate Method for Quantifying Vector Genomes of Recombinant Adeno-Associated Viruses in Crude Lysate. Hum Gene Ther Methods. Apr. 13, 2017. Epub ahead of print.
Buclez PO, et al. Rapid, scalable, and low-cost purification of recombinant adeno-associated virus produced by baculovirus expression vector system. Mol Ther Methods Clin Dev. May 2016;3:16035.
Burnham B, et al. Analytical ultracentrifugation as an approach to characterize recombinant adeno-associated viral vectors. Hum Gene Ther Methods. Dec. 2015;26(6):228-42.
Clement N, et al. Manufacturing of recombinant adeno-associated viral vectors for clinical trials. Mol Ther Methods Clin Dev. Mar. 2016;3:16002.
D'Costa S, et al. Practical utilization of recombinant AAV vector reference standards: focus on vector genome titration by free ITR qPCR. Mol Ther Methods Clin Dev. Mar. 2016;5:16019.

Grieger JC, et al. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-97.
Gruntman AM, et al. Stability and Compatibility of Recombinant Adeno-Associated Virus Under Conditions Commonly Encountered in Human Gene Therapy Trials. Hum Gene Ther Methods. Apr. 2015, 26(2):71-6.
Kajigaya S, et al. Self-assembled B19 parvovirus capsids, produced in a baculovirus system, are antigenically and immunogenically similar to native virions. Proc Natl Acad Sci U S A. Jun. 1, 1991;88(11):4646-50.
Kirnbauer R, et al. Virus-like particles of bovine papillomavirus type 4 in prophylactic and therapeutic immunization. Virology. May 1, 1996;219(1):37-44.
Kohlbrenner E, et al. Production and Characterization of Vectors Based on the Cardiotropic AAV Serotype 9. Methods Mol Biol. 2017;1521:91-107.
Kotin RM, et al. Large-scale recombinant adeno-associated virus production. Hum Mol Genet. Apr. 15, 2011;20(R1):R2-6. doi: 10.1093/hmg/ddr141. Epub Apr. 29, 2011.
Kotin RM, et al. Manufacturing clinical grade recombinant adeno-associated virus using invertebrate cell lines. Hum Gene Ther. Mar. 28, 2017. Epub ahead of print.
Kotterman MA, et al. Enhanced cellular secretion of AAV2 by expression of foreign viral envelope proteins. Biochemical Engineering Journal, vol. 93, Jan. 15, 2015, pp. 108-114.
Methods in Molecular Biology, ed. Richard, Humana Press, NJ (1995).
International Search Report received in corresponding PCT application No. PCT/US2018/042391 dated Oct. 12, 2018.
De Leeuw CN et al. rAAV-compatible MiniPromoters for Restricted Expression in the Brain and Eye. Mol Brain. May 10, 2016;9(1):52.
Hirsch ML, et al. Delivering Transgenic DNA Exceeding the Carrying Capacity of AAV Vectors. Methods Mol Biol. 2016;1382:21-39.
Lu J, et al. A 5'non-coding exon containing engineered intron enhances transgene expression from recombinant AAV vectors in vivo. Hum Gene Ther. Jan. 2017;28(1):125-134.
Powell SK, et al. Viral expression cassette elements to enhance transgene target specificity and expression in gene therapy. Discov Med. Jan. 2015;19(102):49-57.
Rosario AM et al. Microglia-specific Targeting by Novel Capsid-modified AAV6 Vectors. Mol Ther Methods Clin Dev. Apr. 13, 2016;3:16026.
Wang L, et al. Productive life cycle of adeno-associated virus serotype 2 in the complete absence of a conventional polyadenylation signal. J Gen Virol. Sep. 2015;96(9):2780-7.
Yan ZY, et al. Optimization of recombinant adeno-associated virus mediated expression for large transgenes, using a synthetic promoter and tandem array enhancers. Hum Gene Ther. Jun. 2015;26(6):334-46.
Jackson KL, et al. Better Targeting, Better Efficiency for Wide-Scale Neuronal Transduction with the Synapsin Promoter and AAV-PHP. B. Front Mol Neurosci. Nov. 2016;6:116.
McClements ME, et al. A fragmented adeno-associated viral dual vector strategy for treatment of diseases caused by mutations in large genes leads to expression of hybrid transcripts. J Genet Syndr Gene Ther. Nov. 2016;7(5):311.
Parr MJ, et al. Tumor-selective transgene expression in vivo mediated by an E2F-responsive adenoviral vector. Nat Med. Oct. 1997;3(10):1145-9.
Reid CA, et al. miRNA mediated post-transcriptional silencing of transgenes leads to increased adeno-associated viral vector yield and targeting specificity. Gene Ther. Jun. 15, 2017. Epub ahead of print.
Sawada Y et al. Inflammation-induced Reversible Switch of the Neuron-specific Enolase Promoter from Purkinje Neurons to Bergmann Glia. Sci Rep. Jun. 13, 2016;6:27758.
Lukashcuk V et al. AAV9-mediated central nervous system-targeted gene delivery via cisterna magna route in mice. Mol Ther Methods Clin Dev. Feb. 17, 2016;3:15055.

(56) References Cited

OTHER PUBLICATIONS

Tarantal AF, et al. Systemic and Persistent Muscle Gene Expression in Rhesus Monkeys with a Liver De-targeted Adeno-Associated Virus (AAV) Vector. Hum Gene Ther. May 2017;28(5):385-391.
Huang LY, et al. Characterization of the Adeno-Associated Virus 1 and 6 Sialic Acid Binding Site. J Virol. May 12, 2016;90(11):5219-30.
Siu JJ, et al. Improved gene delivery to adult mouse spinal cord through the use of engineered hybrid adeno-associated viral serotypes. Gene Ther. Apr. 25, 2017. Epub ahead of print.
Deng XF, et al. Replication of an autonomous human parvovirus in non-dividing human airway epithelium is facilitated through the DNA damage and repair pathways. PLoS Pathog. Jan. 2016;12(1):e1005399.
Kailasan S, et al. Structure of an Enteric Pathogen, Bovine Parvovirus. J Virol. Mar. 2015, 89(5):2603-14.
Alton EW, et al. Repeated nebulisation of non-viral CFTR gene therapy in patients with cystic fibrosis: a randomised, double-blind, placebo-controlled, phase 2b trial. Lancet Respir Med. Sep. 2015;3(9):684-91.
Baum BJ, et al. Early responses to adenoviral-mediated transfer of the aquaporin-1 cDNA for radiation-induced salivary hypofunction. Proc Natl Acad Sci U S A. Nov. 20, 2012;109(47):19403-7.
Shen W, et al. Analysis of the Cis and Trans Requirements for DNA Replication at the Right End Hairpin of the Human Bocavirus 1 Genome. J Virol. Aug. 2016;90(17):7761-77.
Hocquemiller M et al. Adeno-Associated Virus-Based Gene Therapy for CNS Diseases. Hum Gene Ther. Jul. 2016;27(7):478-96.
Blits B, et al. Perspective on the Road toward Gene Therapy for Parkinson's Disease. Front Neuroanat. Jan. 2017;10:128.
Singh A et al. Therapeutic Value of Adeno Associated Virus as a Gene Therapy Vector for Parkinson's Disease—A Focused Review. Curr Gene Ther. Jul. 29, 2016.
Jolesz F. Intraoperative Imaging in Neurosurgery: Where Will the Future Take Us?. Acta Nerochir Suppl. 2011:109:21-25.
Forsayeth J, et al. A Dose-Ranging Study of AAV-hAADC Therapy in Parkinsonian Monkeys. Mol Ther. Oct. 2006;14(4):571-577.
Voyager Therapeutics—Investors & Media—Press Release, Voyager Therapeutics Announces Positive Interim Results from Phase 1b Trial of VY-AADC01 for Advanced Parkinson's Disease, Dec. 7, 2016, pp. 1-6.
Arrigo A, et al. Visual System Involvement in Patients with Newly Diagnosed Parkinson Disease. Radiology. Jul. 11, 2017:161732.
Katz N, et al. Standardized method for intra-cisterna magna delivery under fluoroscopic guidance in nonhuman primates. Hum Gene Ther Methods Jul. 21, 2018 Epub ahead of print.
Naidoo J, et al. Extensive Transduction and Enhanced Spread of a Modified AAV2 Capsid in the Non-human Primate CNS. Mol Ther. Jul. 12, 2018 Epub ahead of print.
Bankiewicz KS, et al. Convection-enhanced delivery of AAV vector in Parkinsonian monkeys; in vivo detection of gene expression and restoration of dopaminergic function using pro-drug approach. Exp. Neurol. 2000 164;2-14.
Bankiewicz KS, et al. Long-term clinical improvement in MPTP-lesioned primates after gene therapy with AAV-hAADC. Mol Ther. Oct. 2006;14(4):564-570.
Christine CW, et al. Safety and tolerability of putaminal AADC gene therapy for Parkinson disease. Neurology 2009;73:1662-1669.
Espay AJ, et al. Optimizing extended-release carbidopa/levodopa in Parkinson disease. Neurol Clin Pract 2017;7:86-93.
Richardson RM, et al. Novel platform for MRI-guided convection enhanced delivery of therapeutics: preclinical validation in nonhuman primate brain. Stereotact Funct Neurosurg 2011;89:141-151.
Su X, et al. Real-time MR imaging with gadoteridol predicts distribution of transgenes after convection-enhanced delivery of AAV2 vectors. Mol Ther Aug. 2010; 18(8):1490-1495.
Noroozian Z et al., MRI-Guided Focused Ultrasound for Targeted Delivery of rAAV to the Brain. Methods Mol Biol. 2019;1950:177-197.
Donner JM et al., Intraspinal and Intracortical Delivery of AAV Vectors for Intersectional Circuit Tracing in Non-transgenic Species. Methods Mol Biol. 2019;1950:165-176.
Christine CW, et al. MRI-guided Phase 1 Trial of Putaminal AADC Gene Therapy for Parkinson's Disease. Ann Neurol. Feb. 25, 2019.
Bartus et al., Safety/feasibility of targeting the substantia nigra with AAV2-neurturin in Parkinson patients. Neurology. Apr. 30, 2013;80(18):1698-701. Epub Apr. 10, 2013.
Jolesz, Intraoperative imaging in neurosurgery: where will the future take us?. Acta Neurochir Suppl. 2011;109:21-5.
Kells et al., Efficient gene therapy-based method for the delivery of therapeutics to primate cortex. PNAS Feb. 17, 2009 106 (7) 2407-2411.
Richardson et al., Novel platform for MRI-guided convection-enhanced delivery of therapeutics: preclinical validation in nonhuman primate brain. Stereotact Funct Neurosurg. 2011;89(3):141-51. Epub Apr. 14, 2011.
San Sebastian et al., Safety and tolerability of magnetic resonance imaging-guided convection-enhanced delivery of AAV2-hAADC with a novel delivery platform in nonhuman primate striatum. Hum Gene Ther. Feb. 2012;23(2):210-7. Epub Jan. 26, 2012.
San Sebastian et al., Safety and tolerability of MRI-guided infusion of AAV2-hAADC into the mid-brain of nonhuman primate. Mol Ther Methods Clin Dev. 2014; 3: 14049. Published online Oct. 15, 2014.
Richardson RM et al., Interventional MRI-guided putaminal delivery of AAV2-GDNF for a planned clinical trial in Parkinson's disease. Mol Ther. Jun. 2011;19(6):1048-57.
Bobo et al., Convection-enhanced delivery of macromolecules in the brain. Proc Natl Acad Sci U S A. Mar. 15, 1994,91(6):2076-80.
Krauze et al., Reflux-free cannula for convection-enhanced high-speed delivery of therapeutic agents. J Neurosurg. Nov. 2005;103(5):923-9.
Saito et al., Gadolinium-loaded liposomes allow for real-time magnetic resonance imaging of convection-enhanced delivery in the primate brain. Exp Neurol. Dec. 2005;196(2):381-9. Epub Sep. 28, 2005.
Varenika et al., Detection of infusate leakage in the brain using real-time imaging of convection-enhanced delivery. J Neurosurg. Nov. 2008;109(5):874-80.
Mietzsch M, et al. OneBac 2.0: Sf9 Cell Lines for Production of AAV1, AAV2 and AAV8 Vectors with Minimal Encapsidation of Foreign DNA. Hum Gene Ther Methods. Feb. 2017;28(1):15-22.
Mietzsch M, et al. OneBac 2.0: Sf9 cell lines for production of AAV5 vectors with enhanced infectivity and minimal encapsidation of foreign DNA. Hum Gene Ther. Oct. 26, 2015(10):688-97.
Nambiar B, et al. Characteristics of minimally oversized adeno-associated virus vectors encoding human Factor VIII generated using producer cell lines and triple transfection. Hum Gene Ther Methods. Feb. 2017;28(1):23-38.
Pacouret S, et al. AAV-ID: A Rapid and Robust Assay for Batch-to-Batch Consistency Evaluation of AAV Preparations. Mol Ther. Apr. 17, 2017. Epub ahead of print.
Penaud-Budloo M, et al. Accurate identification and quantification of DNA species by next-generation sequencing in adeno-associated viral vectors produced in insect cells. Hum Gene Ther Methods. May 2, 2017. Epub ahead of print.
Ruffing M, et al. Assembly of viruslike particles by recombinant structural proteins of adeno-associated virus type 2 in insect cells. J Virol. Dec. 1992;66(12):6922-30.
Samulski RJ, et al. Helper-free stocks of recombinant adeno-associated viruses: normal integration does not require viral gene expression. J Virol. Sep. 1989;63(9):3822-8.
Smith RH, et al. A simplified baculovirus-AAV expression vector system coupled with one-step affinity purification yields high-titer rAAV stocks from insect cells. Mol Ther. Nov. 2009;17(11):1888-96. doi: 10.1038/mt.2009.128. Epub Jun. 16, 2009.
Urabe M, et al. Scalable generation of high-titer recombinant adeno-associated virus type 5 in insect cells. J Virol. Feb. 2006;80(4):1874-85.
Van Der Loo JCM, et al. Progress and challenges in viral vector manufacturing. Hum Mol Genet. Apr. 2016;25(R1):R42-52.

(56) References Cited

OTHER PUBLICATIONS

Wasilko DJ, et al. The titerless infected-cells preservation and scale-up (TIPS) method for large-scale production of NO-sensitive human soluble guanylate cyclase (sGC) from insect cells infected with recombinant baculovirus. Protein Expr Purif. Jun. 2009;65(2):122-32. doi: 10.1016/j.pep.2009.01.002. Epub Jan. 11, 2009.
Zhao KN, et al. BPV1 E2 protein enhances packaging of full-length plasmid DNA in BPV1 pseudovirions. Virology. Jul. 5, 2000;272(2):382-93.
Pierson EE, et al. Resolving adeno-associated viral particle diversity with charge detection mass spectrometry. Anal Chem. Jul. 2016;88(13):6718-25.
Rashnonejad A, et al. Large-Scale Production of Adeno-Associated Viral Vector Serotype-9 Carrying the Human Survival Motor Neuron Gene. Mol Biotechnol. Jan. 2016;58(1):30-6.
Ling C, et al. Strategies to generate high-titer, high-potency recombinant AAV3 serotype vectors. Mol Ther Methods Clin Dev. May 2016;3:16029.
Afione S, et al. Identification and Mutagenesis of the Adeno-Associated Virus 5 Sialic Acid Binding Region.J Virol. Feb. 2015, 89(3):1660-72.
Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.
Halder S, et al. Structure of neurotropic adeno-associated virus AAVrh.8. J Struct Biol. Oct. 2015;192(1):21-36.
Huang LY, et al. Characterization of the adeno-associated virus 1 and 6 sialic acid binding site. J Virol. May 2016;90(11):5219-30.
Mao Y, et al. Single point mutation in adeno-associated viral vectors—DJ capsid leads to improvement for gene delivery in vivo. BMC Biotechnol. Jan. 2016;16:1.
Marsic D et al. Altering Tropism of rAAV by Directed Evolution. Methods of Mol Biol. 2016;1382:151-73.
Tu MY, et al. Role of capsid proteins in parvoviruses infection. Virol J. Aug. 2015, 4;12:114.
Zeng C, et al. Probing the Link between Genomic Cargo, Contact Mechanics and Nanoindentation in Recombinant Adeno-Associated Virus 2. J Phys Chem B. Mar. 2017;121(8):1843-1853.
Zinn E, et al. In Silico Reconstruction of the Viral Evolutionary Lineage Yields a Potent Gene Therapy Vector. Cell Rep. Aug. 2015, 12(6):1056-68.
Grimm D, et al. E Pluribus Unum: 50 years of research, millions of viruses and one goal—tailored acceleration of AAV evolution. Mol Ther. Dec. 2015;23(12):1819-1831.
Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.
Ling C, et al. Development of Optimized AAV Serotype Vectors for High-Efficiency Transduction at Further Reduced Doses. Hum Gene Ther Methods. Aug. 2016;27(4):143-9.
Pillay S, et al. An essential receptor for adeno-associated virus infection. Nature. Feb. 2016;530(7588):108-12.
Li BZ, et al. Site directed mutagenesis of surface-exposed lysine residues leads to improved transduction by AAV2 but not AAV8 vectors in murine hepatocytes in vivo. Hum Gene Ther Methods. Dec. 2015;26(6):211-20.
Shen S, et al. Functional Analysis of the Putative Integrin Recognition Motif on Adeno-associated virus 9. J Biol Chem. Jan. 2015, 290(3):1496-504.
Steines B, et al. CFTR gene transfer with AAV improves early cystic fibrosis pig phenotypes. JCI Insight. Sep. 2016;1(14):e88728.
Bensky MJ, et al. Targeted gene delivery to the enteric nervous system using AAV: a comparison across serotypes and capsid mutants.Mol Ther. Mar. 2015;23(3):488-500.
Castle MJ, et al. Controlling AAV Tropism in the Nervous System with Natural and Engineered Capsids. Methods Mol Biol. 2016;1382:133-49.
Choudhury SR, et al. Widespread CNS gene transfer and silencing after systemic delivery of novel AAV-AS vectors. Mol Ther. Apr. 2016;24(4):726-35.
Davis AS, et al. Rational design and engineering of a modified adeno-associated virus (AAV1)-based vector system for enhanced retrograde gene delivery. Neurosurgery. Feb. 2015;76(2):216-25.
Deverman BE et al. Cre-dependent selection yields AAV variants for widespread gene transfer to the adult brain. Nat Biotechnol. Feb. 2016;34(2):204-9.
Powell SK et al. Characterization of a novel adeno-associated viral vector with preferential oligodendrocyte tropism. Gene Ther. Sep. 15, 2016.
Tervo et al. A Designer AAV Variant Permits Efficient Retrograde Access to Projection Neurons. Neuron. Oct. 19, 2016;92(2):372-382.
Choudhury et al. In Vivo Selection Yields AAV-B1 Capsid for Central Nervous System and Muscle Gene Therapy. Mol Ther. Aug. 2016;24(7):1247-57.
Keravala A, et al. Evaluating AAV Hybrid Variants for Improved Tropism after Intravitreal Gene Delivery to the Retina. Molecular Therapy, vol. 23, Supplement 1, May 2015, pp. S127-S128.
Vercauteren K, et al. Superior in vivo Transduction of Human Hepatocytes Using Engineered AAV3 Capsid. Mol Ther. Jun. 2016;24(6):1042-9.
Chen M, et al. Efficient Gene Delivery and Expression in Pancreas and Pancreatic Tumors by Capsid-optimized AAV8 Vectors. Hum Gene Ther Methods. Feb. 2017;28(1):49-59.
Ling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016;6:35495.
Earley LF, et al. Identification and Characterization of Nuclear and Nucleolar Localization Signals in the Adeno-Associated Virus Serotype 2 Assembly-Activating Protein. J Virol. Mar. 2015, 89(6):3038-48.
Zou W, et al. Nonstructural protein NP1 of human bocavirus 1 plays a critical role in the expression of viral capsid proteins. J Virol. Apr. 2016;90(9):4658-69.
Mingozzi F, et al. Adeno-associated viral vectors at the frontier between tolerance and immunity. Front Immunol.Mar. 2015, 6:120.
Ling C, et al. Enhanced Transgene Expression from Recombinant Single-Stranded D-Sequence-Substituted Adeno-Associated Virus Vectors in Human Cell Lines In Vitro and in Murine Hepatocytes In Vivo. J Virol. Jan. 2015, 89(2):952-61.
Xie J, et al. Short DNA Hairpins Compromise Recombinant Adeno-Associated Virus Genome Homogeneity. Mol Ther. Jun. 7, 2017;25(6):1363-1374.
Davidsson M, et al. A novel process of viral vector barcoding and library preparation enables high-diversity library generation and recombination-free paired-end sequencing. Sci Rep. Nov. 2016;6:3563.
Chamberlain K, et al. Expressing transgenes that exceed the packaging capacity of AAV capsids. Hum Gene Ther Methods. Feb. 2016;27(1):1-12.

* cited by examiner

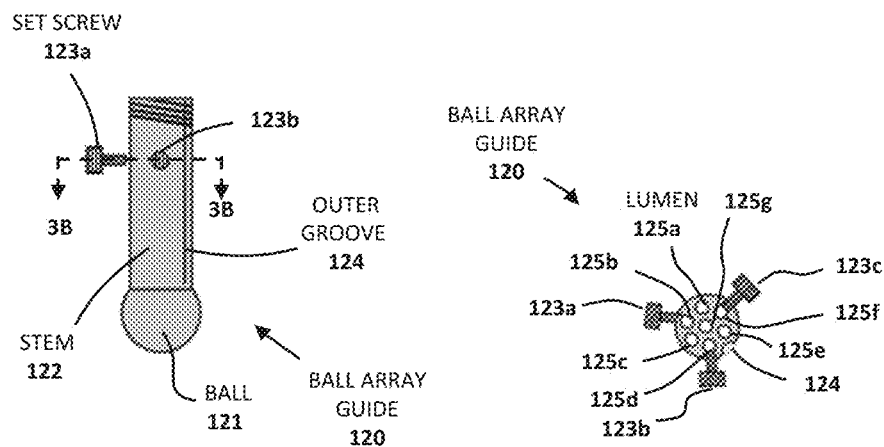
Fig. 3A
Fig. 3B
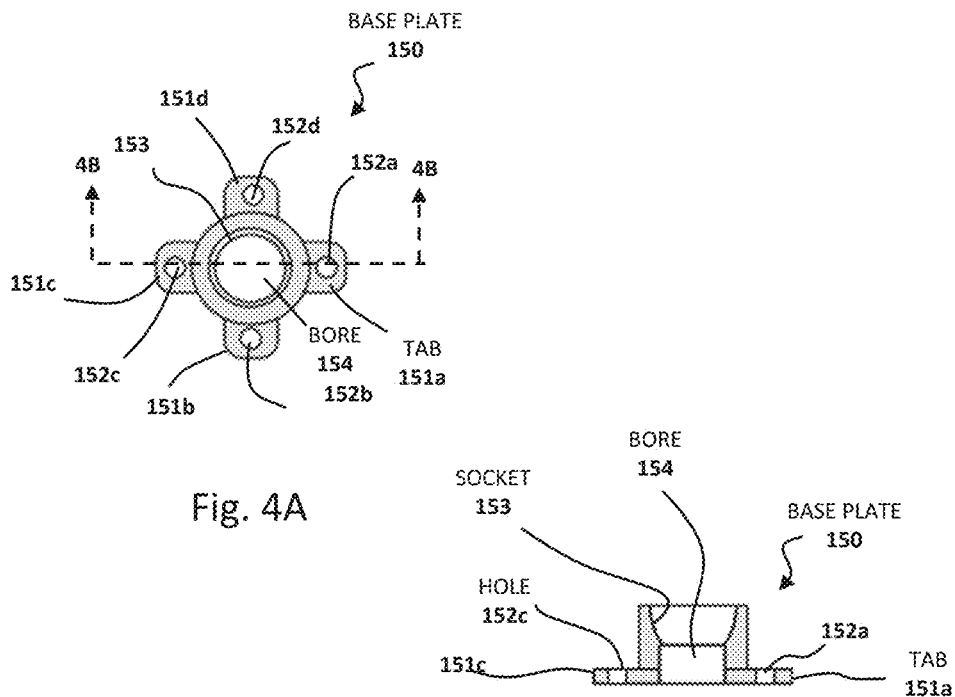
Fig. 4A
Fig. 4B

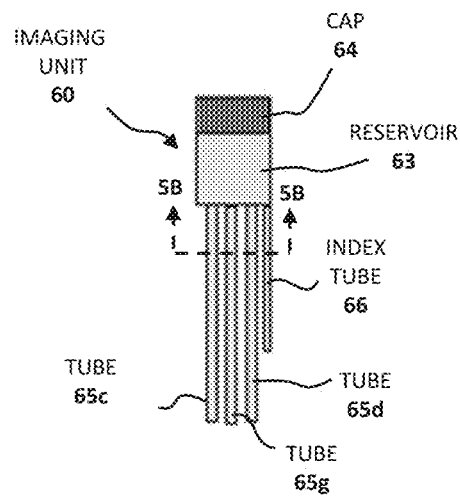
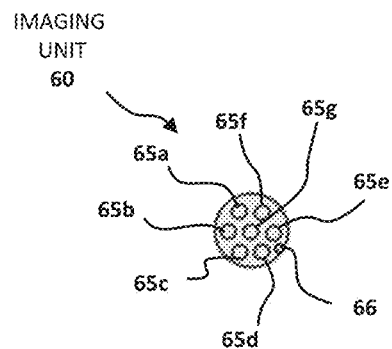
Fig. 5A
Fig. 5B
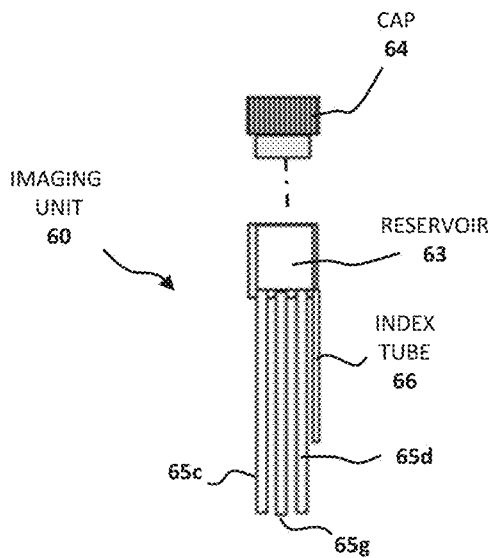
Fig. 5C

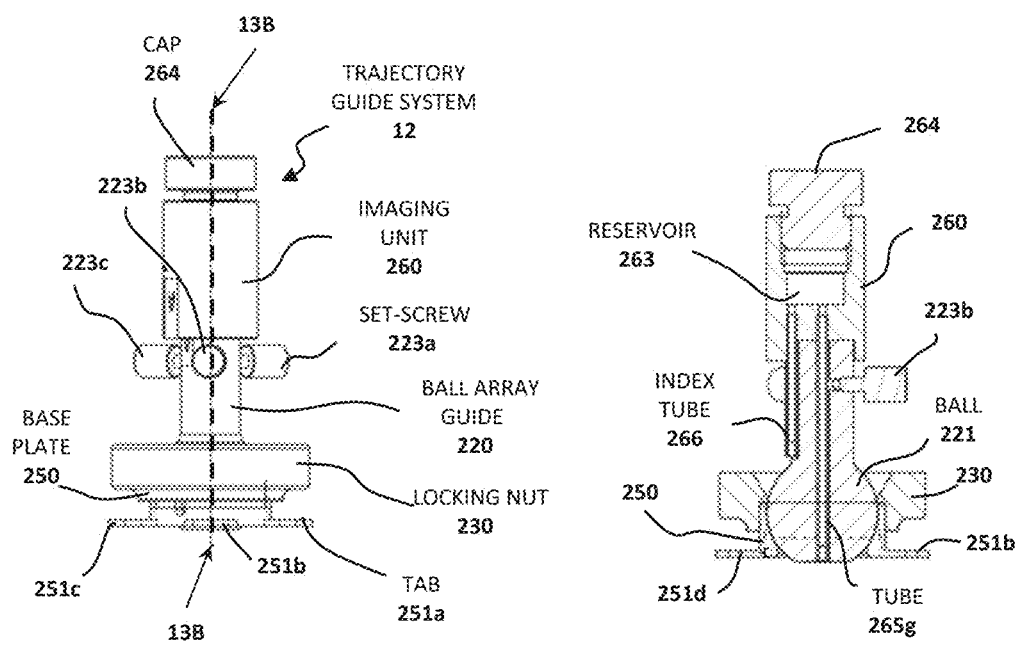
Fig. 13A
Fig. 13B
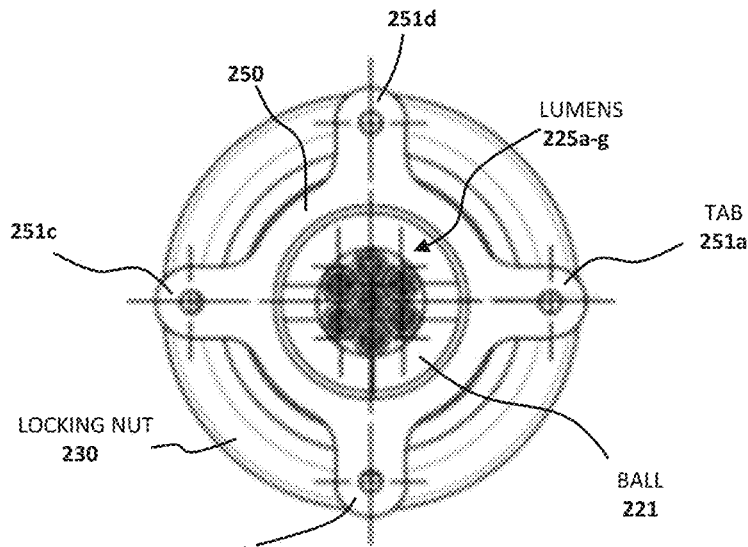
Fig. 13C

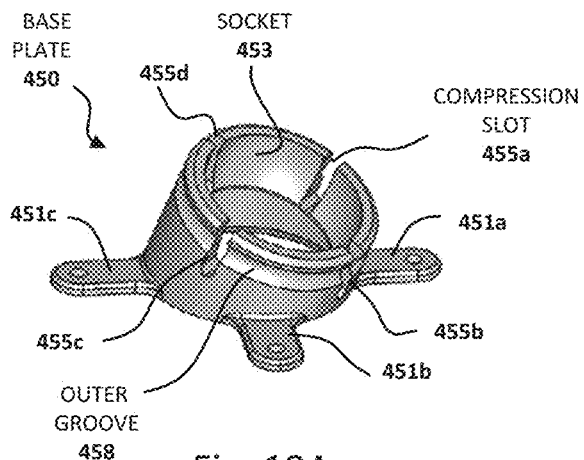
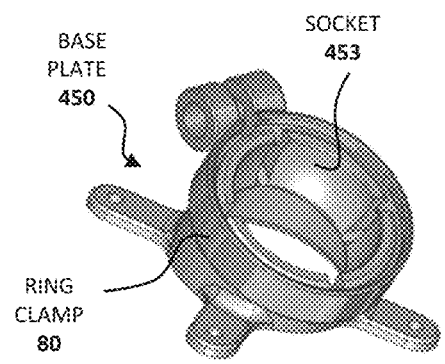
Fig. 19A
Fig. 19B
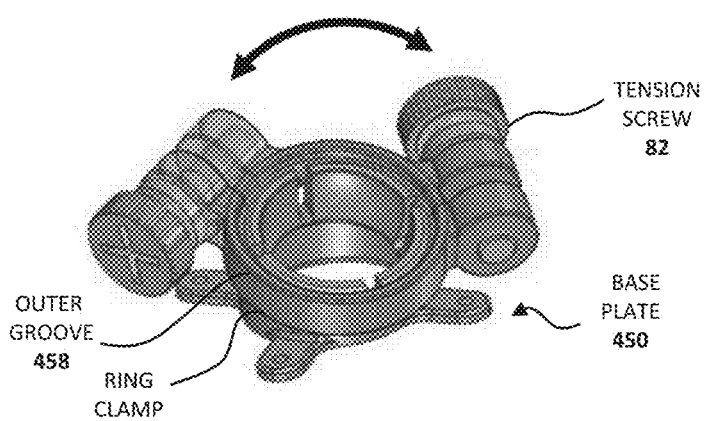
Fig. 19C
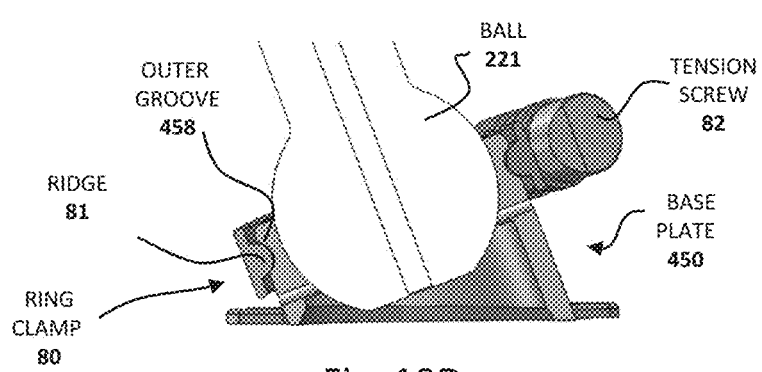
Fig. 19D

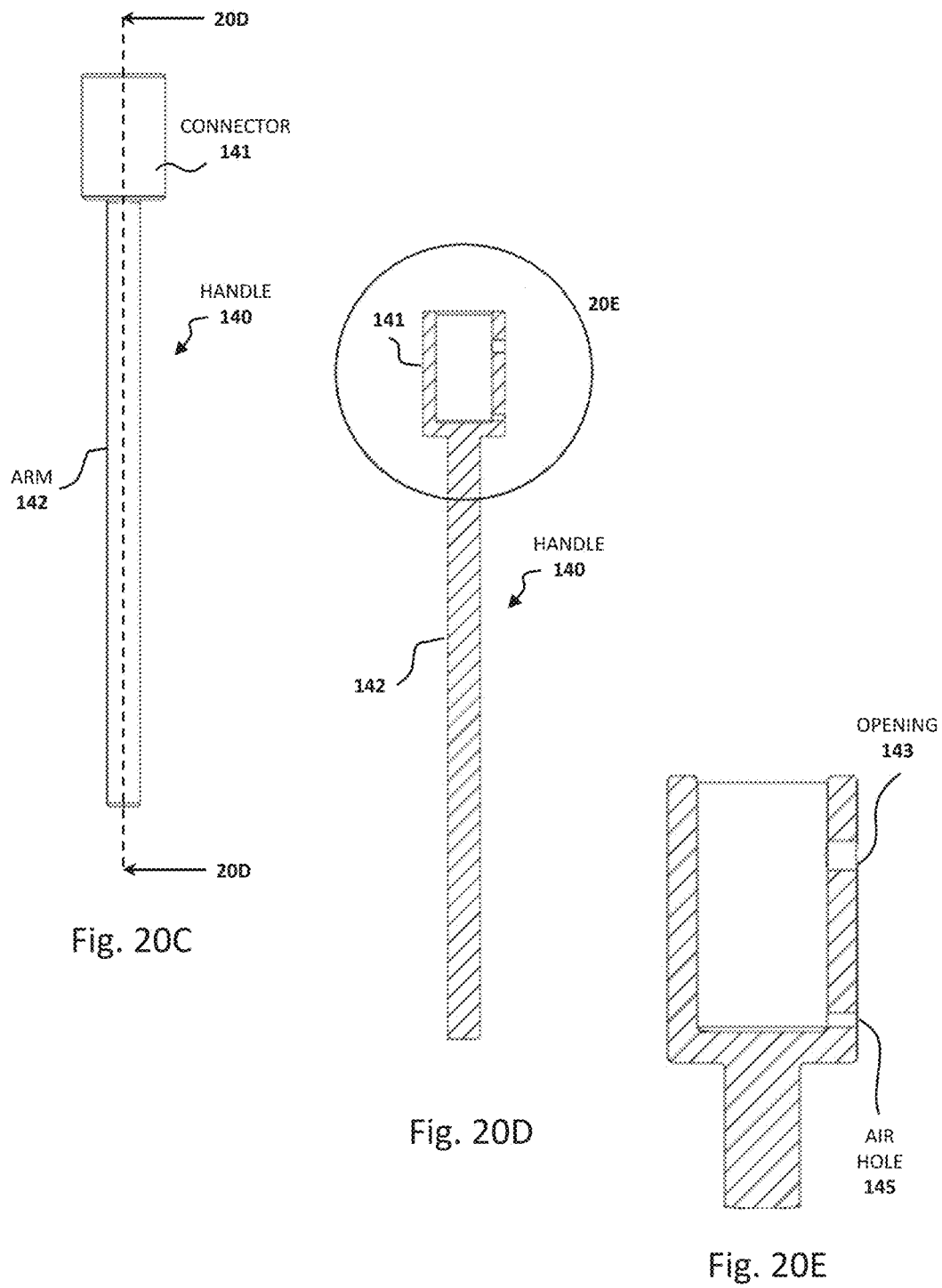

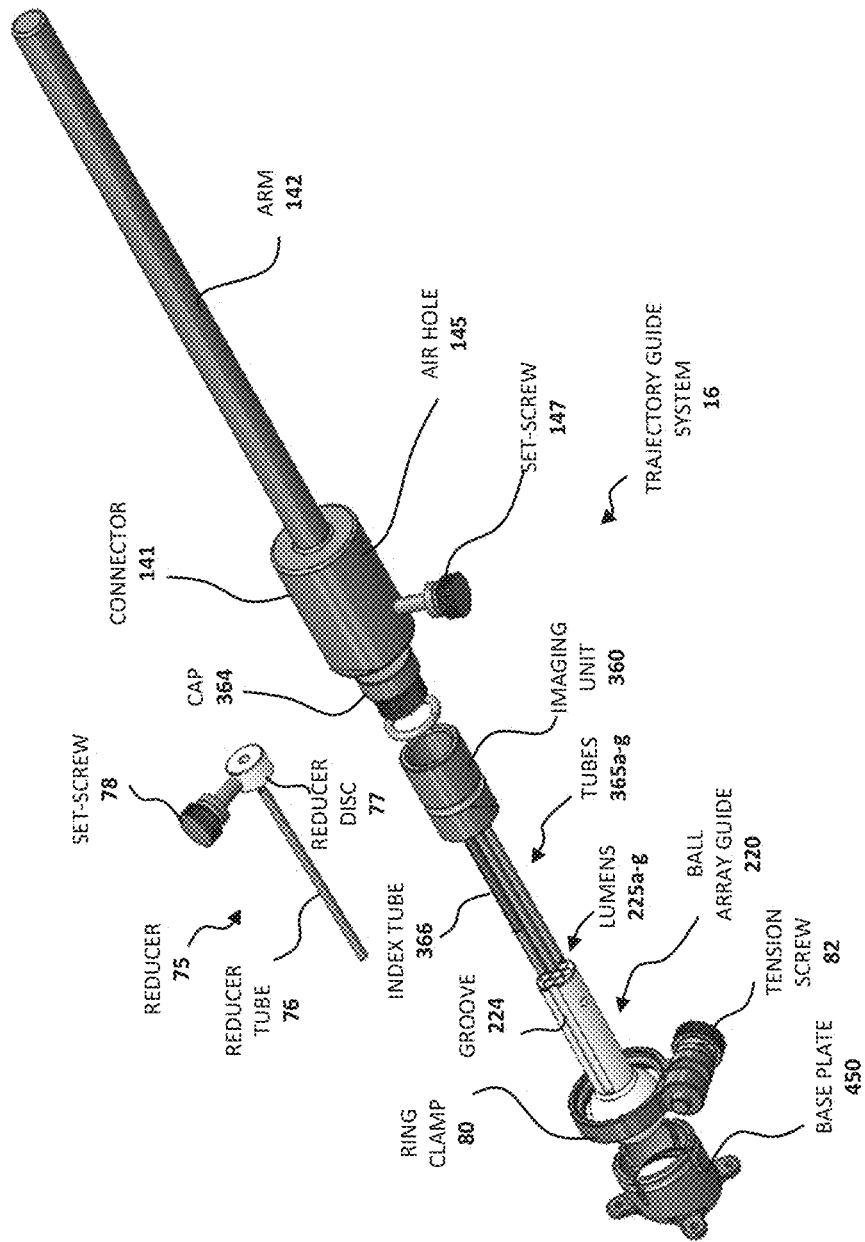

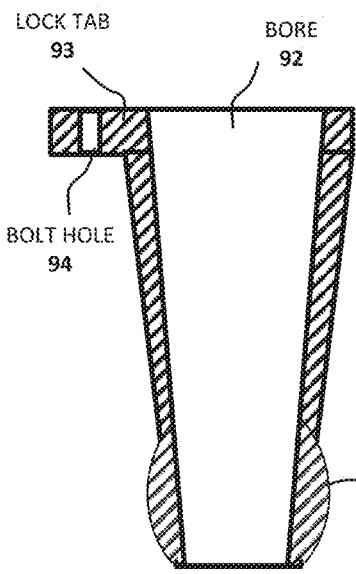
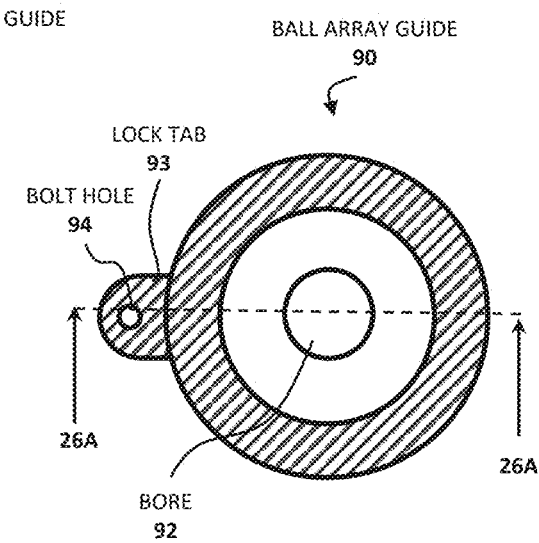
Fig. 26A
Fig. 26B
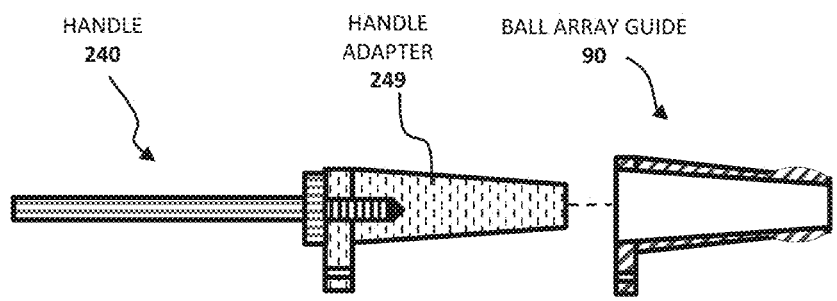
Fig. 26C

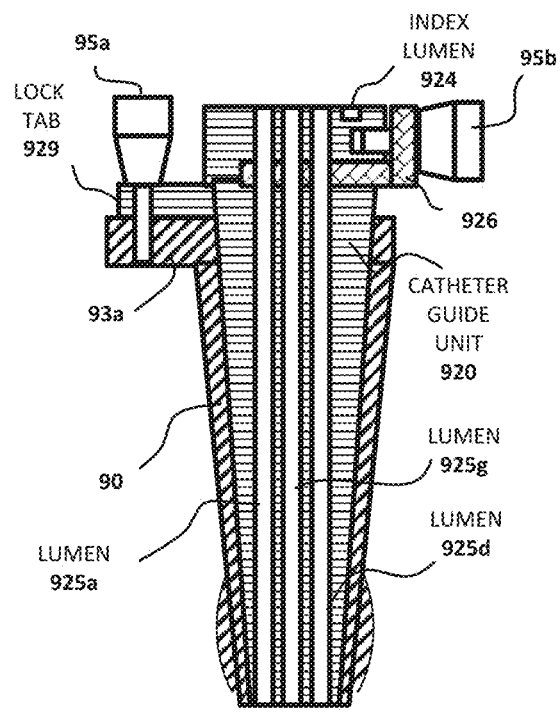
Fig. 26F
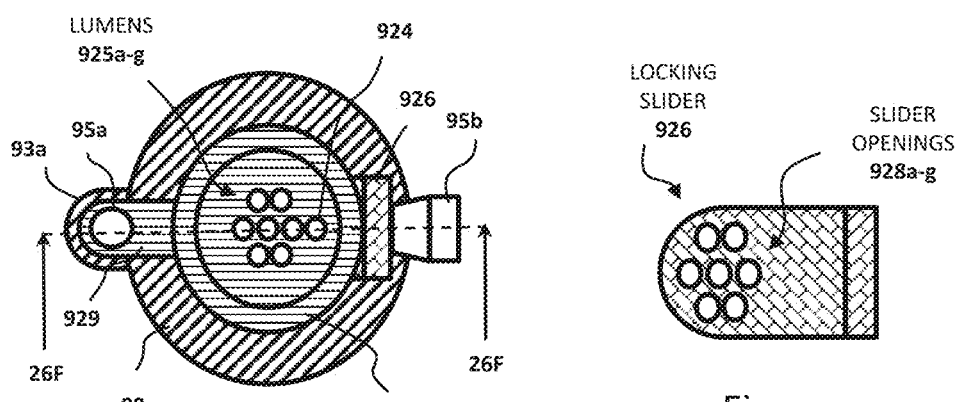
Fig. 26G
Fig. 26H

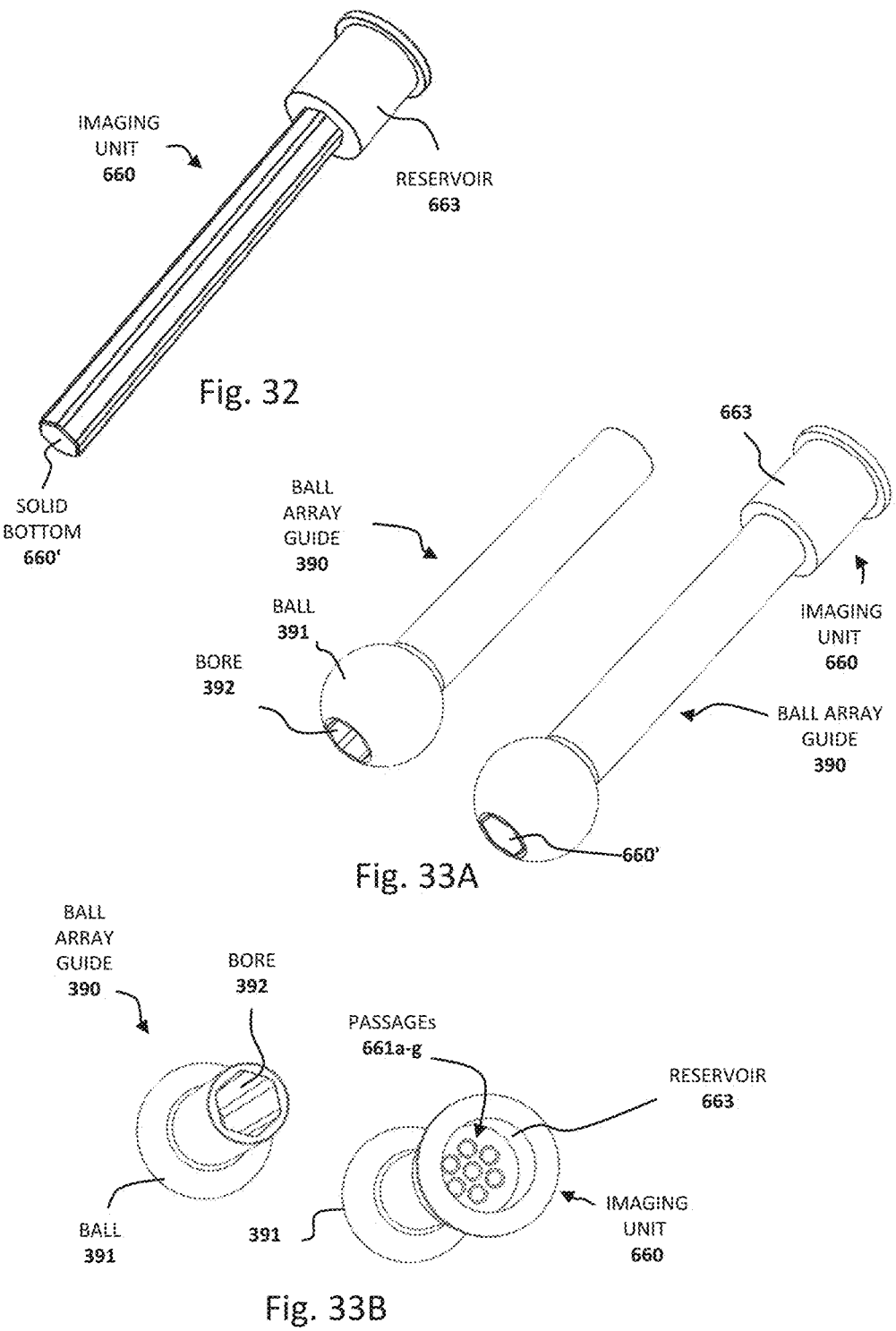

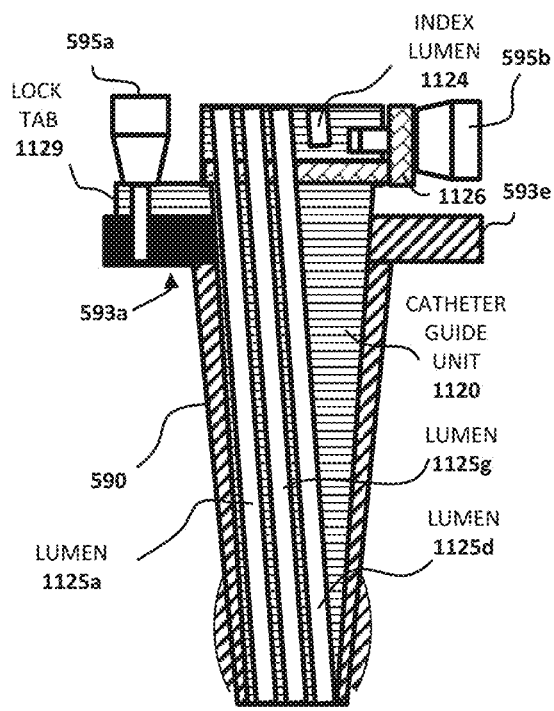
Fig. 36C
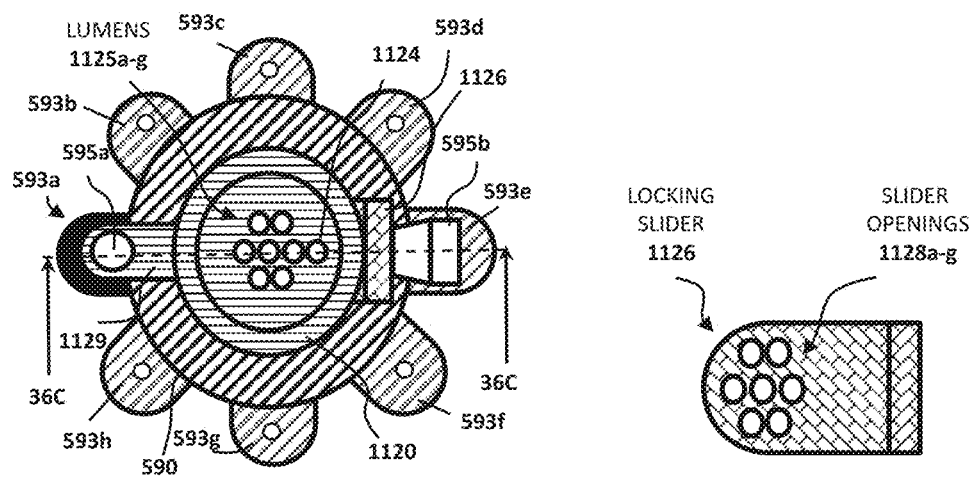
Fig. 36D
Fig. 36E

TRAJECTORY ARRAY GUIDE SYSTEM

CROSS REFERENCE TO RELATED APPLICATIONS

This application is a 35 U.S.C. § 371 U.S. National Stage Entry of International Application No. PCT/US2018/042391 filed Jul. 17, 2018, which claims priority to U.S. Provisional Patent Application No. 62/533,207, entitled Trajectory Array Guide System, filed Jul. 17, 2017 and International Patent Application No. PCT/US2017/049191, entitled Trajectory Array Guide System, filed Aug. 29, 2017; the contents of each of which are herein incorporated by reference in their entirety.

BACKGROUND

The present disclosure relates to brain surgery and more specifically to the field of trajectory array guides for placement of surgical tools used for delivery of therapeutic agents or measurement devices to specific locations in the brain.

Precise access to brain structures is frequently required for an assortment of indications, including tissue sampling, catheter or electrode placement, and localized drug delivery. The most common means of performing these procedures is to use either frame based or frameless stereotaxy. In either case, a preoperative imaging session is performed to characterize and localize the specific brain target. Magnetic resonance imaging (MRI) is the preferred technique for preoperative demarcation of brain structures due to the quality and range of tissue contrast that can be achieved. Utilization of previously acquired imaging information during surgery requires some system for registering the image data to the patient on the operating table. This may be achieved with an external frame that is visible on imaging or the identification of implanted markers or characteristic features in the frameless case. In either situation, target points are determined based on the previously acquired images and are used to guide the surgical procedure. This has disadvantages, as the registration process is imperfect and prone to error, and there is no ability to update the images to compensate for dynamic effects such as brain shift. Moreover, there is no opportunity to either confirm that the surgical goals have been met or to monitor deposition of a delivered therapeutic agent, physiological change or instrument operation during the procedure (Martin et al. *J. Magn. Reson. Imaging*, 2008, 27, 737-743).

An alternative to this traditional means of accessing brain structure is to immobilize the patient's head during imaging and perform the surgery within the magnetic resonance bore. This approach also has obvious disadvantages, most notably the physical presence of the magnet and the corresponding magnetic field. However, it overcomes the need for registration and permits intraprocedural image updates. It also may provide novel insight into the guidance, administration, and evaluation of interventions and therapies. There are several different means of performing stereotactic procedures within an MRI system. Lower field, open systems, afford some degree of line-of-site and therefore instruments can be tracked in a manner analogous to conventional frameless stereotaxy without moving the head out of the MRI system. The orientation of these tracked devices can further be used to prescribe the slice in which imaging is to be performed. In closed bore systems it is much less practical to track devices via optical means. The magnetic resonance environment itself, however, permits opportunities to track and visualize devices either by passive or active means. The latter is achieved by integrating microcoils into the appropriate surgical tools and tracking their position within the bore via MR methods. Passive methods simply require that the device be visible within acquired images either by positive or negative contrast.

Prospective stereotaxy is a technique for aligning a trajectory array guide within a magnetic resonance system. The general approach requires that a patient be immobilized within the magnetic resonance scanner and a trajectory array guide be mounted on a rigid surface such as the skull. Imaging is then performed to define the desired trajectory, usually in two orthogonal planes, from the entry point to the remote target. The trajectory array guide is aligned with real-time imaging followed by confirmatory scans to assure the intended path will be followed. This approach has been used to guide brain biopsy and the insertion of deep brain stimulator electrodes (Martin et al. *J. Magn. Reson. Imaging*, 2008, 27, 737-743).

The optimal trajectory is established by analyzing the magnetic resonance images of the brain, considering the location of the targeted segment of the brain, suitable entry point on the skull, and critical organs and vessels that need to be avoided (e.g. blood vessels) to minimize the risk of complications. Once the trajectory is established, a mounting system external to the head of the patient is used to position the catheter along the trajectory and guide the insertion of the catheter into the brain. This process tends to be iterative and involves image analysis of the actual trajectory of the mounting system versus the desired trajectory. Repositioning of the mounting system is typically required until the actual trajectory coincides with the desired trajectory.

A number of efforts have been made to develop trajectory array guide systems for delivery of elongated tools such as catheters to target locations in the brain. Examples of such systems and related tools are disclosed in U.S. Pat. Nos. 9,042,958, 8,845,665, 7,981,120, 8,845,656, and 8,591,522 and in published U.S. Patent Application Nos. 20150100064 and 20010014771, each of which is incorporated herein by reference in its entirety.

Many challenges remain with regard to development of trajectory array guide systems. A number of such challenges are addressed by various embodiments of the present disclosure.

SUMMARY

The present disclosure provides a trajectory array guide system and kit as well as a method for delivering an elongated tool to a target location in the brain of a subject.

The present disclosure provides a trajectory array guide system for defining a trajectory to a target location in the brain of a subject and for guiding an elongated tool along the trajectory. In some embodiments, the trajectory array guide system includes: a combination of a base and an array guide in a lockable ball-socket pivoting mechanism, wherein the base is configured for attachment to the skull of a subject and the array guide is defined by a series of lumens or is defined by a bore configured to hold a separate array unit defined by a series of lumens; an imaging unit configured for engagement with the array guide and configured to hold and direct imaging fluid along passages which are co-axial with the lumens of the array guide for the purpose of defining a series of trajectories; and an elongated handle having sufficient length for connection to an image-guided stereotaxic navigation system, the handle configured for attachment to either the array guide or the imaging unit.

In some embodiments, the trajectory array guide system includes an array guide. In some embodiments, the array guide includes a ball component. In some embodiments, the trajectory array guide system also includes a base which includes a socket configured to receive and hold the ball of the array guide. In some embodiments, the socket has a central axis orthogonal to a plane formed by the bottom of the base. In some embodiments, the socket has a central axis which is non-orthogonal with respect to the plane formed by the bottom of the base, thereby providing a tilted socket. In some embodiments, the tilted socket increases the angle range of a series of trajectories. In some embodiments, the central axis of the socket is angled by about 10 to about 30 degrees from the axis orthogonal to the plane formed by the bottom of the base.

In some embodiments, the trajectory array guide system includes a socket which has an outer sidewall. In some embodiments, the outer sidewall includes threads or one or more grooves configured for attachment to a locking element. In some embodiments, the locking element prevents pivoting movement of a ball within the socket when the locking element is engaged to the outer sidewall of the socket. In some embodiments, the locking element is a ring-clamp configured for connection to the one or more grooves. In some embodiments, the locking element is a locking nut configured for connection to the threads.

In some embodiments, the trajectory array guide system includes a base which includes a plurality of attachment members. In some embodiments, the plurality of attachment members are accessible by an attachment tool for attaching the base to the skull of a subject.

In some embodiments, the trajectory array guide system includes an array guide which is a generally cylindrical or funnel-shaped member with openings at both ends, having a ball formed at one end and a series of lumens extending longitudinally along the length of the array guide between the openings at both ends. In some embodiments, the series of lumens includes seven substantially parallel lumens with six lumens arranged in a symmetrical hexagonal pattern and a seventh lumen located in the center of the symmetrical hexagonal pattern. In some embodiments, the trajectory array guide system further includes an imaging unit which includes an upper reservoir in fluid communication with a series of lower extensions which are co-axial with the lumens of the array guide. In some embodiments, the lower extensions are tubes configured to fit inside the lumens of the array guide. In some embodiments, the array guide includes an outer groove and the imaging unit includes an index tube configured to slide into the outer groove when the imaging unit is engaged with the array guide. In some embodiments, the index tube is provided as a reference point for identification of each of the tubes in magnetic resonance images. In some embodiments, the imaging unit includes a cap to seal the imaging fluid inside the imaging unit. In some embodiments, the array guide includes a locking mechanism for locking the tubes in place within the array guide. In some embodiments, the locking mechanism includes at least one set-screw which penetrates the array guide and makes tightening contact with at least one of the tubes. In some embodiments, the locking system includes three set-screws, each penetrating the body of the array guide to enter two different lumens as well as the seventh lumen. In some embodiments, the three set-screws are placed closer to the ball of the ball array guide than to the upper end of the ball array guide.

In some embodiments, the trajectory array guide system includes a handle. In some embodiments, the handle includes a connector end configured for attachment to the outside or the inside of an imaging unit. In some embodiments, the connector end is configured for attachment to the outside of the imaging unit and includes an opening for a connector set-screw to lock the handle on the imaging unit. In some embodiments, the handle includes an end spike for insertion into one of the lumens of a ball array guide for direct connection of the handle to the ball array guide. In some embodiments, the handle is at least partially hollow and has an outer end opening at the end opposite the end spike, the outer end opening configured for connection to a navigation pointer of an image guided surgery system.

In some embodiments, the trajectory array guide system includes a reducer tube for insertion into one of the lumens of an array guide. In some embodiments, the reducer tube provides a reduced diameter in the lumen for insertion of an elongated tool. In some embodiments, the reducer tube includes an adjustable stop for restraining movement of an elongated tool.

In some embodiments, the trajectory array guide system includes an array guide defined by a bore configured to hold a guide unit defined by a series of passages which are co-axial with the lumens of the array guide. In some embodiments, the guide unit includes an upper lock tab for connection of the guide unit to the array guide. In some embodiments, the trajectory array guide system includes an imaging unit configured for connection to the array guide at the upper lock tab. In some embodiments, the trajectory array guide system further includes a locking slider configured for insertion into the body of the guide unit to hold an elongated tool in place in one of the lumens.

In some embodiments, the trajectory array guide system includes an imaging unit engaged with a ball array guide. In some embodiments, the imaging unit includes a series of passages connected to a plenum located at about the center of rotation of the ball in a ball array guide. In some embodiments, the trajectory array guide system includes a handle with a channel for injecting imaging fluid into a central passage of the series of passages. In some embodiments, the imaging fluid flows through the central passage into the plenum, with subsequent upward filling of remaining passages of the series of passages via the plenum. In some embodiments, the passages are seven substantially parallel passages with six passages arranged in a symmetrical hexagonal pattern around the central passage. In some embodiments, one of the six passages is extended downward past the plenum for providing an index passage for identification of individual passages.

The present disclosure provides a method for delivering an elongated tool to a target location in the brain of a subject. In some embodiments, the method includes: a) providing a trajectory array guide system which includes a base plate, an array guide, an imaging unit, a handle and an image-guided stereotaxic navigation system connected to the handle; b) performing a craniotomy at an entry location; c) connecting the base of the trajectory array guide system to the entry location and engaging the array guide with the base plate; d) engaging the imaging unit with the array guide and aligning the array guide to the target; e) imaging a series of trajectories towards the target location with magnetic resonance imaging; f) locking the trajectory array guide system and selecting a trajectory from the series of trajectories: g) removing the imaging unit and delivering the elongated tool to the target location using the selected trajectory; and h) removing the trajectory array guide system from the skull of the subject. In some embodiments, the base of the trajectory array guide system is connected to the entry location using bone screws through bottom tabs in the base. In some embodiments, the method includes adding MRI contrast imaging reagent to the imaging unit before the step for imaging the series of trajectories. In some embodiments, the method includes using the stereotaxic navigation system to orient the series of trajectories toward the target location. In some embodiments, the elongated tool is a catheter. In some embodiments, the catheter is configured to deliver a drug to the target location.

In some embodiments, the method for delivering an elongated tool to a target location in the brain of a subject uses a trajectory array guide system of the present disclosure.

The present disclosure provides a kit for assembling a trajectory array guide system. In some embodiments, the kit includes: a base and an array guide which can be connected to form a lockable ball-socket pivoting mechanism, wherein the base is configured for attachment to the skull of a subject, and wherein the array guide is defined by a series of lumens or is defined by a bore configured to hold a separate guide unit defined by a series of lumens; an imaging unit configured for engagement with the array guide and configured to hold and direct imaging fluid along axes which are co-axial with the lumens for the purpose of defining a series of trajectories; and an elongated handle having sufficient length for connection to an image-guided stereotaxic navigation system, wherein the handle is configured for attachment to either the array guide or the imaging unit.

In some embodiments, the kit further comprises instructions for assembly of the array guide system.

In some embodiments, the kit further comprises a container of imaging reagent.

In some embodiments, the kit is for assembly of a trajectory array guide system of the present disclosure. In some embodiments, the trajectory array guide system includes a guide unit for insertion into the bore of the array guide. In some embodiments, the kit includes a plurality of guide units configured for guiding elongated tools of different diameters. In some embodiments, the elongated tools include a catheter.

In some embodiments of the kit, all components of the trajectory array guide system are contained in one or more sterilized packages.

The present disclosure provides trajectory array guide system which can function to provide or assist with the stereotactic guidance, placement and fixation of surgical instruments or devices during the planning and operation of neurological procedures performed in conjunction with pre-operative and perioperative MR imaging. In some embodiments, the procedures can include laser coagulation, biopsies, catheter placement, or electrode placement procedures.

BRIEF DESCRIPTION OF THE DRAWINGS

FIG. 3A is a side view of one embodiment of a ball array guide 120 of the trajectory array guide system 11.

FIG. 3B is a cross-sectional view of the ball array guide 120 of FIG. 3A taken along line 3B-3B of FIG. 3A.

FIG. 4A is a top view of one embodiment of a base plate 150 of the trajectory array guide system 11.

FIG. 4B is a cross-sectional view of the base plate 150 of FIG. 4A taken along line 4B-4B of FIG. 4A.

FIG. 5A is a side view of an imaging unit 60 designed for use in one mode of operation of the trajectory array guide system 11.

FIG. 5B is a cross-sectional view of the imaging unit 60 of FIG. 3A taken parallel to line 5B-5B of FIG. 5A.

FIG. 5C is an arbitrary longitudinal cross-section of the imaging unit 60 with the cap 64 removed.

FIG. 13A is a side elevation view of one embodiment of a trajectory array guide system 12.

FIG. 13B is a cross-sectional view of the trajectory array guide system 12 of FIG. 13A taken along line 13B-13B of FIG. 13A.

FIG. 13C is a bottom view of the trajectory array guide system 12 of FIG. 13A and FIG. 13B.

FIG. 19A is a perspective view of an embodiment of a tilted base plate 450 configured for connection to a ring clamp as shown in FIG. 19B.

FIG. 19B is a perspective view of the tilted base plate 450 of FIG. 19A with a ring clamp 80 attached thereto.

FIG. 19C is a perspective view of the tilted base plate 450 of FIG. 19A with a ring clamp 80 attached thereto and showing the rotational freedom of the clamp 80 around the outer groove 458 of base plate 450.

FIG. 19D is a cross-sectional side elevation view of the tilted base plate 450 and ring clamp 80 showing the ball 221 of a ball array guide held in place.

FIG. 20C is a side elevation view of the handle 140.

FIG. 20D is a cross-sectional view of the handle 140 of FIG. 20C taken along line 20D-20D.

FIG. 20E is a magnified view of the cross-sectional view of the connector 141 of FIG. 20D.

FIG. 25 is an exploded perspective view of an embodiment of the trajectory array guide system 16.

FIG. 26A is a cross-sectional view of an embodiment of a ball array guide 90 which is taken along line 26A-26A of FIG. 26B.

FIG. 26B is a top view of the same embodiment of the ball array guide 90 shown in FIG. 26A.

FIG. 26C is an exploded view indicating connection of a handle 240 to the embodiment of the ball array guide 90 of FIGS. 26A and 26B.

FIG. 26F is a cross-sectional view of embodiment of the ball array guide 90 of FIGS. 26A and 26B with a catheter guide unit 920 attached to the ball array guide 90. This cross-sectional view is taken along line 26F-26F of FIG. 26G.

FIG. 26G is a top view of the ball array guide 90 of FIG. 26F with a catheter guide unit 920 attached to the ball array guide 90.

FIG. 26H is a top view of a locking slider 926 for holding a catheter in place in the catheter guide unit 920.

FIG. 32 is a perspective view of imaging unit 660.

FIG. 33A includes perspective views of an embodiment of a ball array guide 390 having a central bore 392 and an assembly of ball array guide 390 with imaging unit 660.

FIG. 33B includes top perspective views of ball array guide 390 and the assembly of ball array guide 390 with imaging unit 660.

FIG. 36C is a cross-sectional view of an embodiment of a ball array guide 590 with a catheter guide unit 1120 attached to the ball array guide 590. This cross-sectional view is taken along line 36C-36C of FIG. 36D.

FIG. 36D is a top view of the ball array guide 590 of FIG. 36A with an imaging unit 1160 attached to the ball array guide 590.

FIG. 36E is a top view of a locking slider 1126 for holding a catheter in place in the catheter guide unit 1120

DETAILED DESCRIPTION

Figure 1A:
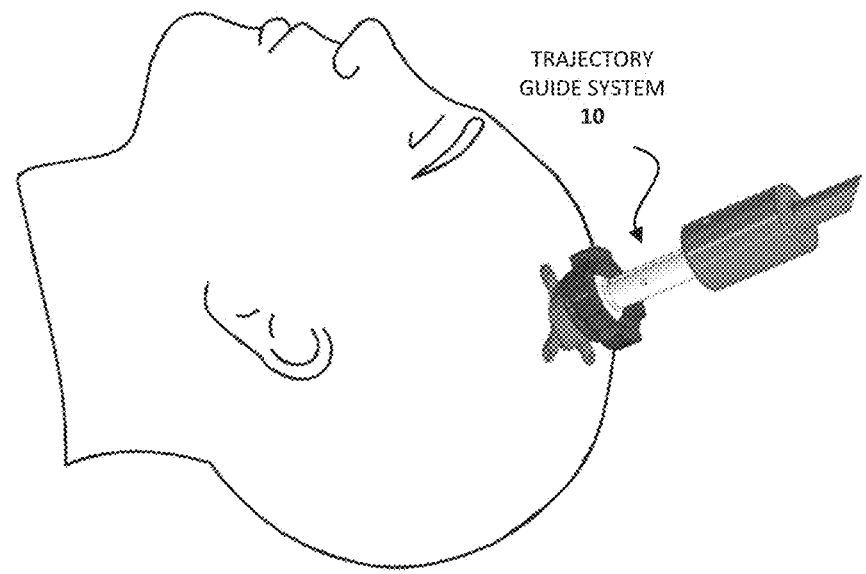
FIG. 1A is an illustration of installment of one embodiment of a trajectory array guide system 10 on the skull of an individual for the purpose of showing one orientation of this system during a mode of operation.

The present disclosure describes embodiments of a trajectory array guide system which is configured to address a number of shortcomings of known trajectory array guide systems. For example, many such trajectory array guide systems currently in use or under active investigation for use in clinical settings tend to be large, cumbersome and have many separate parts which may be expensive to manufacture and which are prone to damage. Such systems tend to have complicated mechanisms for altering and locking the trajectory paths and as such, tend to require more time to make adjustments than is desirable. In some instances, a contributing factor is that trajectory array guide systems are used while a patient is placed in an MRI system outside of an operating room. This situation increases risk of infection and it is thus desirable to complete the surgical procedure as quickly as possible to minimize patient transportation. It is desirable to have the capability to complete the mounting of the trajectory array guide system and establish an optimal locked trajectory within less than one hour.

The present presents embodiments of a trajectory array guide system as well as methods and kits to address these and other disadvantages of presently known systems.

Definitions

As used herein, the term "array guide" refers to a component used to create a series of images of trajectories for insertion of an elongated tool into the brain of a subject and for guiding a path for the elongated tool. The array guide can be adjustable to adjust the angles of the trajectories. The array guide may have an array of lumens formed in its body or alternatively be provided with a wide bore configured for insertion of one or more separate units for creating the trajectories for imaging and guiding of the elongated tool.

As used herein, the term "ball array guide" is an array guide having a ball formed at one end for the purpose of creating a pivoting ball and socket joint for adjustment of the angles of the trajectories.

As used herein, the terms "cannula" and "catheter" are considered synonymous, each referring to a tube constructed for insertion into the body for surgical treatment or for delivers of an external substance or extraction of an internal substance.

As used herein, the term "imaging fluid" refers to a fluid having properties for providing contrast images under a mode of analysis such as magnetic resonance imaging, for example. This term is synonymous with the term "MRI contrast agent." The most commonly used imaging fluids in magnetic resonance imaging include gadolinium-based compounds.

As used herein, the term "imaging unit" refers to a component intended for use with an array guide for the purpose of directing imaging fluid to generate images representing an array of trajectories.

As used herein, the term "image-guided stereotaxic navigation" indicates that images generated by an imaging technology such as magnetic resonance imaging, for example, are used to guide stereotaxic navigation.

As used herein, the term "lumen" refers to an opening or cavity within a body of a system component. More specifically, this term is used to identify channels of an array in an array guide which are provided for guiding the insertion of an elongated tool.

As used herein, the term "passage," like the term "lumen" above refers to an opening or cavity within a body if a system component. More specifically, this term is used to identify channels of an array in an array guide which are provided to deliver imaging fluid to provide trajectory images.

As used herein, the term "plenum" refers to an open space within an otherwise solid body.

As used herein, the term "stereotaxic navigation" refers to provision of three-dimensional navigation within a surgical site using a three-dimensional coordinate system to locate targets within the body and to perform an action such as ablation, biopsy, lesion, injection, stimulation, implantation, radiosurgery or any other surgical procedure.

As used herein, the term "trajectory" refers to a potential pathway. More specifically herein, the term is used to identify potential pathways for insertion of a catheter or cannula into the brain.

Overview of One Embodiment of a Ball Trajectory Array Guide System

The present description presents a ball trajectory array guide system with reference to FIGS. 1A to 8C. A number of alternative embodiments are introduced during the course of this description which may be substituted in various compatible combinations according to the knowledge of persons having ordinary skill in the art to arrive at different embodiments of the present invention.

FIG. 1A illustrates a trajectory array guide system 10 fixed to the skull of a subject for the purpose of showing a one orientation of the system during operation. This placement of the system 10 is shown by way of example only. The placement of the system 10 on the skull will vary according to a number of different factors such as access and avoidance of peripheral equipment as well as the desired trajectory of a surgical tool such as a catheter.

Figure 1B:
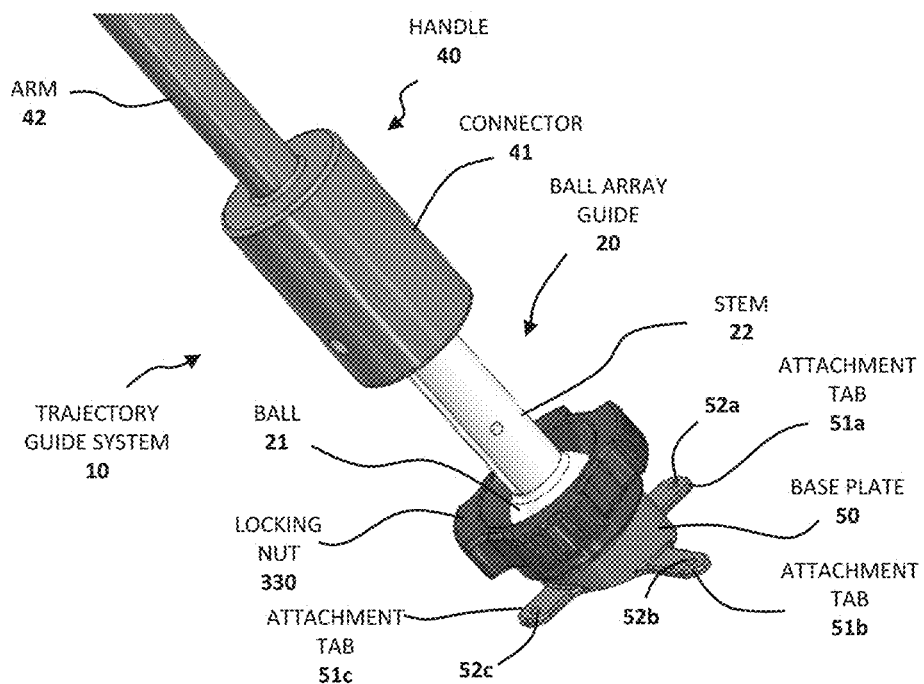
FIG. 1B is a magnified view of the trajectory array guide system 10 of FIG. 1A.

A magnified perspective view of the trajectory array guide system 10 is shown in FIG. 1B. In some cases, the head of the subject can be inside the bore of an MRI system (not shown). In some cases where a standard stereotaxic navigation system is not used to provide initial alignment, the head of the subject may be inside the bore of an MRI system for the entire procedure. The system 10 includes a base plate 50 which has four attachment tabs 51*a-d* with only three (51*a-c*) of the four attachment tabs 51*a-d* visible in this perspective view and with the fourth attachment tab 51*d* hidden from view in this perspective. Each of the four attachment tabs 51*a-d* has a corresponding opening 52*a*-52*d* for insertion of a fastener, typically a bone screw, for fixing the location of the base plate 50 to the skull. The base plate should be located such that an opening made in the skull will be within the central bore of the base plate.

The base plate 50 can include a hollow cup-shaped interior (not shown) acting as a socket to receive the ball 21 of the ball array guide 20. The socket may be designed to provide resistance to the ball such that the array will only move under an externally applied force. One of the advantages of using a ball and socket arrangement is that the socket holds the array in an unlocked state and requires intentional force to adjust the trajectory.

The interior of the ball array guide 20 can include a series of parallel channels or lumens (not shown) which are parallel to the main axis of the ball array guide 20. These parallel channels or lumens can establish an array of parallel trajectories for an elongated surgical instrument, such as a catheter, to enter the brain on a selected trajectory and to reach a desired target location within the brain for delivery of a drug.

The ball-and-socket arrangement allows pivotable movement of the stem 22 of the ball array guide 20. A locking nut 330 with inner threads is provided in this embodiment to be threaded and tightened against outer threads of the base plate 50. Engagement of the locking nut 330 with the out threads of the base plate 50 can compress the socket and prevent pivoting motion of the ball array guide 20 when the desired orientation of the stem is attained.

Also seen in FIG. 1B is a handle 40 with a connector 41 configured for secure attachment to the outward extending end of the ball array guide 20 or to an imaging unit. The connector 41 is joined to an arm 42 which provides an extension of the ball array guide 20 for the purpose of connecting to an image guided stereotactic navigation system. This arrangement allows for manipulation of the position of the ball array guide 20 while viewing a computer monitor with magnetic resonance images of the brain for the purpose of adjusting projected trajectories for catheter placement. Examples of stereotactic navigation systems include: the Varioguide System which is manufactured by BrainLab, AG of Munich; and the Curve Image Guided Surgery system which is manufactured by BrainLab, AG of Munich.

Figure 2:
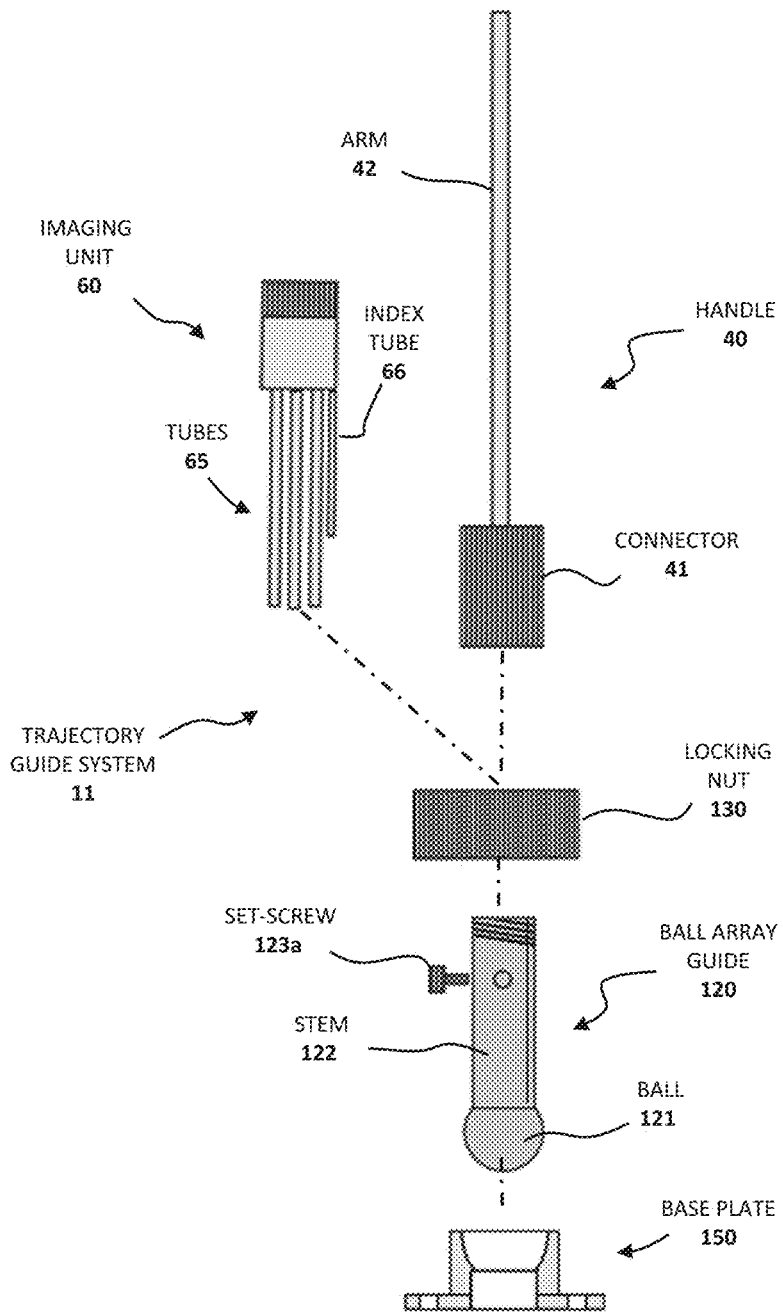
FIG. 2 is an exploded view of an embodiment of a trajectory array guide system 11 which illustrates placement of an imaging unit 60.

FIG. 2 shows an exploded illustration of an embodiment of the trajectory array guide system 11. The ball 121 of the ball array guide 120 is placed inside the socket 153 of the base plate 150. Base plate 150 is shown as an arbitrary cross section for visualization of the shape of the socket 153 (seen in FIG. 4B) formed by an interior sidewall of the bore of the top portion of the base plate 150. The base plate 150 of this embodiment includes a socket axis essentially orthogonal to the plane containing the upper surfaces of the tabs (151*a* and 151*c* seen in FIG. 4B). In contrast to the orthogonal socket axis of the base plate 150 in FIG. 2, the socket axis of the base plate 50 in FIGS. 1A and 1B is tilted away from orthogonality i.e. is non-orthogonal.

The locking nut 130 is passed over the ball array guide 120 and fixed to the upper portion of the outer sidewall of the base plate 150 to lock the orientation of the ball array guide 120. Before or after this step, the imaging unit 60 may be connected to or engaged with the ball array guide 120. The lower portion of the imaging unit 60 has a series of tubes generally labelled in FIG. 2 as 65. While only four tubes are visible in FIG. 2, this embodiment has eight tubes with seven long tubes 65*a-g* and one short tube 66 (shown in FIGS. 5A-C). The seven long tubes 65*a-g* fit inside seven corresponding cavities or lumens (shown in FIG. 3B) in the stem 122 of the ball array guide 120 and the remaining upper portion of the imaging unit 60 remains above the top of the stem 122. In some embodiments, these tubes 65*a-g* and 66 are formed of a thermoplastic polymer such as polyether ether ketone (PEEK) or another polymer having similar properties. The imaging unit 60 can be locked to the ball array guide 120 by three equi-spaced set screws with only one set screw 123*a* shown in FIG. 2 (the remaining set screws 123*b* and 123*c* are seen in the top view of FIG. 3B).

In certain modes of operation, the trajectory array guide system 11 uses the imaging unit 60, In certain modes of operation, the trajectory array guide system 11 does not use the imaging unit 60. In certain modes of operation, both modes (with and without imaging unit 60) will be employed at different points during the procedure.

The connector 41 of the handle 40 is placed over the top of the inserted imaging unit 60 (or without the unit 60 in place) and fixed to the top portion of the ball array guide 120 by threading or another connection mechanism.

FIG. 3A is a similar view of the ball array guide 120 of FIG. 2. In FIG. 3A, a second set-screw 123*b* is present. The ball array guide 120 also includes an outer groove 124 formed in the stem 122 of the ball array guide 120. FIG. 3B is a cross section of the stem 122 of the ball array guide 120 taken along line 3B-3B of FIG. 3A. It is seen that the stem has seven lumens 125*a-g* formed therein. The outer groove 124 is also visible in FIG. 3B as well as the third set-screw 123*c*. The set screws 123*a-c* can penetrate the body of the ball array guide 120 to enter the spaces of lumens 125*b*, 125*d* and 125*f*, respectively. When corresponding tubes 65 of the imaging unit 60 are inserted into these lumens, 125*b*, 125*d* and 125*f*, the set-screws 123*a-c* can be tightened against the outer sidewalls of the tubes 65 to fix the imaging unit 60 in place on the ball array guide 120.

FIG. 4A is a top view of the base plate 150 showing the socket 153, the tabs 151*a-d* and holes 152*a-d*, and the central bore 154. FIG. 4B, which is similar to the view of the base plate 150 in FIG. 2, is a cross section taken along line 4B-4B of FIG. 4A, FIG. 5A is a side view of the imaging unit 60. FIG. 5B is a cross-sectional view of the imaging unit 60 taken along line 5B-5B of FIG. 5A. The imaging unit 60 has a reservoir 63 for filling a series of tubes 65*a-g* and 66 with an imaging fluid, such as a gadolinium-based MRI contrast reagent for example. In some embodiments, the imaging unit includes tubes constructed of a radiopaque material which is visible under MRI and computerized tomography. When the imaging fluid is added to the reservoir 63, it enters all of the tubes 65*a-g* and 66. The imaging fluid within the tubes 65*a-g* can then provide a means of imaging the trajectory paths defined by the axes of the tubes. Tube 66 (the shorter tube) is an indexing tube which is provided outside of the hexagonal symmetry of the other tubes 65*a-g* for the purpose of easily identifying the seven tubes used for imaging the trajectories. In this side view of FIG. 5A, only tubes 65*c*, 65*d*, 65*g* and 66 are visible with the remaining tubes 65*a*, 65*b*, 65*e* and 65*f* being hidden from view. These hidden tubes 65*a*, 65*b*, 65*e* and 65*f* are seen in the cross-sectional view of FIG. 5B which is taken along line 5B-5B of FIG. 5A. Also seen in FIG. 5A is a cap 64 to seal and cover the top of the reservoir 63. FIG. 5C is an arbitrary longitudinal cross-sectional view of the imaging unit 60 with the cap 64 removed.

Figure 6A:
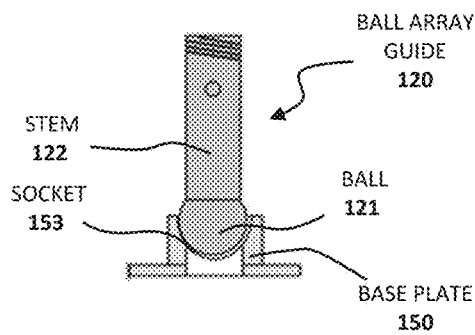
FIG. 6A is a side view of the base plate 150 and the ball array guide 120 with the base plate 150 shown in arbitrary cross section to illustrate a socket 153 of the base plate 150.
Figure 6B:
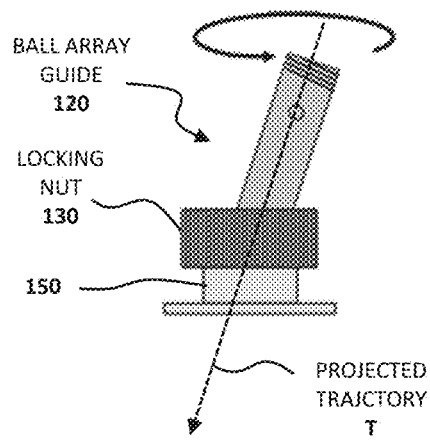
FIG. 6B is a side view of the base plate 150 and the ball array guide 120 with a locking nut 130 in place and indicating pivotable movement of the ball array guide 120 within the base plate 150.

FIG. 6A is a side view illustration of the ball array guide 120 installed in the socket 153 of the base plate 150 prior to installment of the locking nut 130. FIG. 6B shows the same arrangement after installation of the locking nut 130 and additionally shows pivoting rotation of the ball array guide 120 and a projected trajectory T corresponding to one of the lumens 125a-g (not seen in FIG. 6A) in the body of the ball array guide 120.

Figure 7A:
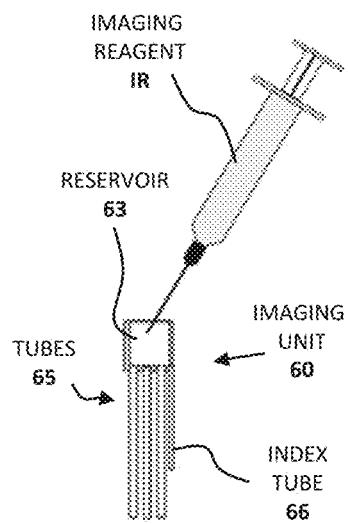
FIG. 7A, FIG. 7B and FIG. 7C illustrate a process for obtaining an array of projected trajectories T using an imaging reagent IR in the imaging unit 60 installed in the ball array guide 120.
Figures 7B, 7C:
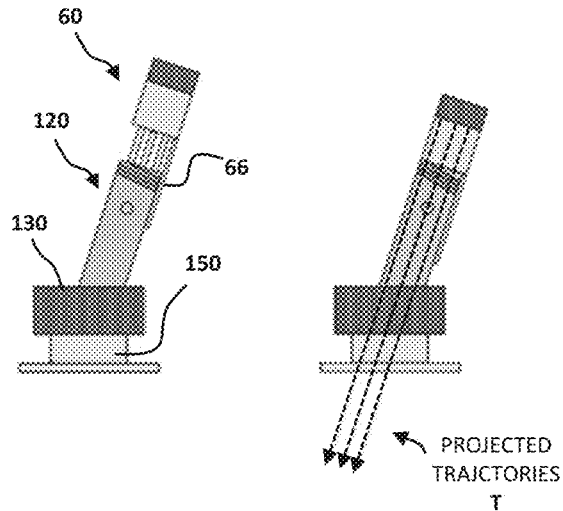

FIG. 7 shows a system and process for defining a series of projected trajectories using the imaging unit 60 in order to identify an appropriate trajectory for insertion of a catheter to reach a target location in the brain (not shown). The tubes 65a-g and index tube 66 of the imaging unit 60 are filled with an imaging reagent IR which subsequently fills the upper reservoir 63. The imaging unit is inserted into the ball array guide 120 with the tubes 65a-g (see FIG. 5B) entering corresponding lumens 125a-g (see FIG. 3B). The index tube 66 slides along the outer groove 124 (see FIGS. 3A and 3B). The imaging unit 60 is fully inserted into the ball array guide 120. The tubes 65a-g and 66 are filled with imaging reagent IR (such as a gadolinium-based contrast reagent which provides a bright white image under MRI) and are used to define a series of projected trajectories T into the brain while the head of the subject is placed in an MRI system. One of the trajectories T is selected for insertion of a catheter (not shown). The image of the bottom of the reservoir 63 serves as an index point or datum to define the insertion depth of the catheter. There is gap of known dimensions between the bottom of the reservoir 63 and the top of the ball array guide 120 due to the thickness of the bottom of the imaging unit 60. The index tube 66 is shorter than the other tubes 65a-g. The image of the index tube 66 (provided by the imaging reagent IR) is used as a reference to correctly identify the individual trajectories T under MRI (which would otherwise be impossible due to the symmetry of the hexagonal pattern of tubes 65a-g). The imaging unit 60 is then removed from the ball array guide 120.

Figures 8A, 8B, 8C:
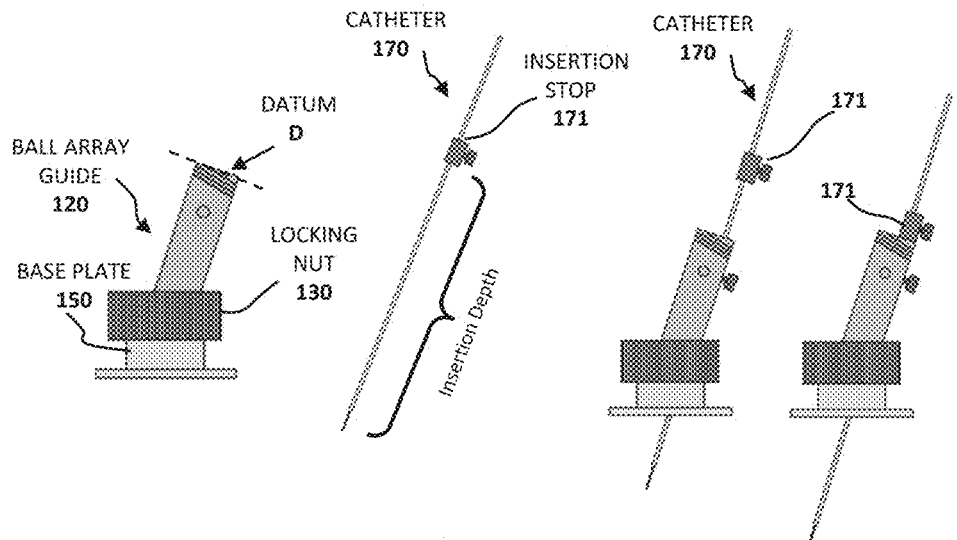
FIG. 8A, FIG. 8B and FIG. 8C illustrate a process for inserting a catheter 170 into one of the lumens of the ball array guide 120 with maximal depth limited by the location of an insertion stop 171.

FIG. 8A-8C illustrates a system and process for insertion of a catheter 170 into the ball array guide 120 after a trajectory is selected and the imaging unit 60 is removed. The free end of the ball array guide 120 serves as the datum D for the depth of insertion of the catheter 170. The structure of the catheter 170 is shown in FIG. 8B. The maximum depth of insertion of the catheter 170 is defined by the location of the insertion stop 171 on the catheter 170. FIG. 8C shows two illustrations of the catheter 170 being partially inserted (left) and fully inserted (right) into the optimal target trajectory as identified by analysis of the trajectory images. In some embodiments, to make the system compatible with 14 and 16-gauge catheters, two separate trajectory arrays with lumens for 14 and 16-gauge catheters can be provided. This will also require two separate imaging units with 14 and 16-gauge tubes, respectively. Alternatively reducing tubes can be used with a 14-gauge array to accommodate small diameter instruments.

As noted above, MRI images of the patient's brain are obtained to guide the overall procedure. Surgical planning is performed by the surgeon using preferred planning software to pre-plan entry sites and catheter trajectories to the target locations in the brain. In addition, MRI systems typically include software for 3D reconstruction of the images and further image analysis including dimensional analysis to obtain locations, dimensions, planes, and trajectories for catheter insertion to the target location. Standard image-guided stereotactic platforms available to neurosurgeons in combination with software provided by the manufacturer are used to guide the entire procedure. From the analysis of the MI scans the following dimensions and landmarks are identified: target location(s): entry point on the skull; a preferred trajectory from the entry point to the target location(s); and insertion depth, which is defined as the distance from the entry point to the target location(s).

Figures 9A, 9B, 9C:
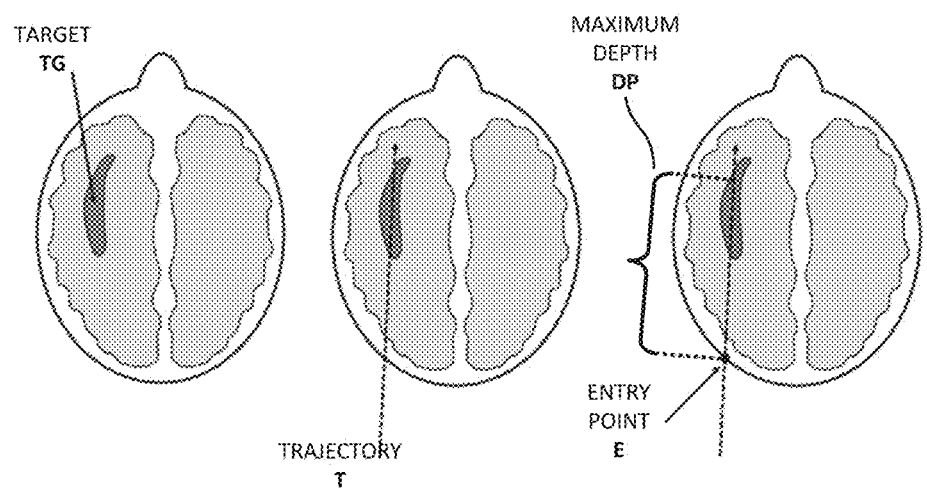
FIG. 9A, FIG. 9B and FIG. 9C illustrate a process for using a trajectory T defined by the trajectory array guide system 11 to reach a target TG at a maximum depth DP in the brain of a patient via an entry point E.

The entry point and trajectory are selected to avoid potential damage to blood vessels and brain sections by the catheter. In some cases, the trajectory is chosen to allow for multiple injections into the target along the pathway of the catheter as illustrated in FIG. 9A-9C.

In some embodiments, components of a trajectory array guide system are sterilized. Suitable sterilization methods for the components include high heat, steam, ethylene oxide or radiation such as gamma sterilization. In some embodiments, components of a trajectory array guide system are made of medical grade materials, including medical grade plastics, medical grade polymers, and medical grade metals. Specific examples of medical grade materials include, but are not limited to: medical grade polyether ether ketone (PEEK); medical grade silicon, medical grade steel (such as medical grade stainless steel); and medical grade aluminum.

Overview of Operation of One Embodiment of the Trajectory Array Guide System

The present disclosure provides a system and method for delivering n elongated tool to a target location in the brain of a subject which uses a trajectory array guide system of the present disclosure. An example describing the operation of a trajectory array guide system 11 is presented with reference to components illustrated in FIGS. 2 to 12C.

Figures 10A, 10B, 10C:
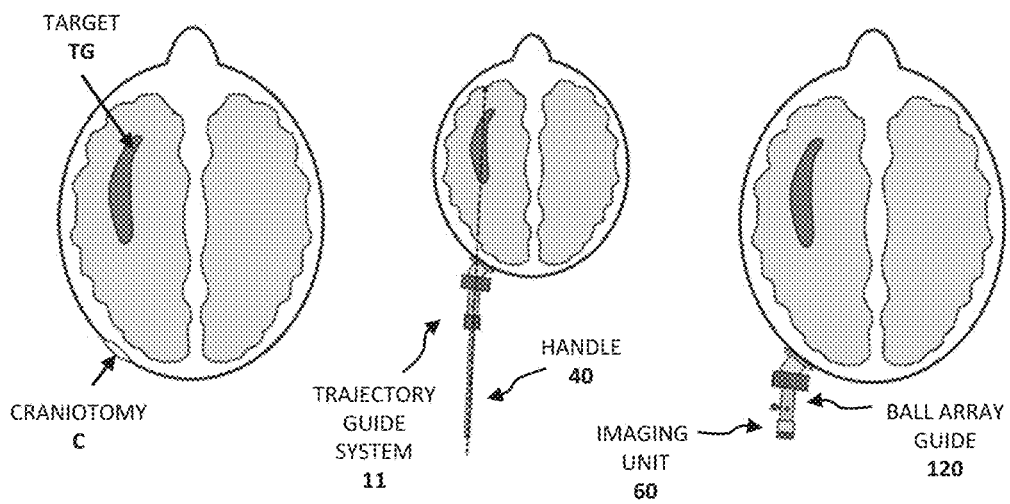
FIG. 10A, FIG. 10B and FIG. 10C illustrate a process for connecting the trajectory array guide system 11 at the site of a craniotomy C.

A patient receives general anesthesia in preparation for the procedure. A head stabilization system is used to avoid head motion during the procedure. The placement of the trajectory array guide system 11 is performed in a sterile environment in a surgical operating room or a hybrid operating room with MRI capabilities. The head is shaven and the desired entry point is marked. The incision site is draped and a skin flap is created with a scalpel to expose the skull for placement of the trajectory array guide system 11. A craniotomy C can be made either at this time (see FIG. 10A) or after placement of the base plate 150. The ball array guide 120 is loosely mounted onto the base plate 150 and the handle 40 is connected to the trajectory array guide system 11. The imaging unit 60 filled with gadolinium imaging reagent IR is inserted into the ball array guide 120. The assembled trajectory array guide system 11 (see FIG. 2) is then connected via the handle 40 to a guiding system such as the VarioGuide navigation system to correctly orient the trajectory array to the pre-determined trajectory (FIG. 10B).

Once a suitable orientation of the trajectory array guide system 11 is established, it is lowered to the surface of the skull and the base plate 150 is secured onto the skull by securing up to four bone screws into the four holes 152a-d of the tabs 151a-d of the base plate 150. If a craniotomy was not previously made, the upper portion of the trajectory array guide system 11 including the handle 40 is removed from the socket of the base plate 150 to allow access through the base plate 150 to make a burr hole in the skull according to known surgical procedures. The trajectory array guide system 11 is then reattached to the base plate 150 with proper alignment confirmed by the stereotactic navigation system. The locking nut 130 is then tightened to preserve the orientation and prevent any further movement between the system components. The handle 40 is disconnected from the stereotactic navigation system and removed, as shown in FIG. 10C. In case of a hybrid surgical suite, the patient is ready for MR imaging. In case of a separate imaging suite, the incision site and trajectory array guide system 11 are covered with a sterile drape and the patient is transported to the imaging suite.

As an alternative workflow, it is envisioned that the entire procedure could be performed within an MRI scanner without use of an alternative imaging system to align the trajectory array guide system 11. Some alternative navigation system, or MRI sequences, will be needed to identify the entry point for attachment of the base plate but alignment of the trajectory array guide system 11 would be performed entirely as described below for refinement of the trajectory.

Figures 11A, 11B, 11C:
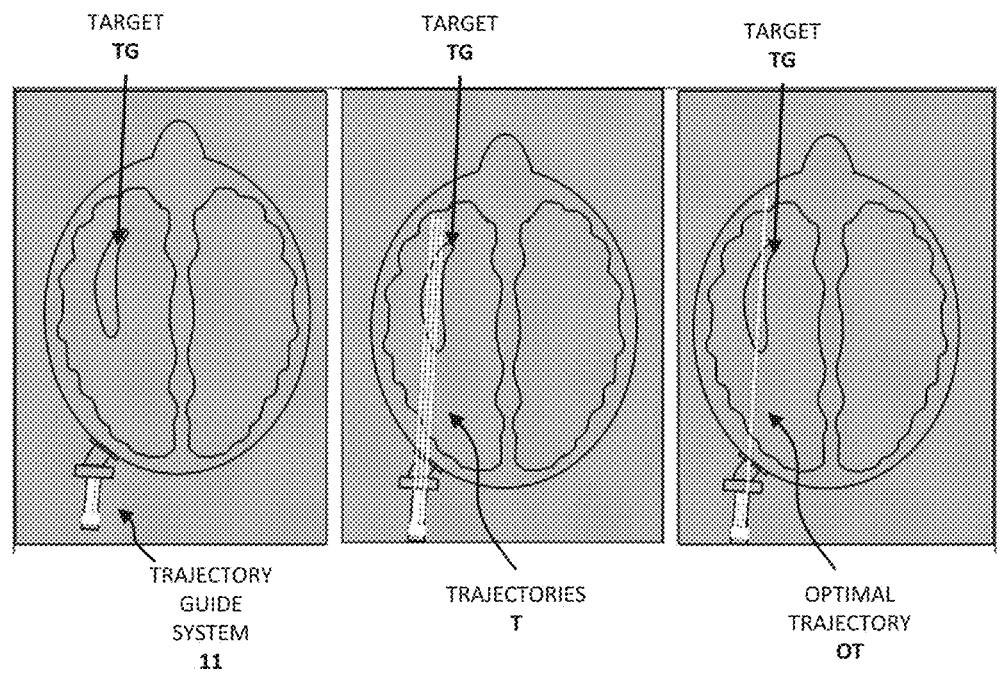
FIG. 11A, FIG. 11B and FIG. 11C illustrate a process for using the trajectory array guide system 11 to generate an array of trajectories T in an effort to define an optimal trajectory OT to a target TG.

MRI scans of the patient's brain are performed to confirm that the correct entry point and trajectory have been established. FIGS. 11A-11C illustrate the MR imaging and analysis procedure. An illustration of a magnetic resonance image of the brain of the patient and the trajectory array guide system 11 mounted on the skull. The imaging reagent IR contained in the reservoir 63 and tubes 65*a-g* and 66 of the imaging unit 60 provides bright white images on the MRI scan (see FIG. 11A). 3D reconstruction and subsequent image analysis on the MRI scanner console is used to determine the sagittal and axial plans of each trajectory and to project the trajectories T originating from the tubes 65*a-g* and 66 of the imaging unit 60 into the brain toward the target location TG (see FIG. 11B). The optimal trajectory OT is selected from the array of possible trajectories T (see FIG. 11C). While it is helpful to use the central lumen 125*g* for initial alignment, the surrounding lumens 125*a-f* provide alternative parallel trajectories T which can be employed if required. The image of the index tube 66 serves as a directional reference to identify each individual lumen in the array of lumens 125*a-g* in the ball array guide 120. If none of the trajectories T is deemed suitable, the direction of the trajectories T can be adjusted by loosening the anchor lock nut 130 to allow pivoting movement of the ball array guide to provide an improved series of trajectories T. The ball array guide 120 should not move without intentional force when the lock nut 130 is loosened. Then the ball array guide 120 is tightened with the lock nut 130 to secure the new orientation. The MR imaging and analysis procedure is then repeated.

Figure 12A:
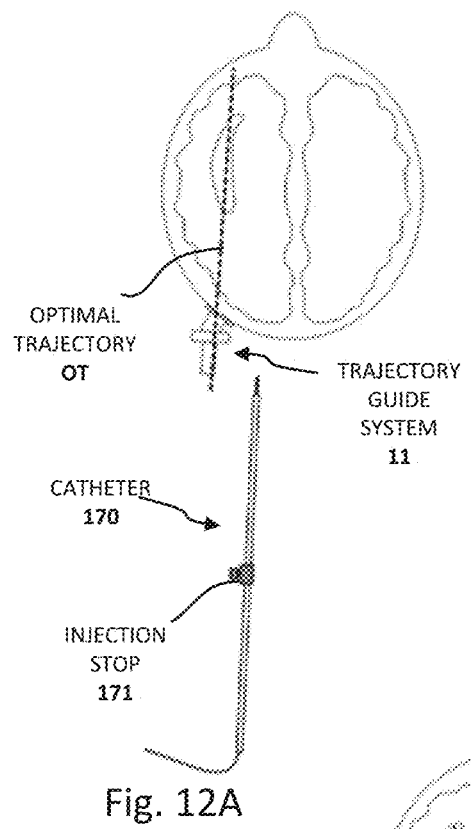
FIG. 12A, FIG. 12B and FIG. 12C illustrate a process for insertion of a catheter 170 into the trajectory array guide system 11 to deliver a drug to the target TG.
Figure 12B:
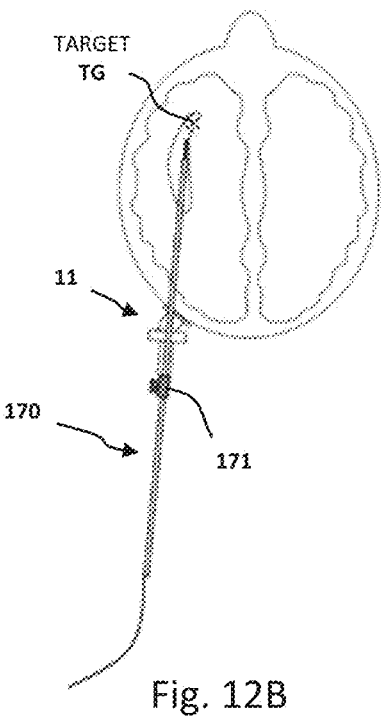
Figure 12C:
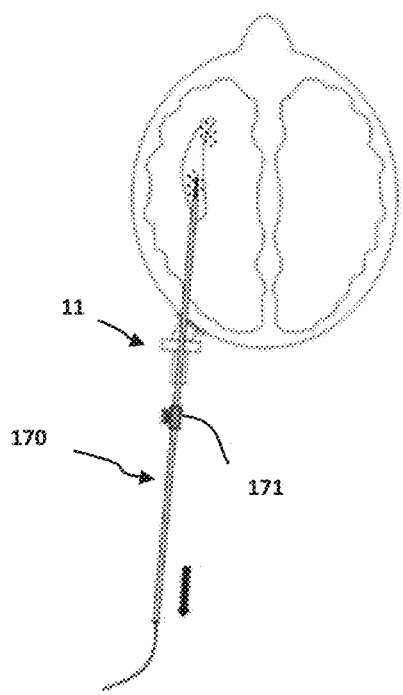

When the optimal trajectory is confirmed, the imaging unit 60 is removed from the ball array guide 120. From the MRI images the initial and maximum depth of insertion of the catheter 170 is measured using the base of the reservoir of the imaging unit 60 as the datum (a correction equal to the thickness of the imaging unit base must be made). A depth insertion-stop 171 is mounted on the drug delivery catheter 170 at a distance from the tip of the catheter 170 equal to the maximum insertion depth as shown in FIG. 12A (see also FIGS. 8A-8C) and a distance equal to the initial depth is marked onto the catheter 170 with a sterile pen. The catheter 170 is carefully inserted through one lumen of the array of lumens 125*a-g* in the ball array guide 120 to the initial target depth and secured by a lock screw which is configured to penetrate all lumens 125*a-g* of the ball array guide 120, The correct position of the tip of the catheter 170 is confirmed by MRI and the drug is injected (see FIG. 12B). The catheter 170 is then withdrawn as shown in FIG. 12C. In situations where one or more targets along the optimal trajectory OT can be reached before the insertion stop 171 prevents further insertion, additional boluses of drug may be injected at these targets. Likewise, such targets may receive injections with pausing during the phase of retraction of the catheter 170.

The trajectory array guide system 11 is removed from the skull by removing the bone screws. The wound is closed using standard surgical techniques.

One embodiment of a procedure sequence will now be briefly outlined. This procedure sequence assumes that the entire system 11 may be assembled prior to mounting to the skull of the subject.

First the entire trajectory array guide system 11, including the imaging unit 60 and the handle 40, is assembled. Then a surgical navigation system is connected to the handle 40. The entry location on the skull is identified and a craniotomy C is performed to expose the entry location. Then the base plate 150 is connected to the skull. The handle 40 is removed to add imaging reagent IR to the trajectory array guide system 1*ii*. MRI scans are then performed to view the projected trajectories T and the optimal trajectory OT is selected. The handle 40 is reattached to facilitate additional manipulation of the optimal trajectory OT, if required. The imaging unit 60 is then removed with confirmation that the selected optimal trajectory OT remains locked in place. The catheter procedure is performed using the optimal trajectory OT and then the system 11 is removed from the subject.

In some embodiments, the screw holes of the base plate can be directly accessed by a screwdriver during the process of assembly and disassembly.

Commonly used magnetic resonance imaging has a spatial resolution of about 1 mm. Therefore, in some embodiments, the trajectories in the array are spaced between about 1 mm to about 3 mm apart; between about 1.5 mm to about 2.5 mm apart; about 2 mm apart; about 2.15 mm apart; about 2.25 mm apart; or about 2.35 mm apart.

Base Plate and Locking Nut Combination

FIGS. 13A-13C show an embodiment of trajectory array guide system 12 in which a locking nut 230 is disposed directly above screw holes in the tabs 251*a-d* of the base plate 250 once the system 12 is assembled. FIGS. 13A-13C also show the system 12 with an imaging unit 260, a ball array guide 220 including the ball 221, lumens 225*a-g* and set screws 223*a-c*, as well as features of the imaging unit 60 including the reservoir 263, tubes 265*g* and 266, and cap 264.

Figure 14A:
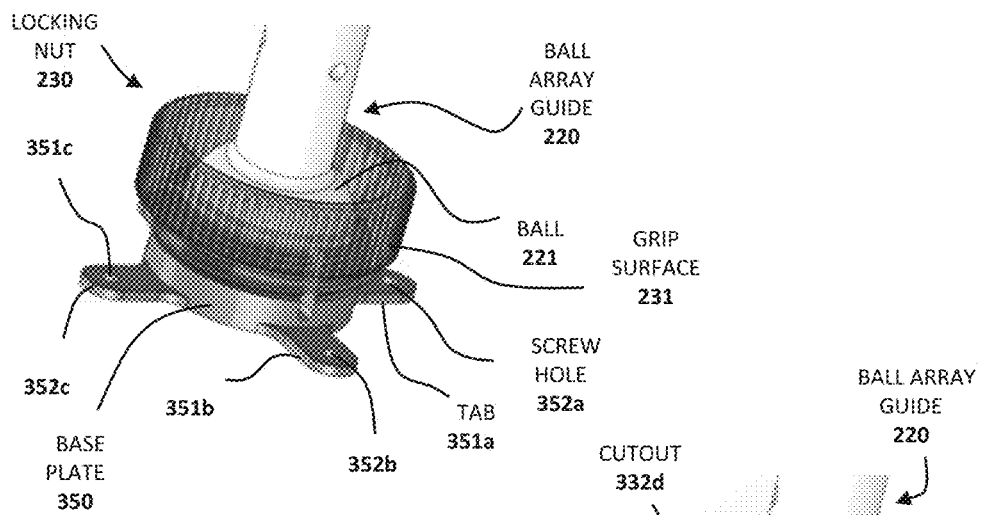
FIG. 14A is a perspective view of a ball array guide 220 held and locked in place in a base plate 350 with a ring-shaped locking nut 230 having a grip surface 231.
Figure 14B:
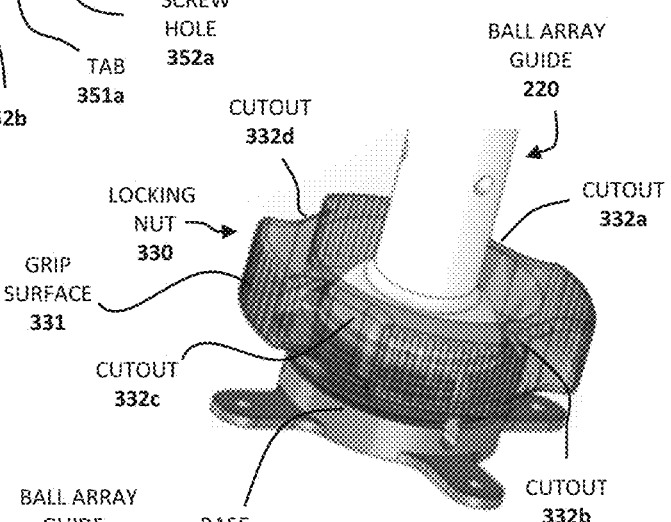
FIG. 14B is a perspective view of a ball array guide 220 held and locked in place in a base plate 350 with a locking nut 330 having cutouts 332a-d.
Figure 14C:
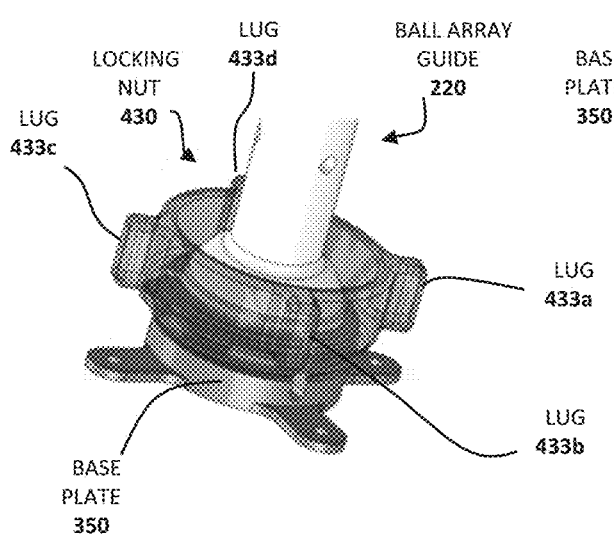
FIG. 14C is a perspective view of a ball array guide 220 held and locked in place in a base plate 350 with a locking nut 430 having opposing lugs 433a-d.

In certain embodiments, a trajectory array guide system can be assembled prior to mounting onto a skull. In certain embodiments, the trajectory array guide system provides unobstructed access to the screw holes in the base plate to place the bone screws. The images in FIG. 14A to 14C show three alternative embodiments that provide unobstructed access to the screw holes of the tabs. In all three embodiments, the base plate 350 is identical and the screw holes 352*a-d* of the tabs 351*a-d* are moved radially outward by 2 mm, thereby increasing the footprint of the base plate by 4 mm (tab 351*d* with screw hole 352*d* is not visible in the perspective views of FIGS. 14A-14C). While base plate 350 is illustrated in FIGS. 14A-14C, other base plate embodiments, such as the tilted base plate 50 of FIGS. 1A and 1B, for example may be substituted for base plate 350.

In FIGS. 14A-14C, the locking nut is modified differently in each of the three illustrated embodiments to provide convenient access to the screw holes 352*a-d* of the tabs 351*a-d*.

In FIG. 14A, the locking nut 230 is the same as in FIGS. 13A to 13C and has a grip surface 231 to facilitate application of tightening and loosening force.

In FIG. 14B, the locking nut 330 is modified relative to locking nut 230 to include four cutouts 332*a-d* to provide additional space for access of a screwdriver to the screw holes 352*a-d* in the tabs 351*a-d* of the base plate 350. This embodiment 330 of the locking nut also has a grip surface 331.

In FIG. 14C, the locking nut 430 is provided with four equi-spaced lugs 433a-d to facilitate application of tightening/loosening leverage against the locking nut 430.

Tilted Base Plate

Figure 15A:
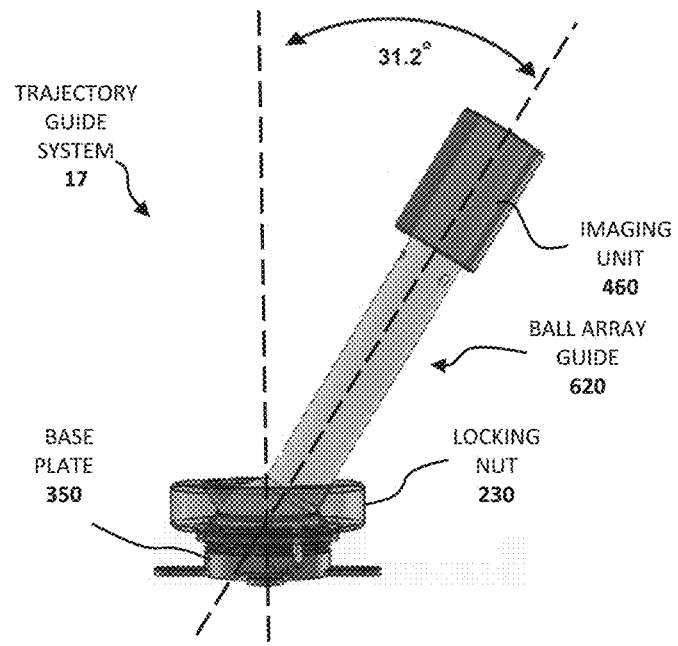
FIG. 15A is a side elevation view of an embodiment of a trajectory array guide system 17 indicating that the locking nut 230 limits the angle of trajectory of the ball array guide 620.

In certain procedures, it is favorable to enter the skull at angles of up to about 45 degrees from the central orthogonal axis of a base plate. FIG. 15A illustrates a trajectory array guide system 17 which includes a ball array guide 620 and imaging unit 460. The trajectory array guide system 17 also includes a flat base plate 350 with an orthogonally-directed socket and a locking nut 230. The angular range of the trajectory array guide system 17 shown in FIG. 15A is limited by the flat base plate 350 and the locking nut 230, and is only about 30 degrees from the centerline.

Figure 15B:
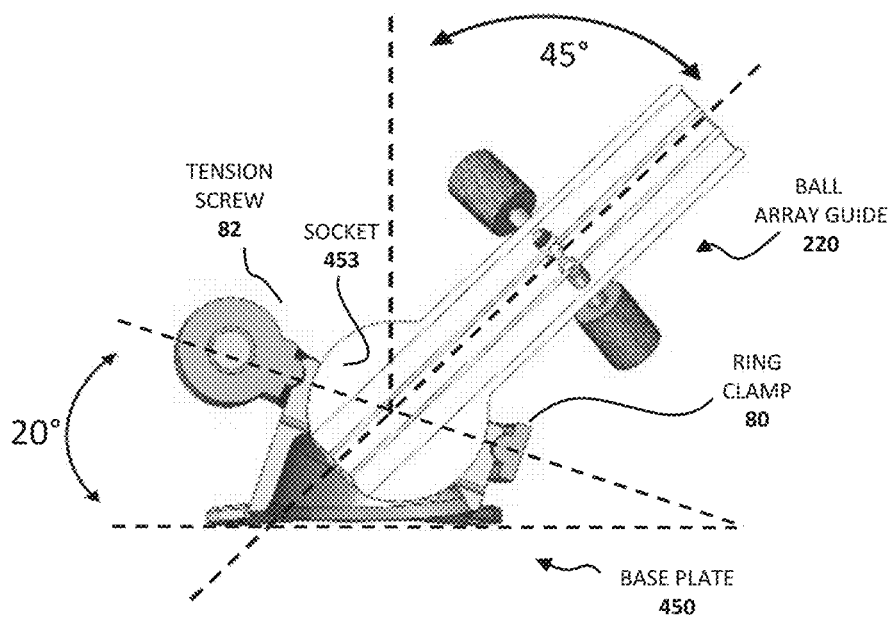
FIG. 15B is a cross section view of a trajectory array guide system which includes a tilted base plate 450.

FIG. 15B illustrates a trajectory array guide system which includes a ball array guide 220 and a base plate 450 which includes a socket 453. The axis of the socket 453 relative to the base plate 450 is tilted by about 20 degrees with a with a ring clamp 80. This tilt provides the capability of expanding the range of trajectory angles up to about 45 degrees from normal centerline.

Figure 16:
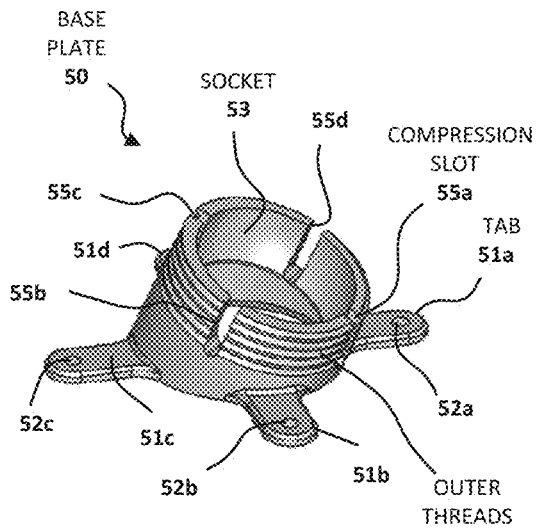
FIG. 16 is a perspective view of an embodiment of a base plate 50 whose socket 53 is tilted to provide larger angles of trajectory.

FIG. 16 shows an embodiment of a base plate 50. The base plate 50 is tilted and includes the four tabs 51a-d with screw holes 52a-d (screw hole 52d is hidden from view in this perspective). The outer sidewall of the socket 53 is provided with outer threads 54 for coupling to inner threads of one or more different embodiments of a locking nut (not shown in FIG. 16). Also seen in FIG. 16 are four compression slots 55a-d which are provided to provide the socket with additional flexure to improve tightening of the locking nut against the outer sidewall of the socket 53. The slots 55a-d make the circumference of the socket 53 less rigid and therefore more easily compressed against the ball of the ball array guide. The bottom of the center bore of the base plate 50 is provided with a chamfer (not shown) to avoid interference of the catheter with the inner rim of the base plate at significantly large angles relative to the axis which is orthogonal to the plane formed by the bottom of the plate.

Figure 17:
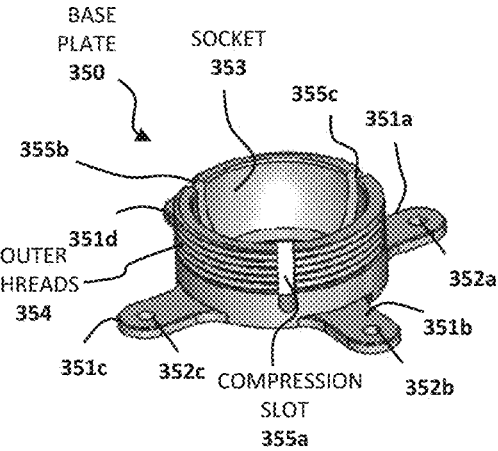
FIG. 17 is a perspective view of base plate 350 whose socket 353 is orthogonal to the plane of the tabs 351a-d.

For comparison. FIG. 17 shows an embodiment of a base plate 350. This embodiment 350 has a socket 353 with an axis which is orthogonal to the plane containing the four tabs 351a-d as well as outer threads 354 and three compression slots 355a-c. As noted above with reference to FIGS. 15A-15B, this embodiment 350 of the base plate is limited to trajectory angles at or less than 31.2 degrees.

In some embodiments, a base plate of the present disclosure can have a bore diameter of between about 20 mm to about 50 mm, between about 30 mm to about 40 mm, or a bore diameter of about 35 mm.

In some embodiments, a kit of the present disclosure includes a trajectory array guide system which includes only a tilted base plate. In some embodiments, the trajectory array guide system includes only a flat base plate.

Locking Nut Modifications and Alternatives

FIGS. 14A to 14C show the ball 221 of the ball array guide 220 locked into the socket 353 of the base plate 350 by different embodiments of locking nuts 230, 330 and 430 which allow access of an attachment tool such as a screwdriver to the holes of the attachment tabs 351a-d. In each of these three embodiments 230, 330 and 430, locking is achieved by the downward force of the lock nut onto the ball 221. Friction forces created between the rotating lock nut and the ball during the final stages of tightening can cause the ball to rotate and lose its orientation. In some embodiments, the ball array guide 220 is stabilized as the lock nut is tightened.

In some embodiments, a ball locking mechanisms can use radial inward compression of the base plate socket to lock the ball of the ball array guide into the socket. In some embodiments, the inward compression of the socket does not create any motion between the parts that could misalign the ball array guide.

Figure 18:
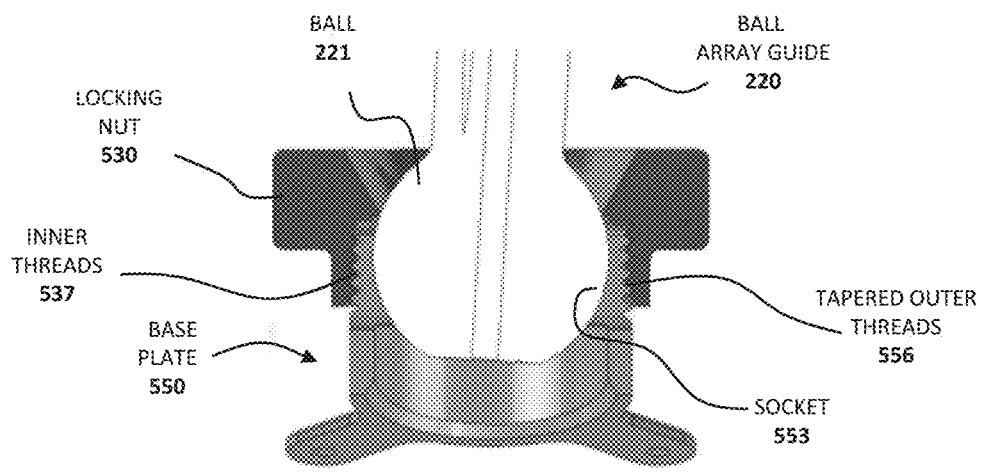
FIG. 18 is a partial cross-sectional perspective view of a ball 221 of a ball array guide 220 held in a socket 553 of a base plate 550 having tapered outer threads 556 which match inner threads 537 on locking nut 530.

FIG. 18 illustrates an arbitrary cross-sectional view of one embodiment of a ball locking mechanisms which uses radial inward compression of the base plate socket to lock the ball of the ball array guide into the socket. FIG. 18 shows a tilted base plate 550 provided with upwardly tapered outer threads 556 for coupling to the lock nut 530 which has complementary tapered inner threads 537 (i.e. the circumference of the outer threads 556 of the base plate 550 become wider from the top towards the bottom of the outer sidewall of the socket 553). This tightening and locking mechanism provides the required functional effect of compression of the socket 553 without causing significant friction with the ball 221 or creating create motion between the parts that could misalign the ball array guide. In one variation of this embodiment (not shown), the outer rim of the socket is provided with an upwardly projecting ridge and the lower rim of the circumference of the nut is partially cut away. In combination, these features ensure that the nut does not make contact with the ball.

FIGS. 19A-19D illustrate a ring clamp mechanism for providing external compression against the outer sidewall of a socket. FIGS. 19A-D show base plate 450 for cooperation with the ring clamp 80, Base plate 450 is provided with an outer groove 458 which can receive an inner circumferential ridge 81 of a ring clamp 80, as shown in FIG. 19D. A tension screw 82 (See FIGS. 19C-19D) is used to tighten or loosen the ring clamp 80. Adding more tension will compress the ring clamp 80 and produce radial inward compression on the outer sidewall of the socket 453 to lock the ball 221 in place in the socket 453. FIG. 19C illustrates an embodiment where the ring clamp 80 has complete rotational freedom around the outer groove 458 of base plate 450 when the tension screw 82 is not tight. The rotational freedom of the ring clamp 80 allows the tension screw 82 to be positioned and tightened at any rotational position necessary for the operation of the trajectory array guide system.

In some embodiments, the ring clamp has a low profile which increases the maximum deflection angles of the trajectory array from the centerline. In some embodiments, the ring clamp has a low profile which allows direct access to the screw holes without the need to extend the footprint of the base plate.

Embodiments of the present disclosure describe trajectory array guide systems which generally include a ball unit configured to fit into a socket of a base plate. In some embodiments, a trajectory array guide system can be reconfigured to include a base plate having a ball unit and an array guide having a socket configured to receive the ball unit of the base plate.

Handle

Figure 20A:
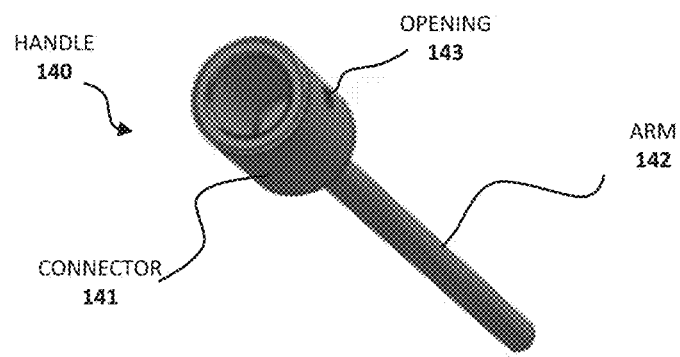
FIG. 20A is a perspective view of a handle 140.
Figure 20B:
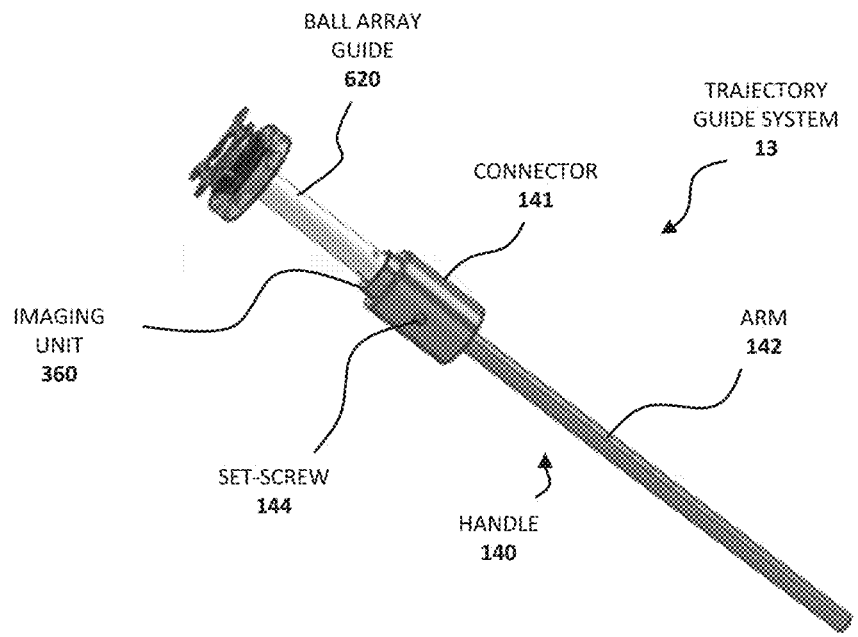
FIG. 20B is a perspective view of an embodiment of the trajectory array guide system 13 showing the handle 140 attached thereto.

In some embodiments, the orientation of the ball array guide and corresponding series of parallel trajectories is facilitated by a commercially available MRI or CT image-guided navigation system. In some embodiments, a handle can be used to connect the ball array guide with a navigation system. The handle can be engaged directly with the ball array guide. The handle can also be engaged with an imaging unit connected to the ball array guide. FIG. 20A shows one embodiment of a handle 140. FIG. 20B shows the same handle 140 attached to an imaging unit 360 of an assembled trajectory array guide system 13 which includes a longer embodiment of the ball array guide 620. In this embodiment, the connector 141 of the handle 140 is configured to be placed over the body of the imaging unit 360. A set screw 144 is placed in the side opening 143 of the connector 141 to lock the handle 140 to the imaging unit 360. The arm 142 of this embodiment of the handle 140 is roughly twice the length of the ball array guide 620. The length of the arm may vary according to the needs of the particular situation. Combinations of handles which have longer and shorter arms may be provided in kits for assembling various embodiments of a trajectory array guide system.

FIGS. 20C to 20E illustrate an embodiment of the handle 140. FIG. 20C is a side elevation view of the handle 140 and FIG. 20D is a cross-section taken along line 20D-20D of FIG. 20C. FIG. 20E is a magnified view of the connector 141 of the handle showing the opening 143 for insertion of the set screw 144 (see FIG. 20B) and an air hole 145 located near the lower end of the connector 141 in this view. The purpose of the air hole 145 is to provide a passage to allow air to escape when the connector 141 is placed over the outer sidewall of an imaging unit with a tight seal.

In some embodiments, the handle has a total length of between about 12 to about 18 cm. In some embodiments, the arm portion of the handle has a diameter of between about 6 to about 10 mm.

In some embodiments, the handle is similar to the embodiment of FIGS. 20C to 20D with the exception that the arm is hollow to allow insertion of a pointer probe which can be locked in place with a set screw through the opening in the connector.

Imaging Unit

Figure 21A:
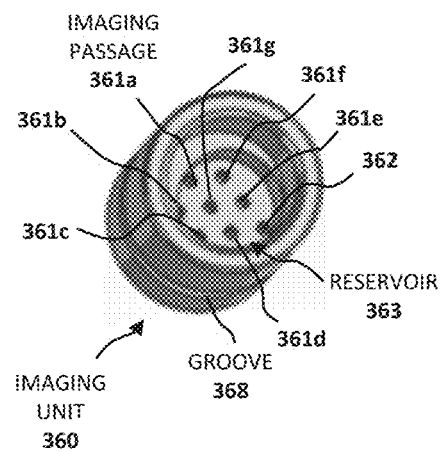
FIG. 21A is a top perspective view of an embodiment of an imaging unit 360.
Figure 21B:
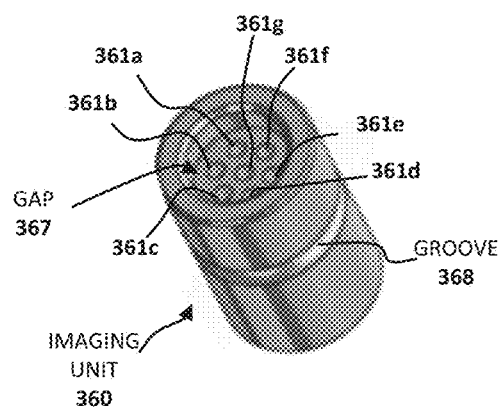
FIG. 21B is a bottom perspective view of the imaging unit 360 of FIG. 21A.

An imaging unit can be configured for connection to or engagement with a ball array guide and a handle. In some embodiments where the ball array guide uses an offset index tube (such as tube 66 of FIG. 5A for example), the imaging unit can have an index tube arranged co-axially with the outer index groove of the ball array guide (see for example, FIG. 22), Shown in FIGS. 21A and 21B are two perspective views of an embodiment of an imaging unit 360. In FIGS. 21A-21F, the imaging unit is shown without tubes being connected. The imaging unit 360 can be connected to eight tubes to provide axes for imaging trajectories and indexing.

Figure 21C:
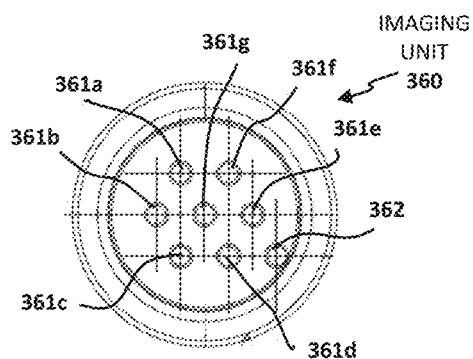
FIG. 21C is a top view of the imaging unit 360 of FIG. 21A and FIG. 21B.
Figure 21D:
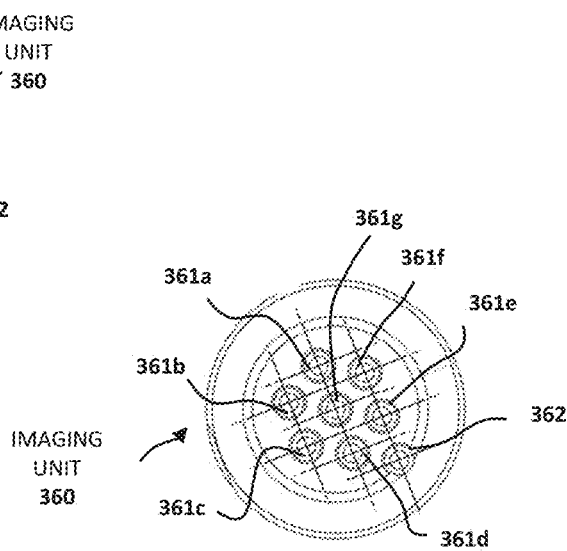
FIG. 21D is a bottom view of the imaging unit 360 of FIGS. 21A-21C.
Figure 21E:
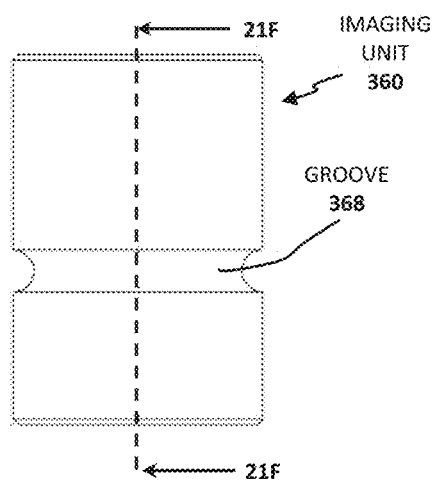
FIG. 21E is a side elevation view of the imaging unit 360 of FIGS. 21A-D.
Figure 21F:
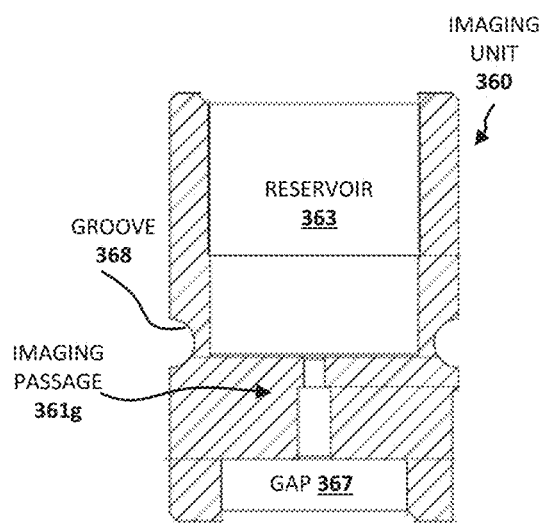
FIG. 21F is a cross-sectional view of the imaging unit 360 taken along line 21F-21F of FIG. 21E.

FIG. 21A is a top perspective view and FIG. 21B is a bottom perspective view of the imaging unit 360. FIG. 21C is a top view and FIG. 21D is a bottom view, FIG. 21E is a side elevation view and FIG. 21F is a cross sectional view taken along line 21F-21F of FIG. 21E. This imaging unit 360 is constructed to fit over the top end of a ball array guide. In the top perspective view of FIG. 21A, the top openings of all eight of the passages 361a-g and 362 (an indexing passage) are visible, as well as the reservoir 363 and a groove 368 formed in the outer sidewall of the imaging unit 360. This groove 368 is provided to receive a locking set-screw 144 extending through the connector 141 of the handle 140. FIG. 21B is a bottom perspective view of the same embodiment of the imaging unit 360, In this perspective view, the index passage 362 is not visible. For further clarity, top and bottom views of the same embodiment of the imaging guide 360 are shown in FIGS. 21C and 21D, respectively. Each of these views includes alignment lines to indicate the spatial relationships among the passages 361a-g and 362. Passages 361a-f are equi-spaced and arranged in a symmetrical hexagonal shape with passage 361g in the center and index passage 262 aligned with the line formed between passages 361c and 361d as well as the line formed between passages 361e and 361f. It is clearly seen in the cross-sectional view of FIG. 21F that the imaging unit 360 has an upper reservoir 363 for holding a volume of imaging reagent and a lower gap 367 below the intermediate solid section within which the passages 361a-g and 362 are formed. This cross-sectional view has only one passage 361g (the central passage) visible. It is seen that the upper part of passage 361g has a smaller diameter than its lower part. This arrangement is also clearly seen in a comparison of the top view of FIG. 21C with the bottom view of FIG. 21D. The larger bottom diameter is for the purpose of insertion of separate trajectory imaging tubes (not shown). During assembly of a complete imaging unit 360, the tubes are inserted and bonded into the passages 361a-g and 362 via the bottom of the imaging unit. The upper reduced diameter of each passage acts as a stop to prevent passage of the tubes into the reservoir 363.

Figure 22:
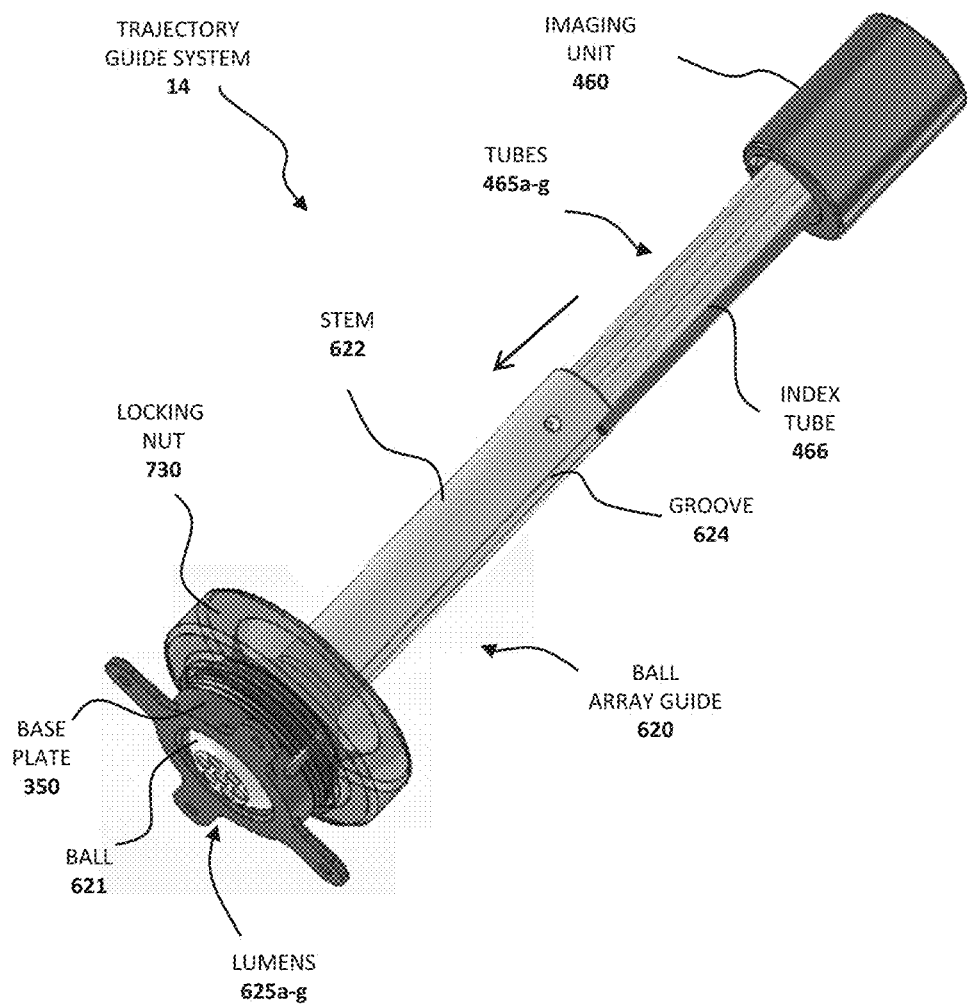
FIG. 22 is a perspective view of an embodiment of a trajectory array guide system 14, showing the manner of insertion of tubes 465a-g and 466 into the ball array guide 620.

FIG. 22 illustrates an embodiment of a trajectory array guide system 14. An embodiment of an imaging unit 460 is inserted into a longer embodiment of a ball array guide 620 (shown in more detail in FIGS. 15A, 15B, 20B and 23A-D). The imaging tubes 465a-g and 466 being arranged co-axially with the lumens 625a-g (seen at the bottom of the ball 621 of the ball array guide 620) and outer groove 624 formed in the outer sidewall of the stem 622 of the ball array guide 620. The tubes 465a-g and 466 of the imaging unit 460 will thus enter the corresponding lumens 625a-g and outer groove 624 of the ball array guide 620. The trajectory array guide system 14 includes locking nut 730 and base plate 350.

In some embodiments, the process of using the imaging unit 360 to produce images for calculation of trajectories to an identified target in the brain will include insertion of tubes 465a-g and 466 into each of the passages 361a-g and 362 of the imaging unit 360, followed by attachment of the imaging unit 360 to the upper end of the ball array guide 620 with the tubes 465a-g and 466 extending into the corresponding lumens 625a-g and outer groove 624.

Ball Array Guide and Lumens

In some embodiments, the ball array guide provides for the placement and accuracy of a catheter. The catheter is passed through a selected lumen of the ball array guide to reach a target. To allow for smooth insertion, the array guide can provide sufficient clearance between the outer diameter of the catheter and the inner diameter of each lumen of the trajectory array. The accuracy of catheter placement can be increased by increasing the length of the lumens. In some embodiments, a ball array guide and corresponding lumens have a length between about 30 mm to about 60 mm, between about 40 mm to about 50 mm, or a length of about 45 mm. In some embodiments, a ball array guide includes two parts each having a defined length that are bonded together. Such a combination of parts could be machined, 3D-printed parts, or molded parts.

Figure 23A:
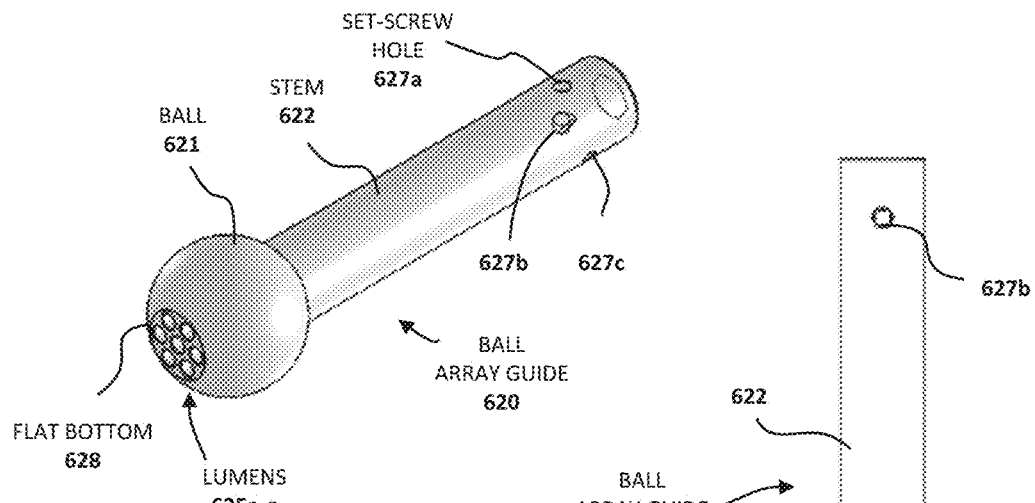
FIG. 23A is a perspective view of ball array guide 620.

FIGS. 23A-D illustrates an embodiment of a ball array guide 620. FIG. 23A is a perspective view of the ball array guide 620 where the ball 621, stem 622 and lower openings of lumens 625a-g are visible. The outer groove 624 for placement of the index tube is not visible but is to be understood to be present in this embodiment of the ball array guide 620.

Figure 23B:
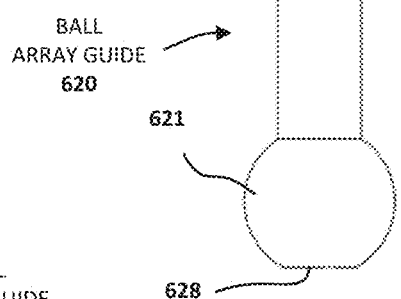
FIG. 23B is a side elevation view of ball array guide 620.
Figure 23C:
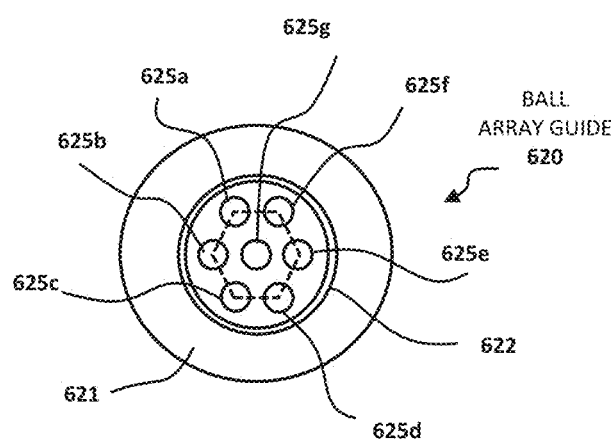
FIG. 23C is atop view of ball array guide 620.
Figure 23D:
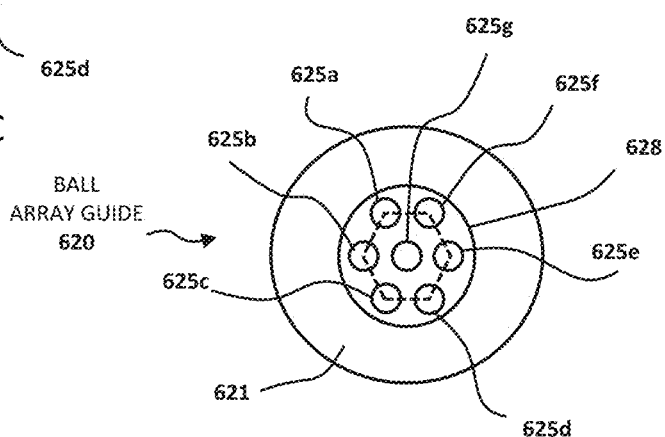
FIG. 23D is a bottom view of ball array guide 620.

The openings of the lumens 625a-g are at a flat bottom part 628 of the ball. Near the top of the stem are three set-screw holes 627a-c for insertion of set screws (not shown) to fix tubes of an imaging unit (not shown) engaged with the ball array guide. FIG. 23B is a side elevation view of the ball array guide 620. FIG. 23C is a top view of the ball array guide 620 and FIG. 23F is a bottom view of the ball array guide 620. The dashed lines in FIGS. 23C and 23D indicate that the lumens 625a-f are arranged symmetrically in a hexagonal shape and lumen 625g is in the center of this hexagonal shape.

Embodiments of a Trajectory Array Guide System

Figure 24:
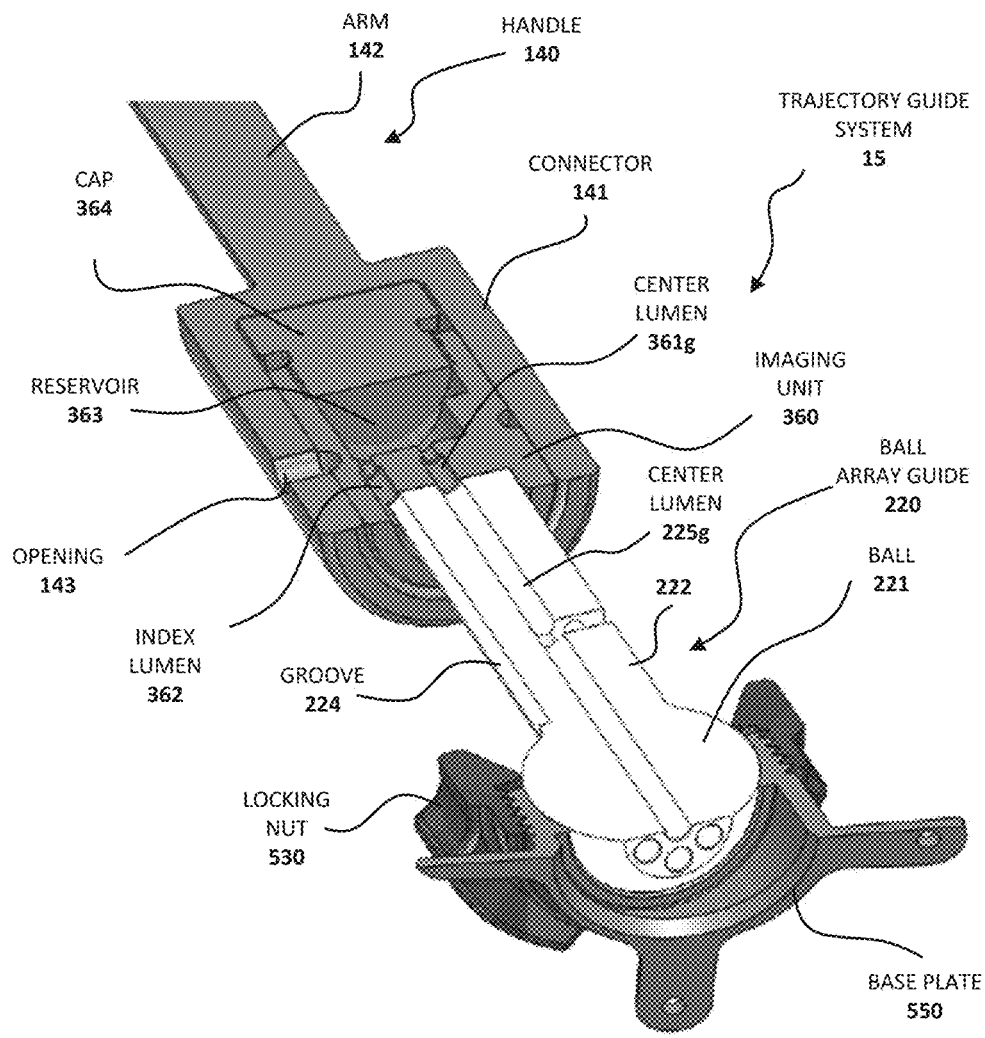
FIG. 24 is a cross-sectional perspective view of a portion of an embodiment of the trajectory array guide system 15.

The president disclosure illustrates how compatible components can be assembled in different combinations to produce various embodiments of a trajectory array guide system. FIG. 24 illustrates a cross-sectional perspective view of one embodiment of a trajectory array guide system 15, The system includes a ball array guide 220 which has a short stem 222 and a ball 221 which is compatible with the socket of the tilted base plate 550. The tilted base plate 550 has tapered threads configured to thread to locking nut 530.

Imaging unit 360 is attached to the top of the stem 222, The center passage 361g and the index passage 362 of the imaging unit 360 are aligned with the center lumen 225g and the outer groove 224 of the ball array guide 220 (the tubes are omitted in an effort to preserve clarity). The cap 364 of the imaging unit 360 is engaged with the top of the imaging unit to isolate the reservoir 363. Handle 140 is engaged with the outer circumference of the imaging unit 360 and a set screw (not shown) can be used to lock the connector 141 of the handle 140 via the opening 143 in the sidewall of the connector 141. Arm 142 extends outward from the connector 141, FIG. 25 is an exploded perspective view of an embodiment of a trajectory array guide system 16 which includes a reducer component 75 which can reduce the diameter of one of the lumens 225a-g of the ball array guide 220. This may be necessary if a smaller gauge catheter is used, as the reducer can reduce significant deviations of the catheter from its desired trajectory. The reducer 75 includes a reducer tube 76 with a diameter smaller than the diameter of the lumens 225a-g. The reducer tube 76 is engaged with a reducer disc 77 which includes a set-screw 78. The set screw 78 allows the depth of an inserted instrument to be locked in place within the reducer tube. The reducer tube 76 can be locked in place using one of the ball array guide set screws 123a-c.

Embodiments of a Trajectory Array Guide System with Separate Imaging Units and Guide Units In some embodiments, a trajectory array guide system can include an array guide in the form of a wide bore sleeve (instead of a series of lumens). This wide-bore array guide includes a ball joint for connection to a base plate. The bore of the array guide is configured to receive an imaging unit and a matched array catheter guide unit (i.e. the arrangement of imaging unit passages and catheter guide unit lumens are matched such that trajectory images generated by the imaging unit will be co-axial with the lumens in order to ensure that the pathway followed by the catheter matches the selected trajectory). This embodiment of a trajectory array guide system provides a capability to provide independent diameter sizing of the lumens used for imaging (i.e. containing imaging reagent) and the lumens used for guiding the catheter. This embodiment also provides for height alignment of the top of the catheter guide lumens with the bottom of the top imaging chamber. This embodiment can provide more reliable general alignment of components while being less delicate than embodiments using an imaging unit with imaging trajectory tubes. In general terms, the ball portion of the array guide of this embodiment is expected be larger than the ball portion of other embodiments described herein. The use of a ring-clamp as a locking mechanism is particularly amenable for use with trajectory array guide systems having separate imaging array and catheter array units because it allows greater angles of tilting of the array guide.

Figure 26D:
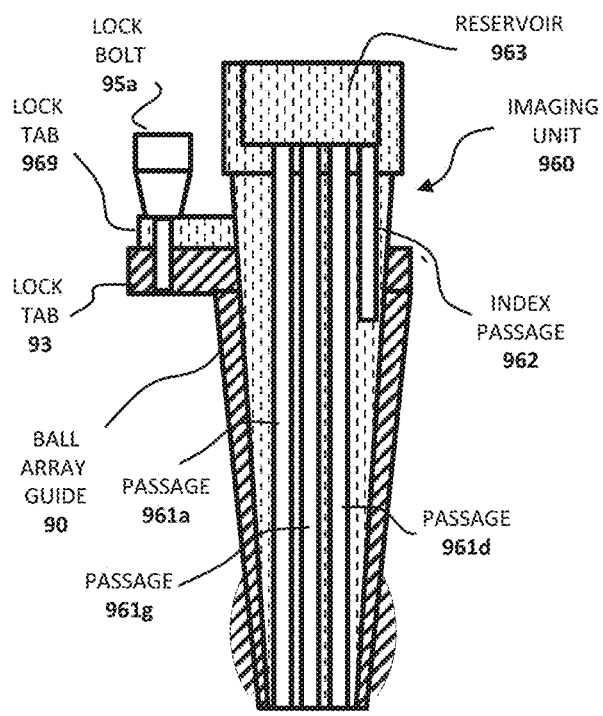
FIG. 26D is a cross-sectional view of embodiment of the ball array guide 90 of FIGS. 26A and 26B with an imaging unit 960 attached to the ball array guide 90. This cross-sectional view is taken along line 26D-26D of FIG. 26E.
Figure 26E:
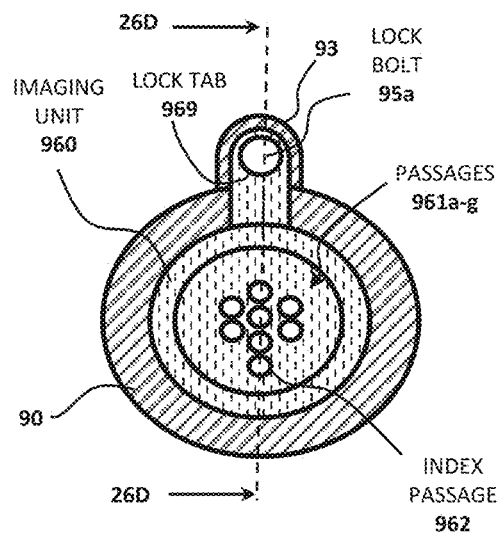
FIG. 26E is a top view of the ball array guide 90 of FIG. 26D with imaging unit 960 attached to the ball array guide 90.

One embodiment of a trajectory array guide system is shown in FIGS. 26A to 26H. FIG. 26A illustrates a cross-section (taken along line 26A-26A of the top view of FIG. 26B) of a funnel-shaped ball array guide 90 with a ball 91 at the bottom and a tapered internal bore 92 configured to receive matched imaging and catheter guide units. The top of the array guide 90 has a lock tab 93 with a bolt hole 94 for locking a corresponding imaging unit or catheter guide unit to the array guide 90. These features are also illustrated in FIG. 26B which illustrates a top view of the array guide 90.

FIG. 26C shows an arrangement for the connection of a handle 240 to the array guide 90 using a handle adapter 249 which is adaptable for engagement with different surgical navigation systems.

FIG. 26D is a cross-sectional view of one embodiment of an imaging unit 960 inserted into the array guide 90. This cross-sectional view is taken at line 26D-26D of FIG. 26E. The imaging unit 960 has a lock tab 969 which is aligned with lock tab 93 of the array guide 90 for locking the imaging unit 960 in place with a lock bolt 95a. The imaging unit 960 has a reservoir 963 for holding imaging fluid and a series of passages 961a-g and a shorter index passage 962 for imaging a series of trajectories.

FIG. 26F shows a similar arrangement (representing a cross-sectional view taken along line 26F-26F of the top view of FIG. 26G) with a catheter guide unit 920 inserted into the array guide 90. The catheter guide unit 920 has a series of lumens 925a-g and a shorter index lumen 924. Any one of lumens 925a-g may be selected based on a trajectory identified using the imaging unit 960. Passages 961a-g of the imaging unit are matched and aligned with corresponding lumens 925a-g of the catheter guide unit 920. For example, if trajectory images provided by the imaging unit 960 indicate that lumen 961c represents the optimal trajectory to the target, this will be noted and after the imaging unit 960 is removed and the catheter guide unit is inserted, lumen 921c will be the lumen used to guide the catheter to the target. The catheter guide unit 920 also has a lock tab 929 to lock the catheter guide unit 920 in place within the array guide 90. The catheter guide unit 920 also includes a locking slider 926 with openings 928a-g for locking a catheter in place within one of the selected lumens 925a-g. This locking slider 926 is shown by itself in a top view in FIG. 26H.

An example describing the operation of a trajectory array guide system is presented with reference to components illustrated in FIGS. 26A-26H.

The system is assembled with the array guide 90 connected to a base plate, such as base plate 450 for example, and with the imaging unit 960 inserted and locked into the bore 92 of the array guide 90 using the lock bolt 95a. The imaging reagent contained within the passages 961a-g and 962 is used to visualize the series of trajectories towards the target and the optimal trajectory is selected. With the array guide 90 locked in place in the base plate 450, the imaging unit 960 is removed and the catheter guide unit 920 is inserted into the bore 92 of the array guide 90 and locked in place using the lock bolt 95a. The locking slider 926 is placed in the catheter guide unit 920 and held in place using lock bolt 95b to retain the catheter in place in the selected lumen which represents the selected optimal trajectory.

Figure 27A:
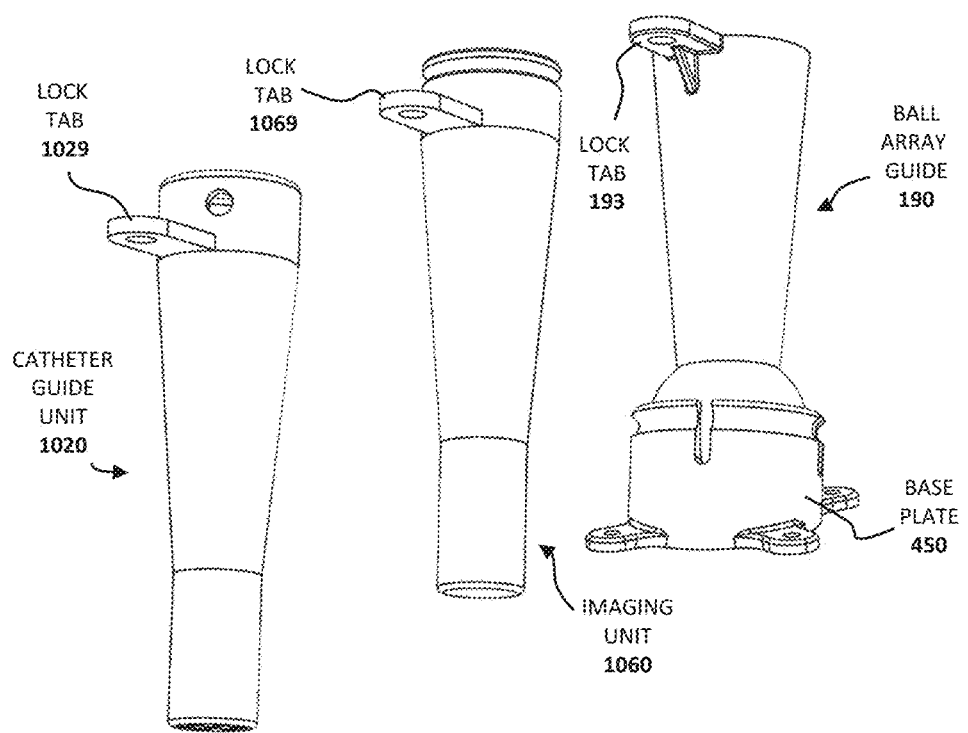
FIG. 27A includes perspective views of embodiments of a catheter guide unit 1020, an imaging unit 1060 and a ball array guide 190 placed in a base plate 450.
Figure 27B:
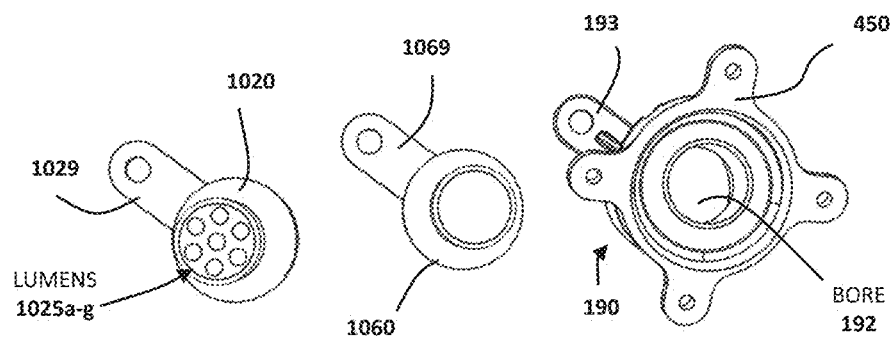
FIG. 27B includes bottom perspective views of the same embodiments of the catheter guide unit 1020, imaging unit 1060, ball array guide 190 and base plate 450 of FIG. 27A.
Figure 27C:
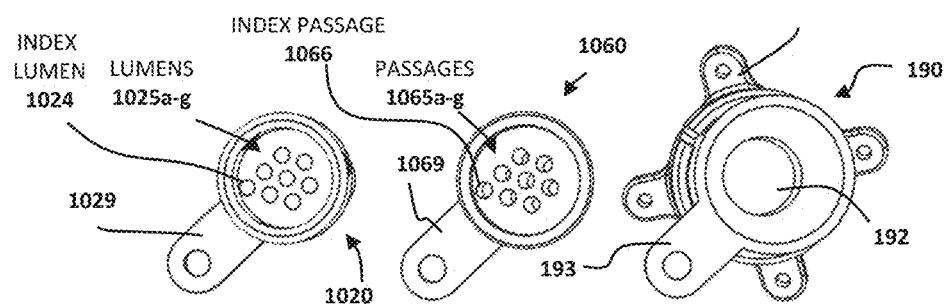
FIG. 27C includes top perspective views of the same embodiments of the catheter guide unit 1020, imaging unit 1060, ball array guide 190 and base plate 450 of FIGS. 27A and 27B.

FIGS. 27A-27C illustrate a generally funnel-shaped ball array guide 190 which is provided with a wide bore 192 to receive both a funnel-shaped imaging unit 1060 and a matched catheter guide unit 1020. The ball array guide 190 is shown connected to the socket of base plate 450. The ball array guide has a lock tab 193 for locking to a corresponding lock tab 1069 of the imaging unit 1060 and for locking to a corresponding lock tab 1029 of the catheter guide unit 1020. The lumens 1025a-g and index lumen 1024 as well as the passages 1065a-g and index passage 1066 are visible in FIG. 27C.

Trajectory array guide systems which include a funnel-shaped array guide and corresponding funnel-shaped units can have advantages over other embodiments of the trajectory array guide system. For example, the array of tubes of imaging units can be difficult to insert into corresponding lumens of a ball array guide. There is also a manufacturing challenge in sealing tubes to an imaging unit. There can also a degree of movement between the ball array guide and the tubes which cause a degree of flexure of the system when a handle is connected. In addition, a reducer (see for example reducer 70 in FIG. 25) is required to handle catheters with reduced diameters, whereas the construction of a funnel-shaped catheter guide unit of the present disclosure can be modified to provide units with different sized lumens. Notably, 14-gauge and 16-gauge catheters can require different correction factors for insertion depth. This is particularly important because lower gauge (reduced diameter) imaging unit lumens may provide the best images. The embodiment described in this section addresses these disadvantages, among others.

Figure 28:
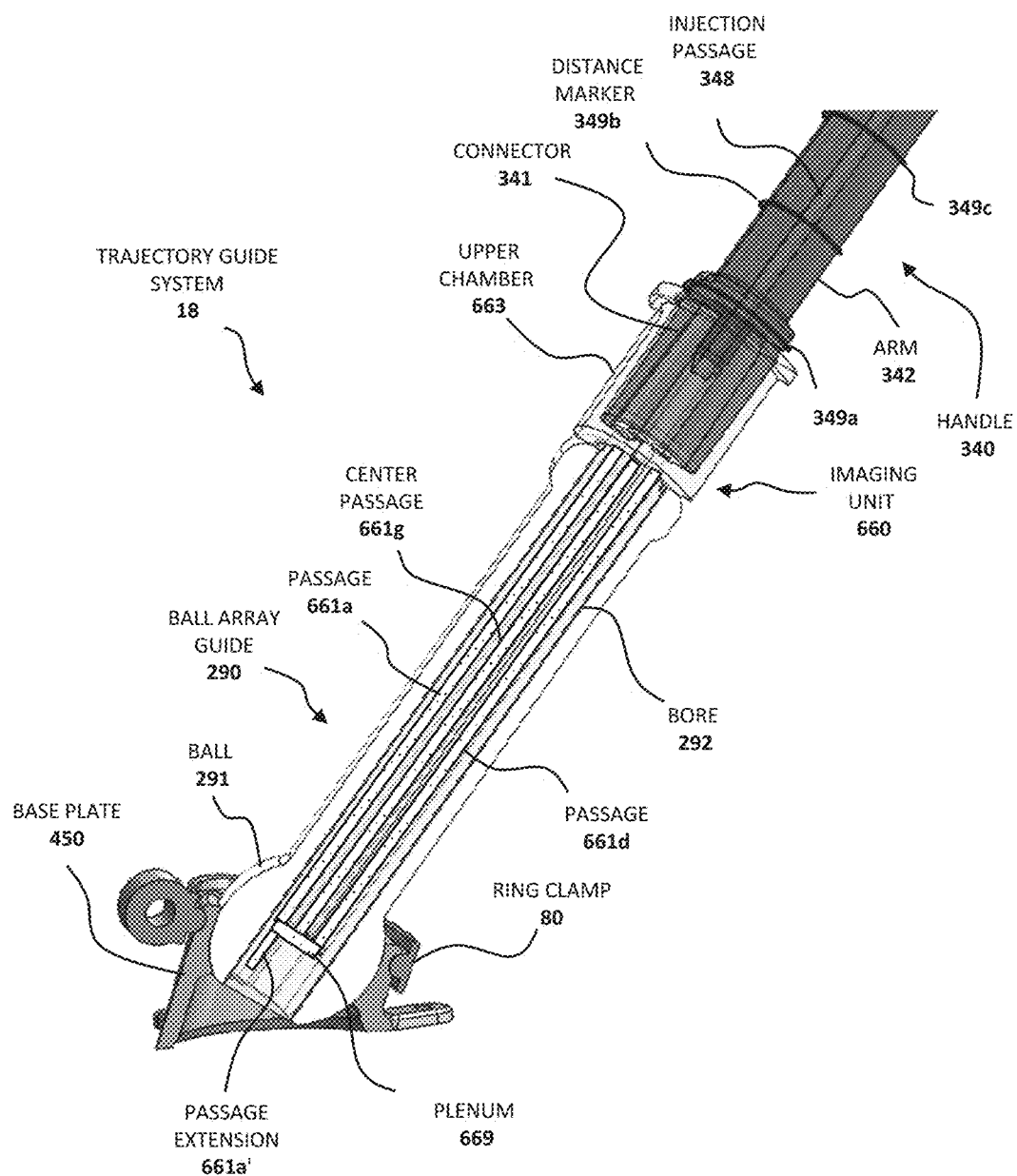
FIG. 28 is an arbitrary cross-sectional view of an embodiment of a trajectory array guide system 18 including an imaging unit 660 and a handle 340.

Trajectory Array Guide System with Alternative Imaging Fluid Injection Path and Handle Connection FIG. 28 is an arbitrary cross-sectional perspective illustration of one embodiment of a trajectory array guide system 18 which uses separate imaging and catheter guide units in a manner similar to the system described in FIG. 26A to FIG. 27C.

This trajectory array guide system 18 includes base plate 450 with its tilted socket and a ring clamp 80. This base locking combination is used to retain an embodiment of a ball array guide 290 which like the ball array guide 90 of FIG. 26 has a ball 291 configured to be held in the socket of the base plate 450 and a bore 292 for holding imaging and catheter guide units. In FIG. 28, an imaging unit 660 is shown inserted into the bore 292 of the ball array guide 290. This imaging unit 660 has a series of seven passages 661a-g with only passages 661a, 661d and 661g being visible in this perspective view. Lumens 661b-g terminate at an orthogonal passage-connecting plenum 669 which is located at the center of rotation of the ball 191. Passage 661a is extended a short distance downward from the plenum 669 and forms a passage extension 661a'.

In this embodiment, the handle 340 is provided with an injection passage 348 along the axis of the arm 342 through to the connector 341 which fits into a cavity in the upper chamber 663 of the imaging unit 660. The injection passage 348 in the arm 342 of the handle 340 is for injection of imaging fluid via a port (not shown) in the arm 342. The port may be located at any position along the arm 342 of the handle 340 as long as imaging fluid may be effectively injected into the injection passage 348. When continuously injected, the imaging fluid moves down the injection passage 348 and enters the center passage 661g. When the injected imaging fluid reaches the plenum 669, the imaging fluid then disperses in the plenum 669 and fills the remaining passages 661a-f from the bottom upwards. The imaging fluid also fills the lower extension 661a' of passage 661a. In this manner, all passages 661a-g are appropriately filled with imaging fluid for identification of the array of parallel trajectories. The lower passage extension 661a' is easily identified and distinguished from the remaining passages under magnetic resonance imaging and serves as an index image for identification of the trajectory images (this would otherwise be impossible due to the symmetrical hexagonal arrangement of the passages 661a-g). This arrangement obviates the need for an eighth passage used as an index passage as in the previous embodiments.

Figure 31:
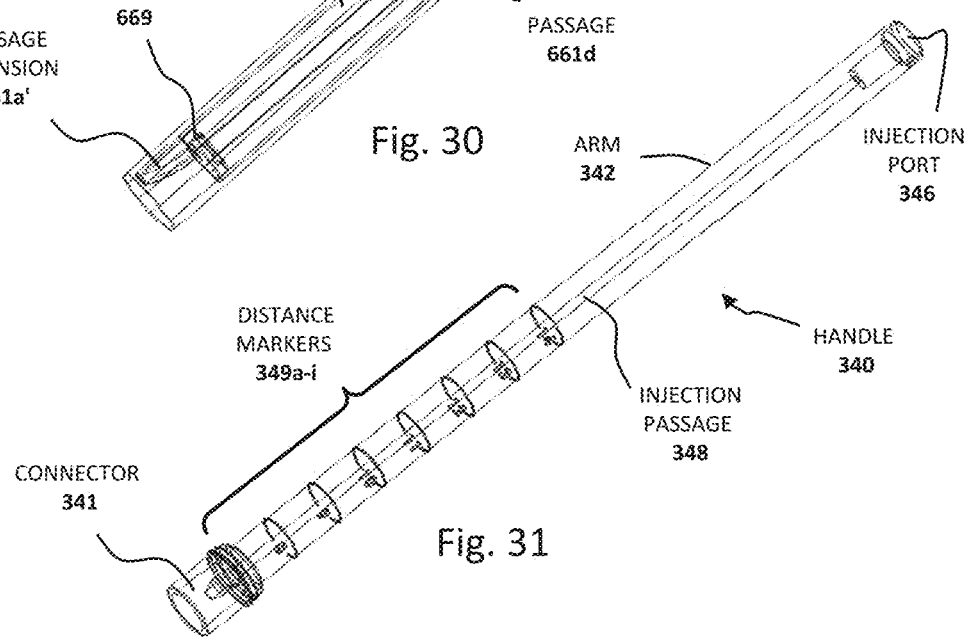
FIG. 31 is a transparent perspective view of the handle 340 showing the internal injection passage 348 and injection port 346.

As a result of this arrangement of features, all passages 661a-g and 661a' can be filled with imaging fluid via a port (such as a Luer taper injection port) in the handle 340 which is conveniently accessible (see for example, FIG. 31). An air hole (not shown) is provided in communication with the flow path of injected fluid in order to allow air displaced by the imaging fluid to vent from the flow path. This arrangement also allows the flow path to be purged with fluid or air for cleaning.

In some embodiments, the connector 341 of the handle 340 slides into the upper chamber 663 of the imaging unit. This provides an improved sealing arrangement and eliminates the need for a cap for the imaging unit 660. An alternative of this embodiment is an arrangement where the handle 340 is bonded or integrally formed with the upper chamber of the imaging unit 660 during manufacture. This could allow the entire assembly of the imaging unit 660 with the monolithically formed handle 340 to be discarded with the imaging fluid contained therein.

The handle is provided with distance markers (markers 349a-c are shown in this partial view and more would be visible in a complete illustration of the handle 340) which indicate the distance from the center of rotation of the ball 291. This feature provides a means of identifying sideways movement of the handle 340 at a given distance from the center of rotation of the ball 291, which creates a known opposite movement of a trajectory of the same length as that distance.

Figure 29:
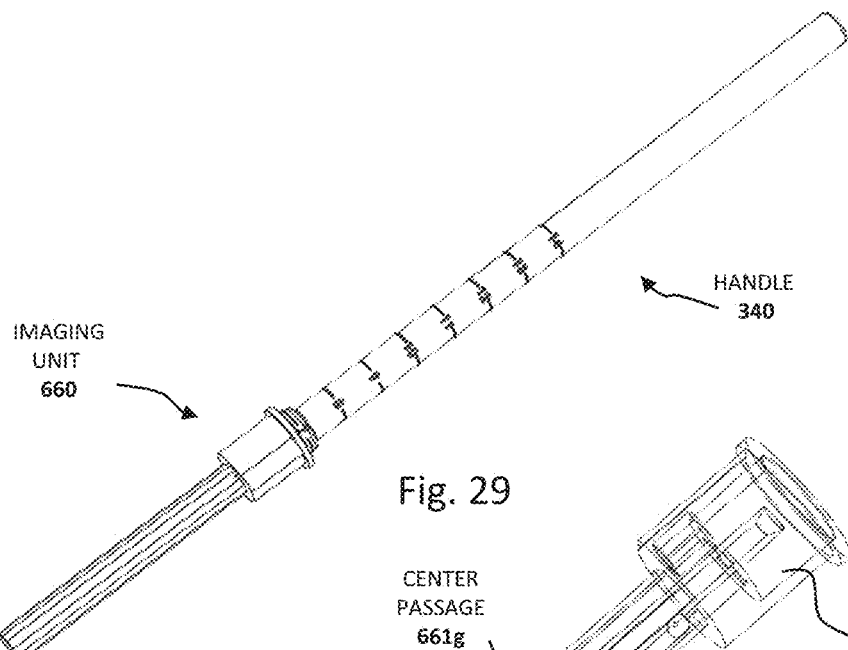
FIG. 29 is a perspective view of a partial assembly including imaging unit 660 and attached handle 340.
Figure 30:
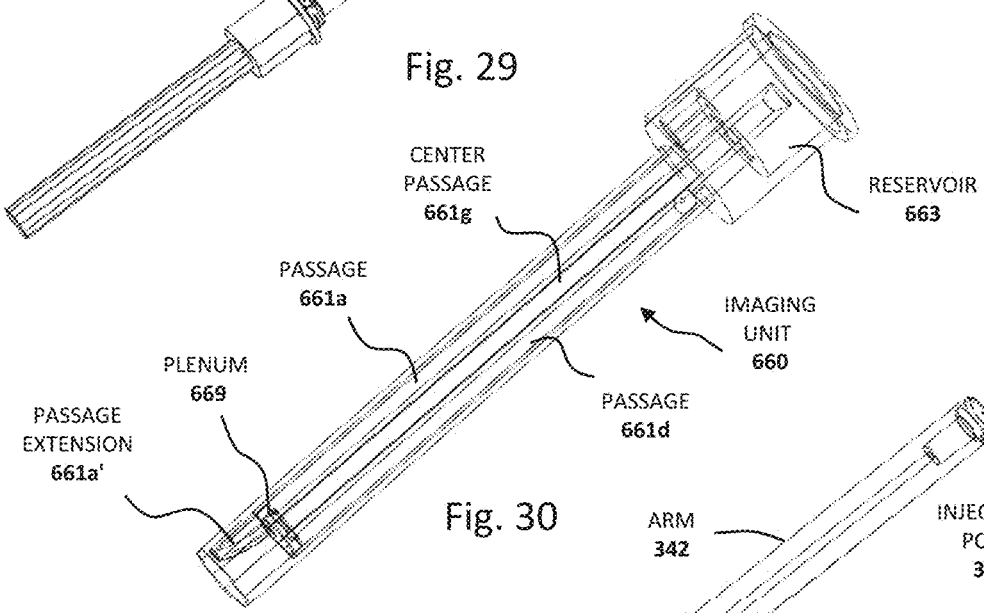
FIG. 30 is a transparent perspective view of imaging unit 660 showing internal imaging passages 661a, 661d and 661g as well as plenum 669 and passage extension 661a'.

FIG. 29 is a perspective view of the sub-assembly of the imaging unit 660 and the handle 340. FIG. 30 is a transparent perspective view of the imaging unit 660 which shows internal features including imaging passages 661a, 661d and 661g (remaining passages 661b, 661c, 661e and 661f are not visible in this view), passage extension 661a' plenum 669 and reservoir 663. Likewise, FIG. 31 is a transparent perspective view of the handle 340 which shows the internal injection passage 348 and the injection port 346. In addition, distance markers 349a-i are shown as graduations at and above the connector 341. The internal injection passage 348 provides a convenient means for filling the imaging unit 660 with imaging fluid while the handle 340 and imaging unit 660 subassembly is assembled.

FIGS. 32 and 33A-33B illustrate one embodiment of imaging unit 660 and one embodiment of the ball array guide 390. The imaging unit 660 is seen in a perspective view in FIG. 32. The imaging unit 660 has a solid bottom 660' indicating that all of the imaging passages 661a-g which begin at the bottom of the reservoir 663 terminate within the body of the imaging unit 660 (see FIG. 33B). The ball array guide 390 and the subassembly of both the ball array guide 390 and the imaging unit 660 are shown in perspective views in FIGS. 33A and 33B. The ball array guide 390 has a wide bore 392 which extends from the top through to the bottom of the ball 391. When the imaging unit 660 is fully inserted into the ball array guide 390, the solid bottom of the imaging unit 660' is seen at the bottom of the ball 391.

Figure 34:
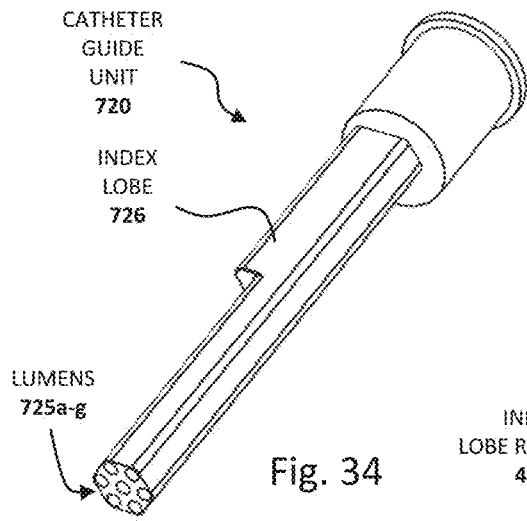
FIG. 34 is a perspective view of an embodiment of a catheter guide unit 720 which has an index lobe 766.
Figure 35A:
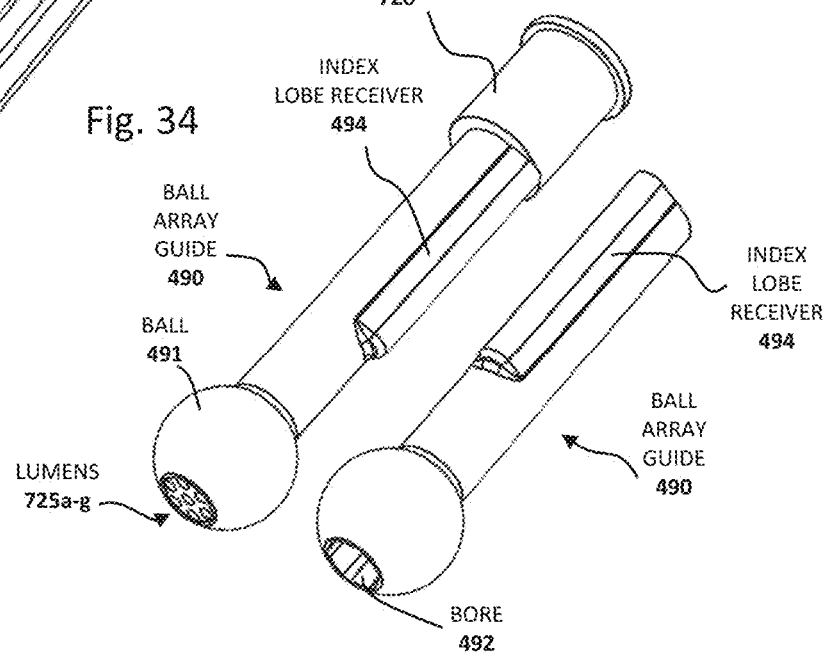
FIG. 35A includes a perspective view of an embodiment of a ball array guide 490 having a central bore 492 and an index lobe receiver 494 and a perspective view of an assembly of ball array guide 490 with catheter guide unit 720.
Figure 35B:
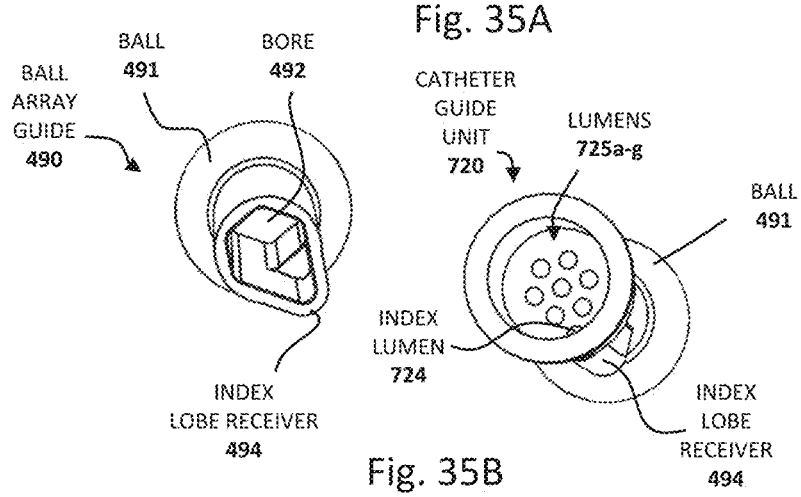
FIG. 35B includes top perspective views of ball array guide 490 and the assembly of the ball array guide 490 with catheter guide unit 720.

FIGS. 34 and 35A-35B illustrate one embodiment of a catheter guide unit 720 and one embodiment of a ball array guide 490. The catheter guide unit 720, shown by itself in a perspective view in FIG. 34, is provided with an outer index lobe 726 to accommodate the presence of a shorter index lumen 724 which is outside of the hexagonal symmetry of the main pattern of lumens 725a-g (see FIG. 35B). The index lumen 724 is used for identification of the individual lumens 725a-g during imaging. In FIGS. 34 and 35A, the lumens 725a-g extend all the way from the top to the bottom of the catheter guide unit 720. These lumens 725a-g are visible in the bore 492 at the bottom of the ball 491 of the ball array guide in FIG. 35A. The ball array guide 490 is provided with an index lobe receiver portion 494 to accommodate the entry of the index lobe 726 of the catheter guide unit 720. The presence of the lobe 726 allows the catheter guide unit 720 to be constructed with a smaller diameter lower portion to make a tighter array of lumens 725a-g. The lobe receiver 494 of the ball array guide 490 provides an improvement over the outer groove arrangement of other embodiments of the ball array guide by protecting the index passage which is used during imaging.

Trajectory Array Guide System Having Separate Imaging Unit and Guide Units with Slanted Arrays A trajectory array guide system can include a funnel-shaped ball array guide which includes matched arrays of lumens and imaging passages which are angled with respect to the longitudinal axis of the ball array guide. Such angled or slanted arrays may be designed to expand the range of possible trajectories outside of the typical straight array in which all lumens and passages are aligned with the longitudinal axis of the array guide. This can create a "footprint" three times the size of the single straight array. The advantage of this approach is that the ball-joint can remain in the locked position (i.e. adjustments of the ball-joint are not required). A single slanted imaging array could provide a wide range of additional trajectories arranged circumferentially around the central array when locked in various positions.

Figure 36A:
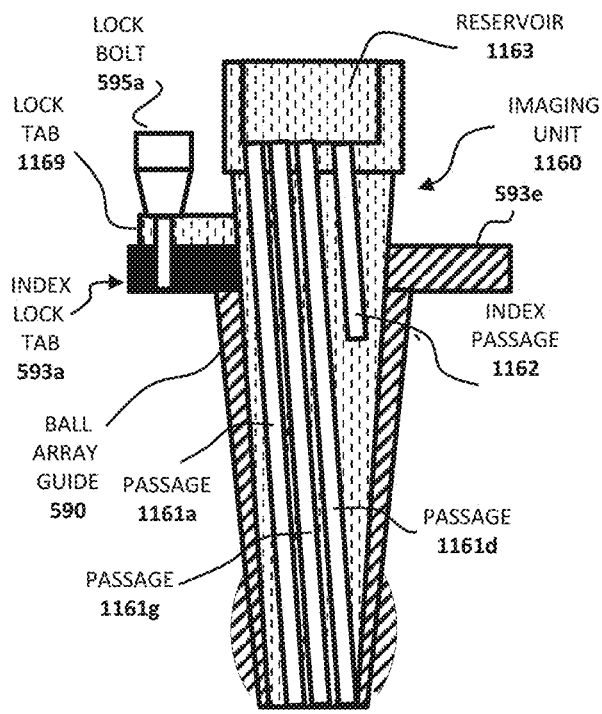
FIG. 36A is a cross-sectional view of an embodiment of a ball array guide 590 with an imaging unit 1160 attached to the ball array guide 590. This cross-sectional view is taken along line 36A-36A of FIG. 36B.
Figure 36B:
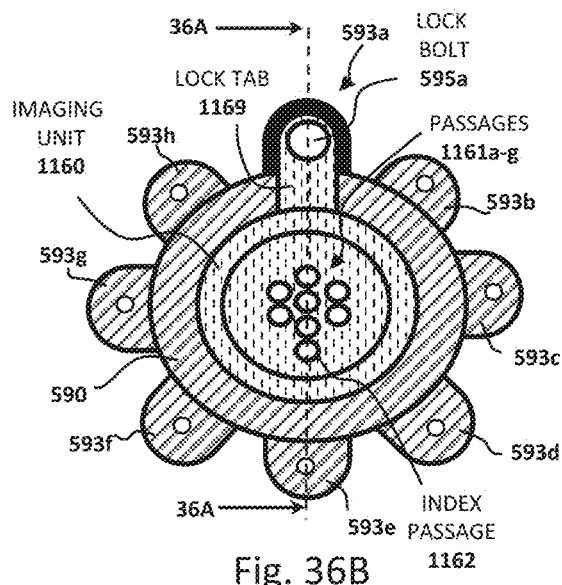
FIG. 36B is a top view of the ball array guide 590 of FIG. 36A with an imaging unit 1160 attached to the ball array guide 590.

FIG. 36A shows a cross-sectional view of a subassembly of one embodiment of a funnel-shaped ball array guide 590 with a wide bore to accommodate insertion of a funnel-shaped imaging unit 1160. FIG. 36B is a top view of the same arrangement shown in FIG. 36A. Ball array guide 590 includes eight equi-spaced lock tabs 593a-h which are each configured to lock the ball array guide 590 to the imaging unit 1160 and to lock the ball array guide 590 to the matched catheter guide unit 1120 (see FIG. 36C). The index lock tab 593a (in the 12:00 position in FIG. 36B) is provided with a differentiating indicator such as a different color (as indicated by the black fill in FIG. 36B) for identification. The imaging unit 1160 has the usual hexagonal pattern of imaging passages 1161a-g and an index passage 1162 as seen in FIG. 36B. However, each of the passages 1161a-g is angled away from the longitudinal axis of the imaging unit 1160 as indicated by representative passages 1161a, 1161d and 1161g of FIG. 36A (the remaining passages 1161b, 1161c, 1161e and 1161f are hidden from view in this cross-section). The angled passages 1161a-g and index passage 1162 are substantially parallel and extend from the bottom of the reservoir 1163 to a position close to the bottom of the imaging unit 1160.

The placement of the single lock tab 1169 of the imaging unit (with locking using lock bolt 595a) in a position other than the index position shown in FIG. 36B will have the effect of rotating the trajectory direction of the hexagonal array of passages 1161a-g. Because each of the passages 1161a-g of the hexagonal array is angled, this rotation has the effect of shifting the direction of the array of potential trajectories to create a wider circle of end points for the potential trajectories as shown in FIGS. 37A and 37B.

FIG. 36C is a cross-sectional view of the subassembly of the ball array guide 590 with a catheter guide unit 1120 inserted into the wide bore of the ball array guide 590. This catheter guide unit 1120 is matched to the imaging unit 1160 and thus has slanted lumens 1125a-g and a slanted index lumen 1124 which match the passages 1125a-g and index passage 1162 of the imaging unit 1160. Thus, when the imaging unit 1160 is used to identify, an optimal trajectory passage, the lumen corresponding to that optimal trajectory passage will be used for injection of the catheter. For example, if imaging passage 1161d was identified as representing the optimal trajectory to the target, lumen 1125d of the matched catheter guide unit 1120 would be used as the pathway to inject the catheter. The catheter guide unit 1120 has a lock tab 1129 for locking the catheter guide unit 1120 to any one of the lock tabs 593a-i of the ball array guide 590 (see FIG. 36D).

The catheter guide unit 1120 also includes a locking slider 1126 with openings 1128a-g for locking a catheter in place within one of the selected lumens 1125a-g, This locking slider 1126 is shown by itself in a top view in FIG. 36E. The locking slider 1126 is secured to the catheter guide unit 1120 using lock bolt 595b.

Figure 37A:
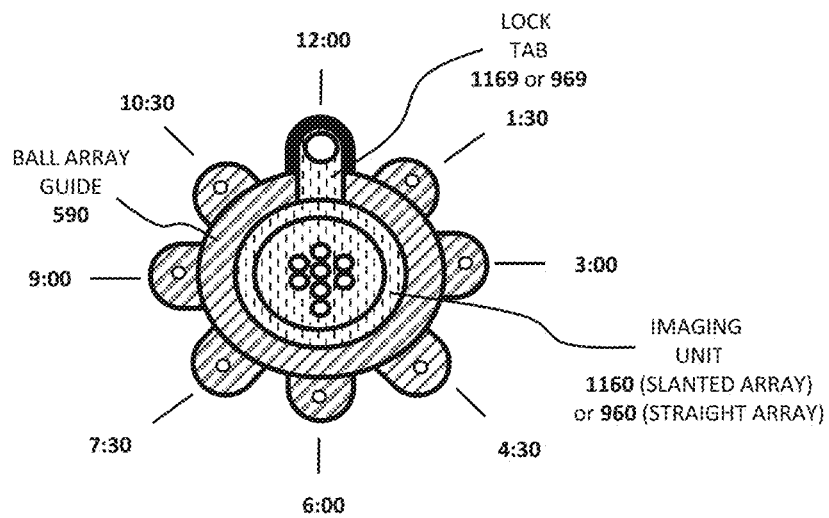
FIG. 37A is a generalized top view of ball array guide 590 with either imaging unit 960 (straight array) or 1160 (slanted array) attached thereto. This illustration includes clock position markings for the purpose of identifying array locations produced by locking the lock tab 969 or 1169 of imaging unit 960 or 1160, respectively, at each of the different clock positions.
Figure 37B:
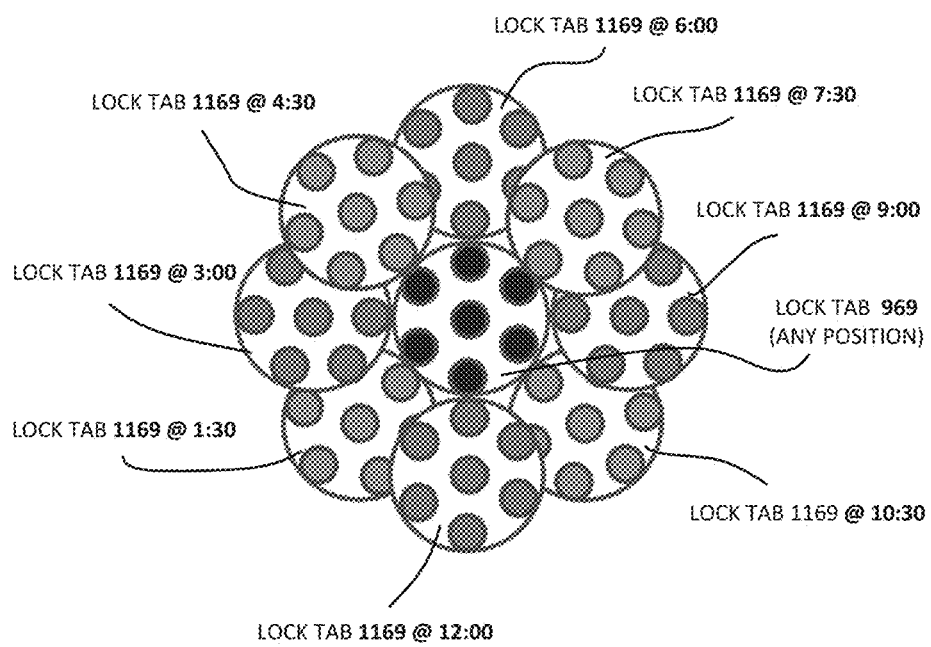
FIG. 37B is an illustration indicating the increased array footprint area provided when imaging unit 1160 is placed at the eight different clock positions. Imaging unit 960 (straight array) provides the same array regardless of its clock position connection to the ball array guide 590.

As noted hereinabove, FIGS. 37A and 37B are provided to indicate how placement of imaging unit 1160 with its lock tab 1169 locked to any one of the lock tabs 593a-i will result in direction of the array of trajectories to a different outward location, which are identified using clock positions.

In accordance with the angular direction of the passages 1161a-g and lumens 1121a-g away from the index lock tab 593a (12:00 position), it is understood that the trajectories are directed in the opposite direction (towards the 6:00 position). Therefore, according to this arrangement, it is seen in FIGS. 37A and 37B that when the lock tab 1169 of imaging unit 1160 is locked to tab 593a (12:00 position), the array will be directed towards the 6:00 position. This opposing directivity holds for the remaining positions.

The use of ball array guide 590 may be combined with imaging units and catheter guide units with straight arrays such as those illustrated in FIGS. 26A-26H. Therefore, if imaging unit 960 of FIGS. 26A and 26B is inserted into the ball array guide 560, it can be locked to any one of lock tab positions 593a-i and the trajectory direction of the array will remain centralized with no outward directivity because the array of the imaging unit 960 is straight. Therefore, a combination of imaging and guide units with straight arrays and imaging and guide units with slanted arrays can cover a wide footprint as illustrated in FIG. 37B. Importantly the wide footprint of trajectory coverage may be obtained without adjusting the ball array guide 590 within its socket in the base plate.

Figure 38A:
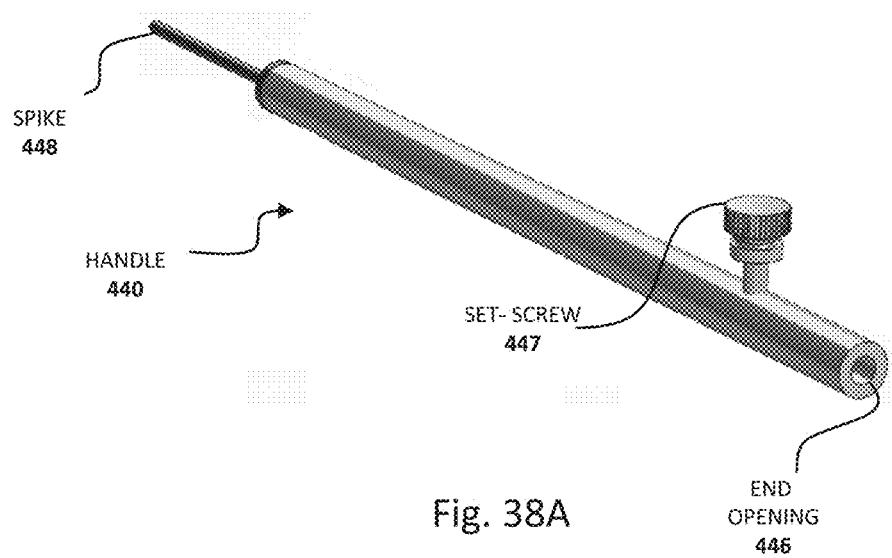
FIG. 38A is a perspective view of an embodiment of the handle 440.
Figure 38B:
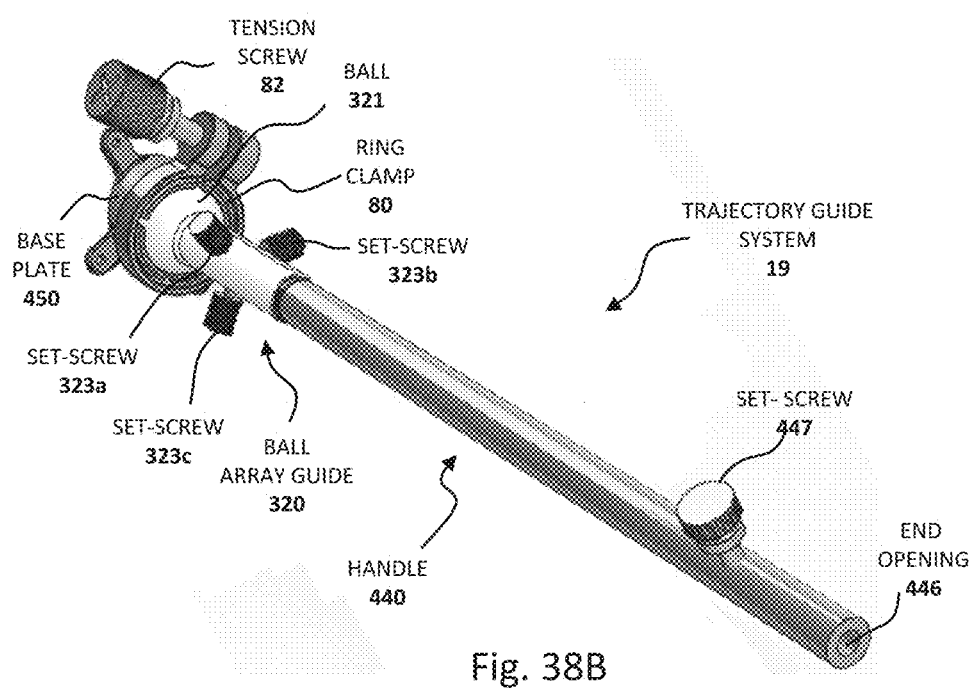
FIG. 38B is a perspective view of a trajectory array guide system 19 which includes handle 440.
Figure 38C:
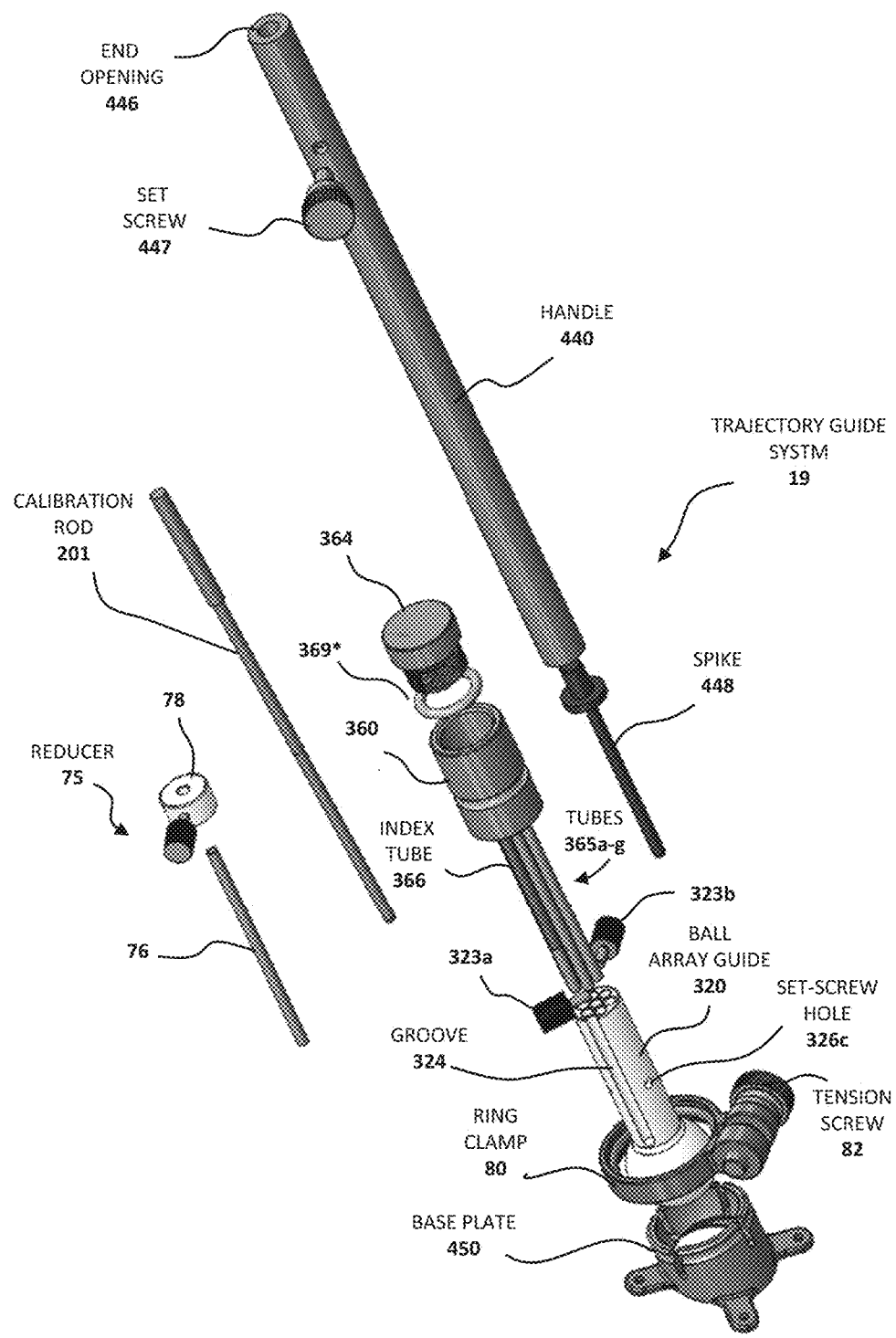
FIG. 38C is an exploded perspective view of trajectory array guide system 19.
Figure 38D:
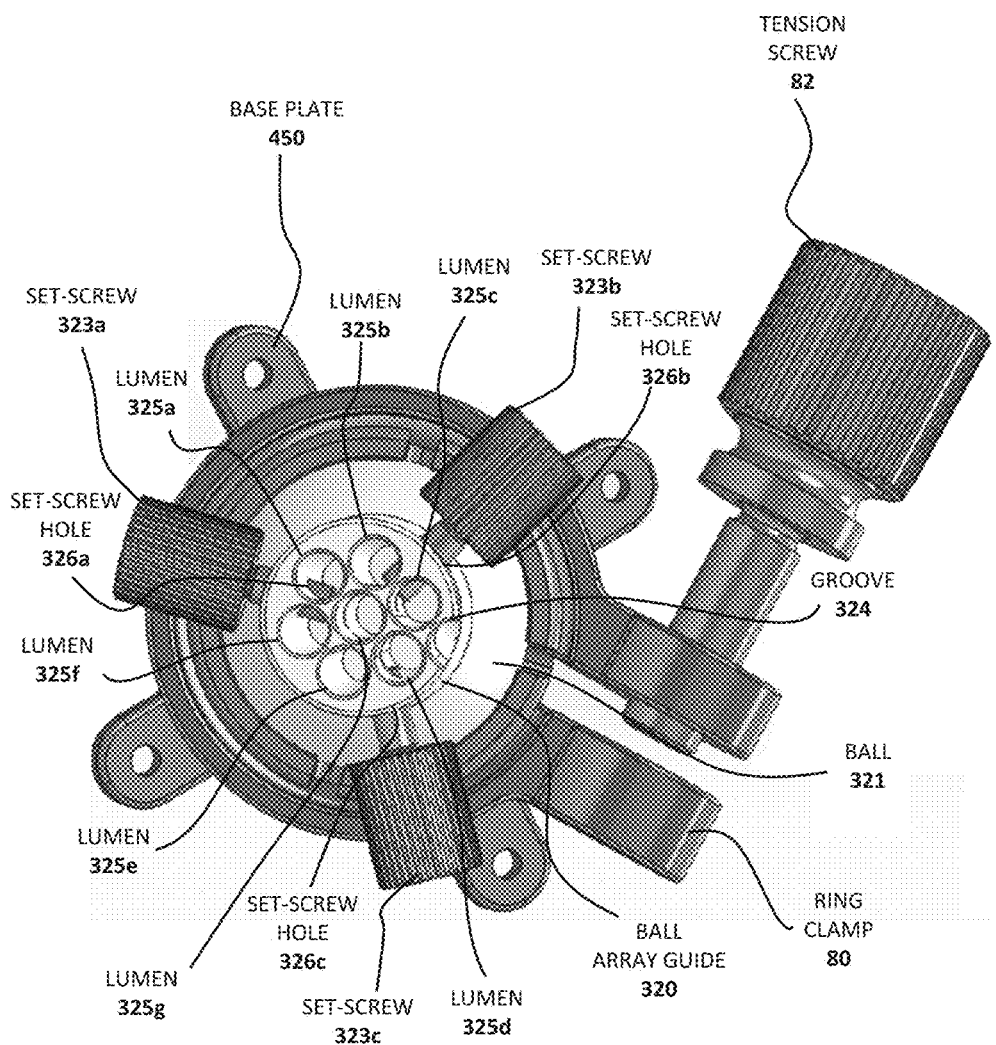
FIG. 38D is a top perspective view of the trajectory array guide system 19 without the handle 440 to indicate penetration of set-screws 323a-c into the lumens 325a-g of the ball array guide 320.

Trajectory Array Guide System with Alternative Handle for Connection to Navigation Pointer for Image-Guided Surgery An embodiment of a trajectory array guide system 19 is shown in FIGS. 38A-D. This embodiment includes a handle 440 which is constructed to facilitate connections to navigation pointers of image guided surgery systems currently in use. As such, the handle 440 (shown by itself in FIG. 38A) is designed for direct placement on and engagement with a ball array guide 320 which is seen as part of the complete system 19 in FIGS. 38B-38D. The placement is made by inserting a spike 448 into one of the selected lumens 325a-g (see FIG. 38D). The handle 440 is hollow to allow insertion of the spike 448 at one end. The hollow handle 440 also allows for the attachment a navigation pointer to the back end opening 446 of the hollow handle. A set-screw 447 penetrating into the bore of the handle 440 is provided to hold the navigation pointer in place, FIG. 38B shows one embodiment of an assembled trajectory array guide system with the handle 440 engaged with an embodiment of the ball array guide 320 which has three set screws 323a-c positioned closer to the ball 321 than to the upper end of the ball array guide 320, This arrangement is provided to allow direct connection of certain types of surgical navigation systems to the upper part of the ball array guide 320, This system 19 uses base plate 450 in combination with ring clamp 80 as seen in FIGS. 38B-D.

FIG. 38C is an exploded view showing components of a trajectory array guide system 19, including imaging unit 360, reducer 75, and a calibration rod 201. In some embodiments, the calibration rod 201 can be used to calibrate positioning of the ball array guide 320 with respect to certain image guided surgery systems which can be connected directly to the upper body of the ball array guide 320. The calibration rod 201 has an upper portion with a wider diameter than the bottom portion to provide two calibration diameters to fit different sized holes. In one embodiment of the calibration rod, the wider portion of the calibration rod 201 has an outer diameter of 2.1 mm to fit the center lumen of the ball array guide 320 and the narrower portion of the calibration rod 201 has an outer diameter of 2.0 mm to fit into a calibration hole on the calibration tool of a Brainlab StarLINK™ image guided surgery system. This calibration rod 201 can also be compatible with the Medtronic Sure-Trak™ image guided surgery system, and other image guided surgery system known to those in the art. In some embodiments, trajectory array guide system 19 includes an O-ring 369 which creates a seal between the cap 364 and the imaging unit 360.

FIG. 38D is a top view of the system without the handle 440. The ball array guide 320 has three set-screw holes 326a-c which allow each set screw 323a-c to penetrate the body of the ball array guide 320 and enter three of the seven lumens 325a-g. Therefore, set-screw 323a penetrates into lumens 325a, 325b and 325g; set-screw 323b penetrates into lumens 325c, 325d and 325g: and set-screw 323c penetrates into lumens 325e, 325f and 325g. As such, the spike 448 can be fixed in place in any one of the seven lumens 325a-g.

Figure 39:
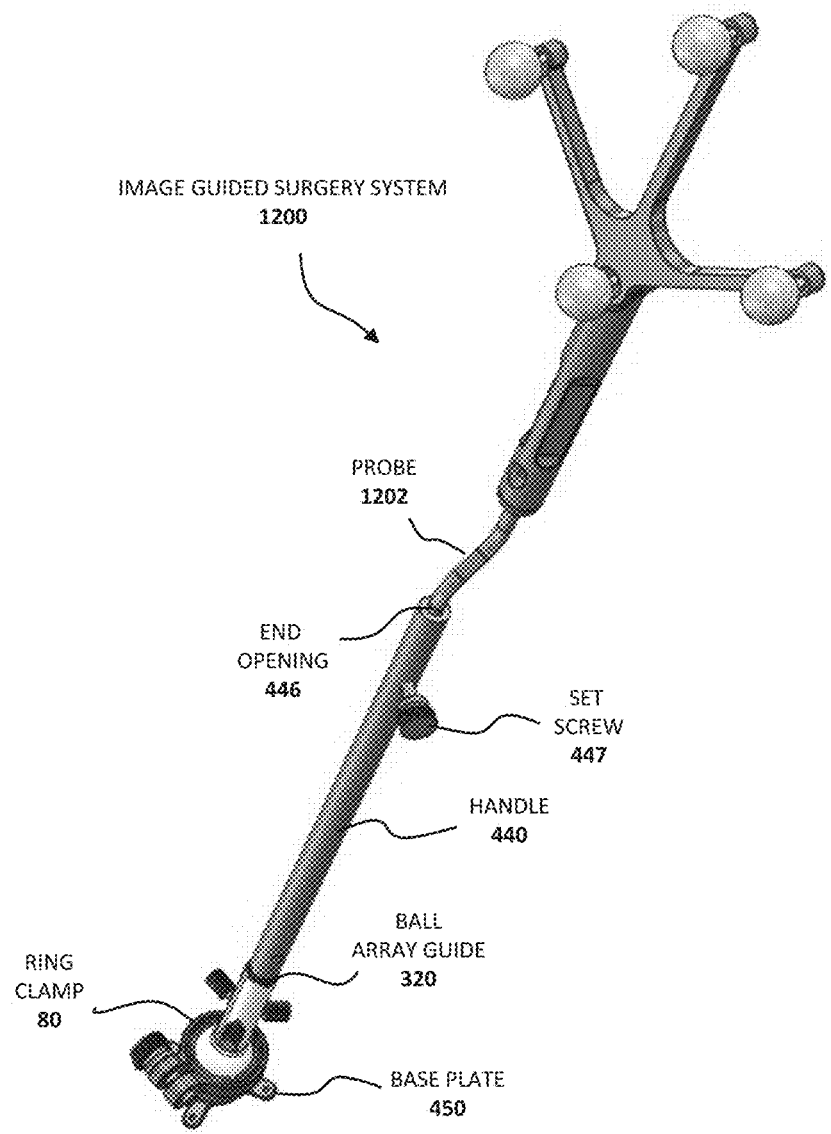
FIG. 39 is a perspective view of a trajectory array guide system engaged with an image guided surgery system 1200.
Figure 40A:
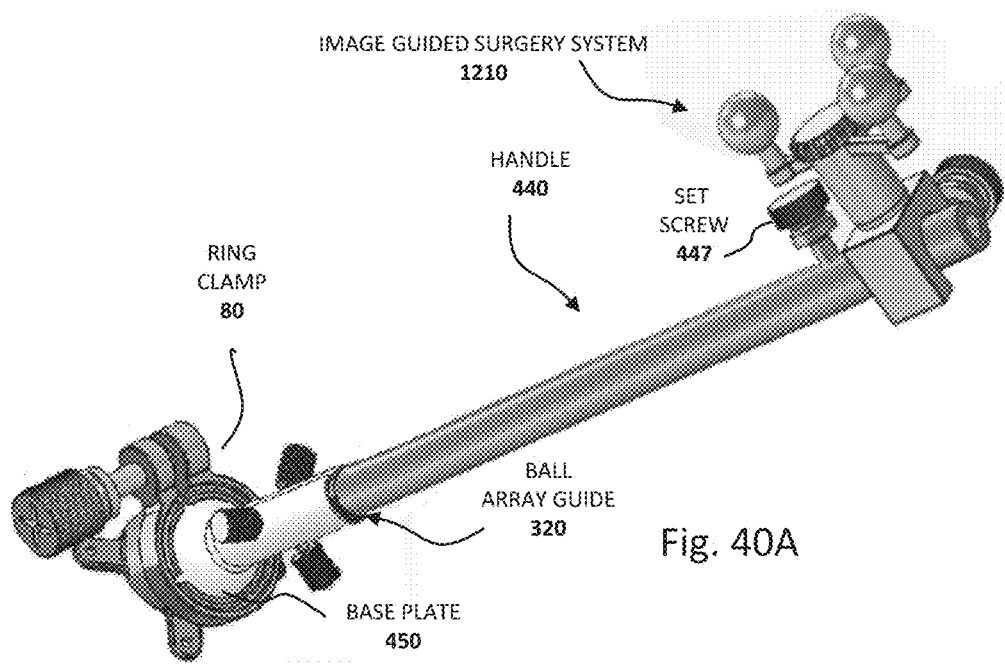
FIG. 40A is a perspective view of an image guided surgery system 1210 clamped onto a handle 440 of a trajectory array guide system.
Figure 40B:
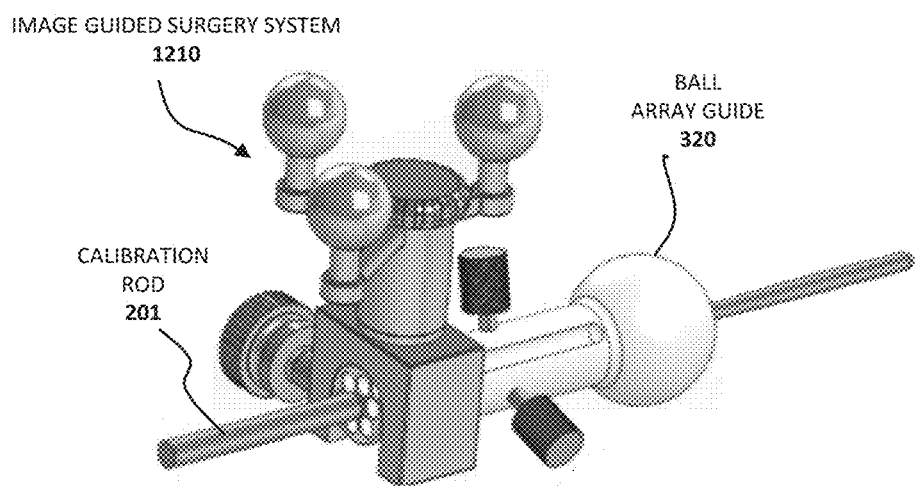
FIG. 40B is a perspective view of an image guided surgery system 1210 clamped onto a ball array guide 320 of a trajectory array guide system.

In some embodiments, the position and orientation of a trajectory array guide system can be tracked by an image guided neuronavigational system via instrument trackers clamped to a handle or array guide. In certain embodiments, the trajectory array guide system will have general compatibility with image guided surgery systems including, but not limited to, Varioguide™ and StarLINK™ (Brainlab, AG, Munich, Germany), as well as Vertek™ and SureTrak™ (Medtronic). FIG. 39 shows a perspective view of a trajectory array guide system engaged with an image guided surgery system 1200 which includes a probe 1202. The probe 1202 can be inserted into or engaged with the end opening 446 of the handle 440. The image guided surgery system 1200 can be secured to the handle using fastening and locking mechanisms, including the set screw 447. FIG. 40A shows a perspective view of an image guided surgery system 1210 clamped onto a handle 440 of a trajectory array guide system. FIG. 40B shows a perspective view of an image guided surgery system 1210 clamped directly onto a ball array guide 320 of a trajectory array guide system, with the assistance of a calibration rod 201.

Kits

The present disclosure provides kits for assembly of various embodiments of the trajectory array guide system of the present disclosure. In some embodiments, components of a kit may be separately packaged or packaged together in any configuration rendering a package suitable for sterilization. Steam, ethylene oxide, or gamma sterilization are preferred sterilization methods for the kits.

In some embodiments, the kit includes instructions for assembly of a trajectory array guide system.

In some embodiments, the kit includes the following: instructions for assembly of a trajectory array guide system; a container of imaging reagent; and one or more catheters which are compatible with the trajectory array guide system.

In some embodiments, the kit includes multiple imaging units or guide units for insertion into an array guide. In some embodiments, the kit includes a plurality of separate array units or reducers configured for guiding elongated tools of different diameters.

EXAMPLES

Example 1—Testing of Locking Mechanism

Base plates resembling base plate 550 of FIG. 18 and base plate 450 of FIG. 19A were produced as plastic 3D-printed prototypes. A locking nut resembling locking nut 530 of FIG. 18 and a ring clamp resembling ring clamp 80 of FIGS. 19B-C were produced as plastic 3D-printed prototypes. The base plates were tested to determine the effectiveness of the locking mechanism.

The base plates were held in a vise at one of the attachment tabs. A ball array guide resembling the ball array guide 220 in FIG. 18 and FIG. 19D was engaged into the socket of each base plate. A downward force was applied 30 mm from the bottom face of the base plate. The speed of the downward force was set at 50 mm/min. The test was first conducted in the absence of a locking mechanism, and then with the tapered threading locking mechanism (similar to FIG. 18) and with the ring-clamp mechanism (similar to FIGS. 19A-19D) on their respective base plates. The peak force required to displace the ball array guide was recorded. The results of the test are summarized in Table 1.

TABLE 1

Testing of Locking Mechanisms

| Locking Mechanism | Peak Force (N) | Peak Torque (N) or (Nmm) | Failure Mode |
|---|---|---|---|
| Absent | 1-2 | 30-60 Nmm | Ball moved |
| Tapered threading (similar to FIG. 18) | 7-8 | 210-240 Nmm | Ball moved |
| Ring-clamp (similar to FIGS. 19A-19C) | 16-18 | 480-540N | Base plate tab fractured |

The ring-clamp embodiment (similar to base plate 450 in combination with ring clamp 80 of FIGS. 19A-C) was found to yield the best results. The ring-clamp embodiment did not fail at a torque of 480-530 N which is twice the torque needed to fracture the catheter.

Example 2—Preparation of Imaging Cartridge

A gadolinium-based contrast solution is prepared by aspirating a gadolinium-based contrast agent into a 0.3 mL syringe. 0.04 mL of the gadolinium-based contrast agent is injected into a 10 mL pre-filled sterile saline syringe. A 2.0 to 5.0 inch, 25- to 30-gauge needle is attached to the sterile saline syringe and inverted multiple times to ensure mixing of the contrast agent with the sterile saline.

An imagining cartridge is provided which includes 7 imaging tubes in a symmetrical hexagonal pattern and an additional reference imagining tube. The 10 mL syringe containing the gadolinium imaging solution is used to sequentially fill the lumen of each tube by injecting imaging solution into the tube. The tip of the syringe is placed at the bottom of the tube, and the injection begins from the bottom of the tube. To ensure optimum MR visibility of the imaging cartridge tubes, the injection of the gadolinium imaging solution is continued while the syringe is slowly withdrawn from the tube, thereby preventing air from re-entering the tube. Each tube is visually inspected for air bubbles. If air bubbles are observed, the needle is reinserted to the base of the tube and additional gadolinium imaging solution is injected to push out the air bubbles.

Once all tubes have been filled with the gadolinium imaging solution, a reservoir at the top of the imaging cartridge is filled. An O-ring and sealing cap are then engaged with the top opening of the imaging cartridge to seal the imaging solution into the cartridge.

Example 3—Assembly of a Trajectory Array Guide System and Calibration with an Image Guided Surgery System A trajectory array guide system resembling the system shown in FIG. 38C is provided. A ring clamp is engaged with a tilted base plate, such that the ridge of the ring clamp is engaged with the outer groove of the base plate, similar to the configuration shown in FIGS. 19B-19D. The tension screw of the ring clamp is maintained in a loose position, and the ball of a ball array guide is engaged into the socket of the base plate. The tension screw is softly tightened.

A component of an image guided surgery system, such as an instrument tracker, is attached to the handle of the trajectory array guide system in a manner resembling the configuration shown in FIG. 40A. The handle is then engaged with the ball array guide by inserting the spike of the handle into the center channel of the array guide. The set-screws of the ball array guide are tightened to secure the engagement.

The trajectory array guide system can then be adjusted as necessary, with the tension screw of the ring clamp being fully tightened once the system has been properly aligned.

Example 4—Assembly of a Trajectory Array Guide System without a Handle and Calibration with an Image Guided Surgery System A trajectory array guide system resembling the system shown in FIG. 38C is provided. A ring clamp is engaged with a tilted base plate, such that the ridge of the ring clamp is engaged with the outer groove of the base plate, similar to the configuration shown in FIGS. 19B-19D. The tension screw of the ring clamp is maintained in a loose position.

A component of an image guided surgery system, such as an instrument tracker, is attached directly to a guide array of the trajectory array guide system, similar to the configuration shown in FIG. 40B. The ball of a ball array guide is then engaged into the socket of the base plate. The tension screw is softly tightened. A calibration rod is inserted into the center channel of the array guide.

The trajectory array guide system can then be adjusted as necessary, with the tension screw of the ring clamp being fully tightened once the system has been properly aligned.

Example 5—Surgical Preparation of a Skull and Attachment of Trajectory Array Guide System A cranial entry point is identified using image guided neuronavigational systems and MRI scans. The target head area is prepared for cranial entry according to standard medical practice, including cleaning and shaving the scalp around the cranial entry point. A craniotomy is conducted using standard surgical procedures to form a cranial entry at least 14 mm diameter at the planned cranial entry site.

A trajectory array guide system is provided, such as the system described in Example 3. The base plate is placed against the skull at the cranial entry point, with the bore of the base plate being located directly over the cranial entry hole. The base is rotated to a suitable orientation for attachment to the skull and to ensure that the tilt of the base is aligned with the surgical target. The base is then attached to the skull using self-drilling titanium bone screws through the holes on the base feet. The ring clamp and array guide are rotated and adjusted as necessary to provide access to the screw holes.

Example 6—Alignment of Trajectory Guide System, Selection of Target Trajectory, and Completion of Surgical Procedure A trajectory array guide system attached to a skull is provided, such as the arrangement described in Example 5.

The ring clamp is maintained in a loose position to allow the array guide to be freely rotated and adjusted as necessary. Using standard surgical procedures, an image guided surgery system is used to align the array guide in the direct of the surgical target. The trajectory and position of the array guide is then secured by gently hand-tightening the tension screw of the ring clamp.

A surgical probe is used to measure the distance from the top of the array guide to the surgical target, thereby providing the necessary insertion depth of the surgical instrument.

An imagining cartridge, such as the imaging cartridge prepared in Example 2, is carefully inserted into the array guide. The system is inspected to ensure that there is no gap between the top of the guide and the body of the imaging cartridge. Set-screws in the array guide are tightened to secure the engagement of the imaging cartridge and array guide.

All MRI unsafe tools, such as a metal handle or metal calibration rod are removed, and the head is placed within an MRI suite. The MRI equipment is turned on, and the resulting images are inspected to ensure that the entire trajectory array guide system and target surgical area are included in the MR images. Each of the seven trajectories is evaluated relative to the reference tube, and the best trajectory for the surgical target is selected. The channel corresponding to the selected trajectory is noted, and the imagining cartridge is removed.

The surgical procedure is then performed using the array channel of the selected trajectory. If the tube is a 14-gauge tube and the surgical instrument is a 16-gauge instrument, a reduce can be used to adjust the diameter of the array channel.

Once the surgical procedure is complete, the bone screws are withdrawn, and the trajectory array guide system is removed from the skull and disassembled. The trajectory array guide system can then be discarded as a single-use system, or it can be sterilized for reuse.

EQUIVALENTS AND SCOPE

Those skilled in the art will recognize, or be able to ascertain using no more than routine experimentation, many equivalents to the specific embodiments in accordance with the disclosure described herein.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Methods of the present disclosure are exemplified through discussion of certain embodiments which are not intended to be limiting to the scope of the general methods disclosed herein. Certain embodiments of the methods are discussed with different combinations of steps and different orders of steps. The combinations and order in which steps are presented are not intended to be limiting to the scope of the general methods presently disclosed. Individual steps disclosed herein can be combined in any combination and in any order within operable embodiments of the methods according to the knowledge and skill of those with ordinary skill in the art.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting. Figures included with the present disclosure are intended to be non-limiting depictions of general concepts of the present disclosure.

The invention claimed is:

1. A trajectory array guide system for defining a trajectory to a target location in the brain of a subject and for guiding an elongated tool along the trajectory, the trajectory array guide system comprising:
    (a) a base configured for attachment to the skull of the subject;
    (b) an array guide comprising a series of lumens;
    (c) an imaging unit configured for engagement with the array guide and configured to hold and direct imaging fluid along passages which are co-axial with the lumens of the array guide and configured to define a series of trajectories; and
    (d) an elongated handle configured for engagement with either the array guide or the imaging unit.

2. The trajectory array guide system of claim 1, wherein the array guide comprises a ball at one end, and wherein the base comprise a socket configured to receive and hold the ball of the array guide to form a ball-socket pivoting mechanism.

3. The trajectory array guide system of claim 2, wherein the socket has a central axis orthogonal to a plane formed by the bottom of the base.

4. The trajectory array guide system of claim 2, wherein the socket has a central axis which is non-orthogonal with respect to the plane formed by the bottom of the base such that the socket is tilted.

5. The trajectory array guide system of claim 4, wherein the central axis of the socket is angled by between about 10 degrees to about 30 degrees from the axis orthogonal to the plane formed by the bottom of the base.

6. The trajectory array guide system of claim 2, wherein the socket has an outer sidewall comprising threads or one or more grooves, wherein the threads or the one or more grooves are configured for attachment to a locking element to prevent the ball within the socket from pivoting movement.

7. The trajectory array guide system of claim 6, wherein the locking element is a ring-clamp configured for connection to the one or more grooves of the socket.

8. The trajectory array guide system of claim 6, wherein the locking element is a locking nut configured for connection to the threads of the socket.

9. The trajectory array guide system of claim 6, wherein the base includes a plurality of attachment members for attaching the base to the skull of the subject, and wherein the attachment members are accessible by an attachment tool when the locking element is engaged to the outer sidewall of the socket.

10. The trajectory array guide system of claim 2, wherein the array guide comprises a cylindrical or funnel-shaped member having a first end and a second end, wherein the ball is formed at the first end, and wherein the series of lumens each separately extend longitudinally along the length of the array guide from the first end to the second end of the array guide.

11. The trajectory array guide system of claim 10, wherein the series of lumens comprises seven substantially parallel lumens with six lumens arranged in a symmetrical hexagonal pattern and a seventh lumen located in the center of the symmetrical hexagonal pattern.

12. The trajectory array guide system of claim 2, wherein the imaging unit comprises an upper reservoir in fluid communication with a series of lower extensions which are co-axial with the lumens of the array guide.

13. The trajectory array guide system of claim 12, wherein the lower extensions are tubes configured to fit inside the lumens of the array guide.

14. The trajectory array guide system of claim 13, wherein the array guide includes an outer groove and the imaging unit includes an index tube configured to slide into the outer groove when the imaging unit is engaged with the array guide, wherein the index tube is configured to provide a reference point for identification of each of the tubes in a magnetic resonance image.

15. The trajectory array guide system of claim 13, wherein the array guide comprises a mechanism for locking the tubes of the imaging unit in place within the array guide.

16. The trajectory array guide system of claim 15, wherein the locking mechanism includes at least one set-screw which penetrates the array guide and makes tightening contact with at least one of the tubes.

17. The trajectory array guide system of claim 15, wherein the locking system includes three set-screws, each penetrating the body of the array guide to enter two different lumens as well as the central lumen.

18. The trajectory array guide system of claim 17, wherein the three set-screws are placed closer to the ball of the ball array guide than to the upper end of the ball array guide.

19. The trajectory array guide system of claim 2, wherein the elongated handle comprises a connector end configured for engagement with the outside or the inside of the imaging unit.

20. The trajectory array guide system of claim 19, wherein the connector end is configured for engagement with the outside of the imaging unit and includes an opening for a connector set-screw to lock the elongated handle on the imaging unit.

21. The trajectory array guide system of claim 19, wherein the elongated handle includes an end spike for insertion into one of the lumens of the array guide for direct engagement of the elongated handle with the array guide.

22. The trajectory array guide system of claim 21, wherein the elongated handle is at least partially hollow and has an outer end opening at the end opposite the end spike, and wherein the outer end opening is configured for connection to a navigation component of an image guided surgery system.

23. The trajectory array guide system of claim 2, further comprising a reducer tube for insertion into one of the lumens to provide a reduced diameter for the lumen.

24. The trajectory array guide system of claim 23, wherein the reducer tube comprises an adjustable stop for restraining movement of an elongated tool within the reducer tube.

25. The trajectory array guide system of claim 1, wherein the imaging unit includes a cap configured to seal the imaging fluid inside the imaging unit.

26. The trajectory array guide system of claim 1, wherein the elongated handle is configured for connection with a stereotaxic navigation system.

27. The trajectory array guide system of claim 1, wherein the elongated handle is configured for engagement with at least one of the array guide and the imaging unit when the array guide and imaging unit are assembled together with the base.

28. A method for delivering an elongated tool to a target location in the brain of a subject, the method comprising:
(a) providing a trajectory array guide system, the trajectory array guide system comprising a base, an array guide, an imaging unit, and a handle;
(b) performing a craniotomy at an entry location;
(c) connecting the base of the trajectory array guide system to the entry location;
(d) engaging the array guide with the base to form a pivoting mechanism;
(e) engaging the imaging unit with the array guide and aligning the array guide to target the location;
(f) imaging a series of trajectories towards the target location with magnetic resonance imaging (MRI);
(g) locking the trajectory array guide system and selecting a trajectory from the series of trajectories;
(h) removing the imaging unit and delivering the elongated tool to target location using the selected trajectory; and
(i) removing the trajectory array guide system from the skull of the subject.

29. The method of claim 28, wherein the step of connecting the base of the trajectory array guide system to the entry location comprises connecting the base to the entry location using bone screws through bottom tabs of the base.

30. The method of claim 28, wherein the method further comprises adding MRI contrast imaging reagent to the imaging unit prior to the imaging of the series of trajectories.

31. The method of claim 28, wherein the step of aligning the array guide to the target location comprises using the surgical navigation system to orient the series of trajectories toward the target location.

32. The method of claim 28, wherein the elongated tool is a catheter configured to deliver a drug to the target location.

33. The method of claim 28, wherein
(a) the base is configured for attachment to the skull of the subject;
(b) the array guide comprises a series of lumens;
(c) the imaging unit is configured for engagement with the array guide and configured to hold and direct imaging fluid along passages which are co-axial with the lumens of the array guide and configured to define a series of trajectories; and
(d) the handle is configured for engagement with either the array guide or the imaging unit;
wherein the array guide comprises a ball at one end, and wherein the base comprise a socket configured to receive and hold the ball of the array guide to form a ball-socket pivoting mechanism.

34. The method of claim 33, further comprising engaging the handle with at least one of the array guide and the imaging unit while the array guide and imaging unit are assembled together with the base.

35. The method of claim 28, wherein the trajectory array guide system comprises a stereotaxic navigation system connected to the handle.

36. A kit for providing a trajectory array guide system, the kit comprising:
(a) an array guide comprising a series of lumens and a ball at one end;
(b) a base configured for attachment to the skull of the subject, wherein the base comprises a socket configured to receive and hold the ball of the array guide to form a ball-socket pivoting mechanism;
(c) an imaging unit configured for engagement with the array guide and configured to hold and direct imaging fluid along passages which are co-axial with the lumens of the array guide and configured to define a series of trajectories; and
(d) an elongated handle configured for engagement with either the array guide or the imaging unit.

37. The kit of claim 36 further comprising one or more elongated tools configured to deliver a drug to a target location, wherein the elongated tools comprise one or more catheters.

38. The kit of claim 36, wherein all components are contained in one or more sterilized packages.

39. The kit of claim 36, wherein the elongated handle is configured for connection with a stereotaxic navigation system.

40. The kit of claim 36, wherein the elongated handle is configured for engagement with at least one of the array guide and the imaging unit when the array guide and imaging unit are assembled together with the base.

\* \* \* \* \*